United States Patent [19]

Satoh et al.

[11] Patent Number: 5,290,478
[45] Date of Patent: Mar. 1, 1994

[54] OPTICALLY ACTIVE COMPOUNDS

[75] Inventors: Masahiro Satoh; Tetsuya Watanabe, both of Kyoto; Kunikiyo Yoshio, Ohmihachiman; Hiroshi Kishiki, Takatsuki, all of Japan

[73] Assignee: Sanyo Chemical Industries, Ltd., Kyoto, Japan

[21] Appl. No.: 875,654

[22] Filed: Apr. 29, 1992

Related U.S. Application Data

[62] Division of Ser. No. 486,008, Feb. 27, 1990, Pat. No. 5,160,662.

[30] Foreign Application Priority Data

| Feb. 27, 1989 | [JP] | Japan | 1-47948 |
| Feb. 27, 1989 | [JP] | Japan | 1-47949 |
| Mar. 1, 1989 | [JP] | Japan | 1-49468 |
| Mar. 1, 1989 | [JP] | Japan | 1-49469 |
| Mar. 1, 1989 | [JP] | Japan | 1-49470 |
| Jul. 25, 1989 | [JP] | Japan | 1-192061 |
| Nov. 17, 1989 | [JP] | Japan | 1-299928 |
| Nov. 22, 1989 | [JP] | Japan | 1-303851 |

[51] Int. Cl.$^5$ ............ C09K 19/32; C09K 19/34; C07D 211/72; C07C 69/76
[52] U.S. Cl. ............ 252/299.62; 252/299.61; 252/299.67; 546/302; 546/303; 546/326; 546/330; 560/56; 560/100
[58] Field of Search ............ 252/299.01, 299.61, 252/299.62, 299.63, 299.64, 299.67; 546/302, 303, 326, 330; 560/56, 100

[56] References Cited

U.S. PATENT DOCUMENTS

| 4,576,732 | 3/1986 | Isogai et al. | 252/299.65 |
| 4,613,209 | 9/1986 | Goodby et al. | 252/299.65 |

FOREIGN PATENT DOCUMENTS

| 293910 | 12/1988 | European Pat. Off. |
| 294852 | 12/1988 | European Pat. Off. |
| 62-169883 | 7/1987 | Japan |
| 8909764 | 10/1989 | World Int. Prop. O. |

OTHER PUBLICATIONS

Liquid Crystals and Ordered Fluids, vol. 4, pp. 1-32, Goodby et al., "Some Novel Ferroelectric Smectic Liquid Crystals".
Chem. Abst., vol. 110, No. 11 Mar. 13, 1989, p. 656, Abst. No. 94711x.
Mol. Cryst. Liq. Cryst. 1984, vol. 110, pp. 175-203, Goodby et al. Ferroelectric Liquid Crystals–Structure and Design.
Synthesis, Journal of Synthetic Organic Chemistry, No. 8, Aug. 1986, pp. 605-692.

*Primary Examiner*—Robert L. Stoll
*Assistant Examiner*—Shean C. Wu
*Attorney, Agent, or Firm*—Oblon, Spivak, McClelland, Maier & Neustadt

[57] ABSTRACT

Optically active compounds having the following formulae (1), (2) or (3)

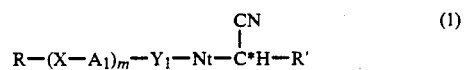

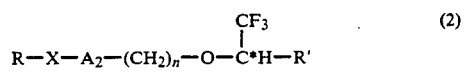

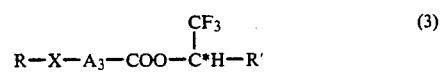

wherein R and R' are $C_{1-20}$ alkyl groups; X and $Y_1$ are —, O, S, or divalent groups such as COO, OOC and OCOO; m is 0 or 1; n is 0 to 5; $A_2$ is a cyclic group, such as p,p'-biphenylene, 2,6-naphthylene, 2,5-pyrimidinylene-1,4-phenylene, $A_1$—$Y_2$-pyridylene or $A_4$—$Y_2$—$A_5$; $Y_2$ is $CH_2CH_2$ or $C≡C$; $A_3$ is 2,6-naphthylene, $A_1$—$Y_2$-pyridylene or $A_6$—$CH_2CH_2$—$A_7$; and $A_1$, $A_4$, $A_5$, $A_6$ and $A_7$ are cyclic groups, such as 1,4-phenylene and/or 4,4'-biphenylene.

14 Claims, 34 Drawing Sheets

OPTICALLY ACTIVE COMPOUNDS

This is a division of U.S. patent application Ser. No. 07/486,008, filed on Feb. 27, 1990, now U.S. Pat. No. 5,160,662.

BACKGROUND OF THE INVENTION

1. Field of the Invention

This invention relates to optically active compounds which are useful as components for liquid crystal compositions.

2. Description of the Prior Art

In addition to combinations of liquid crystal compounds which exhibit chiral smectic phases, there have been known ferroelectric liquid crystal materials, obtained by adding optically active compounds to a liquid crystal matrix, such as liquid crystal compounds or compositions showing smectic C phase or smectic H phase [Ann. Phys.,3,237 (1987)].

However, most optically active compounds, used for this purpose, produced from optically active alcohols such as optically active 2-octanol or optically active 2-butanol, of small intramolecular dipole moment, provide a long response time when added to liquid crystal compounds or compositions as a matrix, and are not feasible for practical use.

SUMMARY OF THE INVENTION

Accordingly, it is an object of the present invention to provide an optically active compound practically suitable for adding to liquid crystal compounds or compositions.

It is another object of the present invention to provide an optically active compound which can attain an improved response time when added to liquid crystal compounds or compositions as a matrix.

It is still another object of the present invention to provide a liquid crystal, containing an optically active compound, showing an improved response time.

These and other objects of the present invention as hereinafter will become more readily apparent are provided b optically active compounds represented by the following formulae (1), (2) or (3):

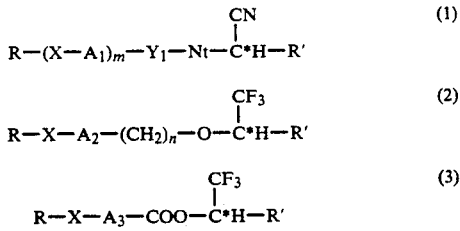

wherein R and R' are the same or different alkyl groups containing 1 to 20 carbon atoms, which are unsubstituted or are substituted with at least one substituent selected from the group consisting of F, Cl and alkoxy groups; X is—(direct bond), O, S, COO, OOC, OCOO, or C≡C; $Y_1$ is—(direct bond), O, S, COO, OOC, OCOO, $CH_2O$, $OCH_2$, C≡C or $CH_2CH_2$;

$A_1$ is acyclic group selected from the group consisting of Ph, Pyr, Pym, Pyd, Pyz, Bp and Nt; m is 0 or 1; n is 0 or an integer of 1 to 5; $A_2$ is Bp, Nt, Pym-Ph, Ph-Pym, $A_1$—$Y_2$—Pyr or $A_4$—$Y_2$—$A_5$; $Y_2$ is $CH_2CH_2$ or C≡C, $A_4$ and $A_5$ are the same or different cyclic groups selected from the group consisting of Ph and Bp; $A_3$ is Nt, $A_1$—$Y_2$—Pyr or $A_6$—$Y_3$—$A_7$, $Y_3$ is $CH_2CH_2$, $A_6$ and $A_7$ are the same or different cyclic groups selected from the group consisting of Ph, Bp and Nt; and Ph, Pyr, Pym, Pyd, Pyz, Bp and Nt represent 1,4-phenylene, 2,5-pyridylene, 2,5-pyrimidinylene, 3,6-pyridazinylene, 2,5-pyrazinylene, 4,4'-biphenylene and 2,6-naphthylene groups, respectively, which are unsubstituted or are substituted with at least one substituent selected from the group consisting of F, Cl, CN, $NO_2$ and $CF_3$.

BRIEF DESCRIPTION OF THE DRAWINGS

FIG. 1(a) to FIG. 13(a) are IR spectra of optically active compounds of Examples 1 to 13, respectively.

FIG. 1(b) to FIG. 13(b) are H-NMR spectra of optically active compounds of Examples 1 to 13, respectively, FIG. 6(c) to FIG. 13(c) are F-NMR spectra of optically active compounds of Examples 6 to 13, respectively.

DETAILED DESCRIPTION OF THE PREFERRED EMBODIMENTS

Figure 1A:
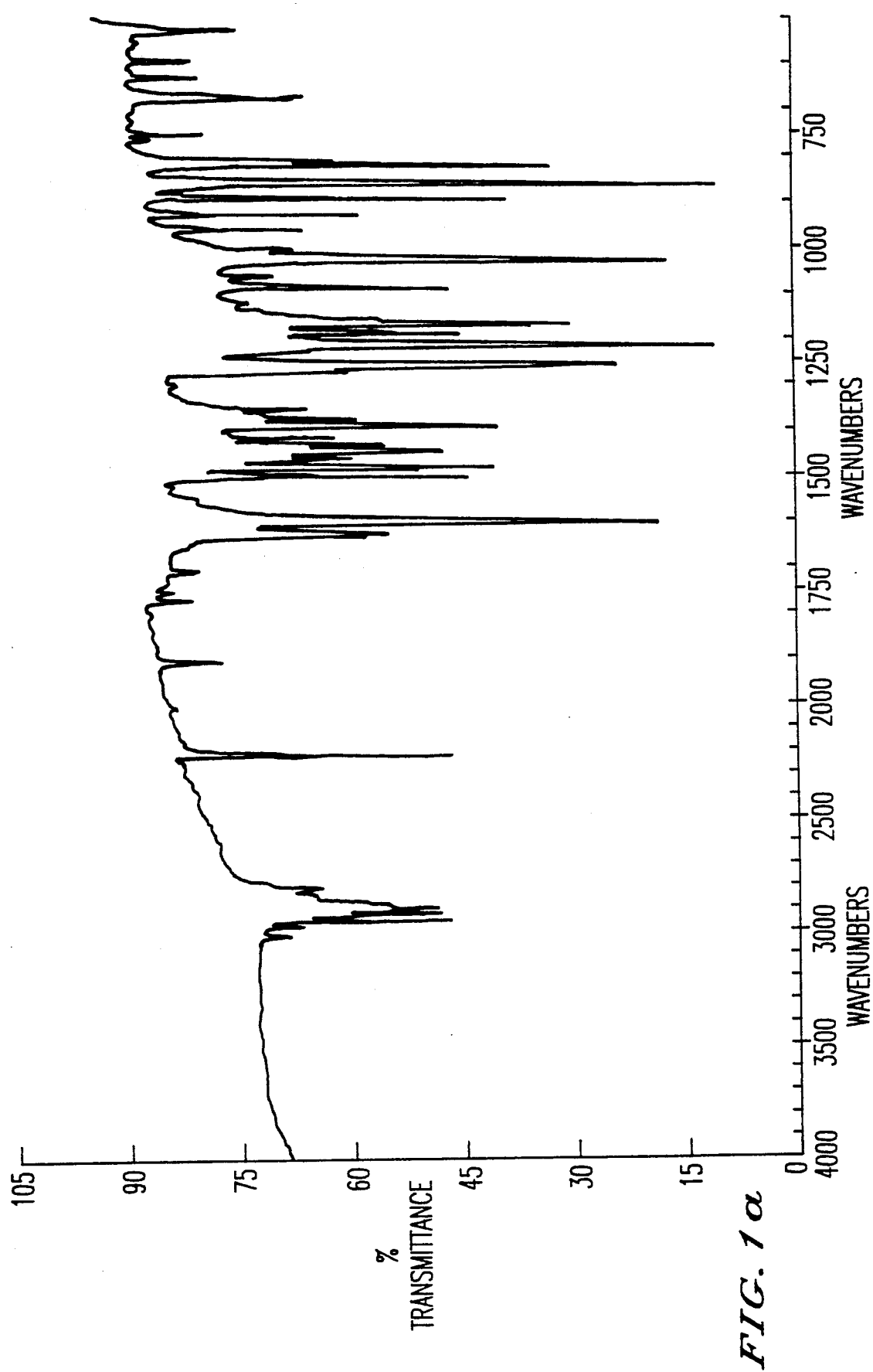

In the formulae (1), (2) and (3), R and R' are the same or different alkyl groups containing usually 1-20, preferably 1-18 carbon atoms, which are unsubstituted or are substituted with at least one substituent selected from the group consisting of fluorine, chlorine and alkoxy groups containing 1 to 10 or more carbon atoms. Suitable alkyl groups are, for example, straight-chain alkyl groups, such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, and n-octadecyl groups; branched alkyl groups, such as iso-propyl, 1-methylpropyl, 1-methylbutyl, 1-methylpentyl, 1-methylhexyl, 1-methylheptyl, 1-methyloctyl, 2-methylpropyl, 2-methylbutyl, 2-methylpentyl, 2-methylhexyl, 2-methylheptyl, 2-methyloctyl, 2-methylnonyl, 2-methyldecyl, 2-methylundecyl, 2-methyldodecyl, 2-methyltridecyl, 2-methyltetradecyl, 3-methylbutyl, 3-methylpentyl, 3-methylhexyl, 3-methylheptyl, 3-methyloctyl, 4-methylpentyl, 4-methylhexyl, 4-methylheptyl, 4-methyloctyl, 5-methylhexyl, 5-methylheptyl, 5-methyloctyl, 5-methylnonyl, 5-methyldecyl, 6-methylheptyl, 6-methyloctyl, 6-methylnonyl, 6-methyldecyl, 7-methyloctyl, 7-methylnonyl, 7-methyldecyl, 8-methyldecyl, 9-methyldecyl and 9-methylundecyl groups; cyclic alkyl groups, such as cyclopentyl, cyclohexyl, and cycloheptyl groups; and substituted alkyl groups, including F-substituted alkyl groups, such as 2-fluoropropyl, 2-fluorobutyl, 2-fluoropentyl, 2-fluorohexyl, 2-fluoroheptyl, 2-fluorooctyl, 2-fluorononyl, 2-fluorodecyl, 2-fluoroundecyl, 2-fluorododecyl, 2-fluorotridecyl, 2-fluorotetradecyl, 3-fluoropropyl, 4-fluorobutyl, 5-fluoropentyl, 6-fluorohexyl, 7-fluoroheptyl, 8-fluorooctyl, 9-fluorononyl, 10-fluorodecyl, 11-fluoroundecyl, 12-fluorododecyl, 2-(perfluoro-n-butyl)ethyl, 2-(perfluoro-n-hexyl)ethyl, 2-(perfluoro-n-octyl)ethyl, 2-(perfluoro-n-decyl)ethyl, 2-fluoro-3-methylbutyl, 2-fluoro-3-methylpentyl and 2-fluoro-4-methylpentyl groups, and alkoxy-substituted alkyl groups, such as 2-methoxypropyl, 2-ethoxypropyl, 2-propoxypropyl, 2-butoxypropyl, 2-pentyloxypropyl, 2-heptyloxypropyl, 2-oxtyloxypropyl, 2-nonyloxypropyl, 2-decyloxypropyl, 2-(2-methylbutyloxy)propyl, 2-isopropoxypropyl, 3-butyloxybutyl, 3-pentyloxybutyl, 3-hexyloxybutyl, 3-heptyloxybutyl, 3-octyloxybutyl, 3-nonyloxybutyl, 3-decyloxybutyl, 3-(2-methylbutyloxy)butyl, 3-iso-propyloxybutyl, 4-methoxypentyl, 4-ethoxypentyl, 4-propoxypentyl, 4-butyloxypentyl, 4-pentyloxypentyl, 4-hexyloxypentyl, 4-heptyloxypentyl, 4-octyloxypentyl, 4-nonyloxypentyl, 4-decyloxypentyl, 4-(2-methylbutyloxy)pentyl, 4-(2-methylpentyloxy)pentyl and 4-isopropoxypentyl groups.

Alkyl groups R and R' may contain one or more asymmetric carbon atoms, and may be optically active (hereinafter referred to as oa). Suitable oa groups include for example, oa alkyl groups, such as oa 1-methylpropyl, oa 1-methylbutyl, oa 1-methylpentyl, oa 1-methylhexyl, oa 1-methylheptyl, oa 1-methyloctyl, oa 2-methylbutyl, oa 2-methylpentyl, oa 2-methylhexyl, oa 2-methylheptyl, oa 2-methylundecyl, oa 2-methyldodecyl, oa 2-methyltridecyl, oa 2-methyltetradecyl, oa 3-methylpentyl, oa 3-methylhexyl, oa 3-methylheptyl, oa 3-methyloctyl, oa 4-methylhexyl, oa 3-methylheptyl, oa 3-methyloctyl, oa 4-methylhexyl, oa 4-methylheptyl, oa 4-methyloctyl, oa 5-methylheptyl, oa 5-methyloctyl, oa 5-methylnonyl, oa 5-methyldecyl, oa 6-methyloctyl, oa 6-methylnonyl, oa 6-methyldecyl, oa 7-methylnonyl, oa 7-methyldecyl, oa 8-methyldecyl and oa 9-methylundecyl groups; and substituted oa alkyl groups, including F-substituted oa alkyl groups, such as oa 2-fluoropropyl, oa 2-fluorobutyl, oa 2-fluorooctyl, oa 2-fluorononyl, oa 2-fluorodecyl, oa 2-fluoroundecyl, oa 2-fluorododecyl, oa 2-fluorotridecyl, oa 2-fluorotetradecyl, oa 2-fluoro-3-methylbutyl, oa 2-fluoro-3-methylpentyl and oa 2-fluoro-4-methylpentyl groups; Cl-substituted oa alkyl groups, such as oa 2-chloropropyl, oa 2-chlorobutyl, oa 2-chloropentyl, oa 2-chlorohexyl, oa 2-chloroheptyl, oa 2-chlorooctyl, oa 2-chlorononyl, oa 2-chlorodecyl, oa 2-chloroundecyl, oa 2-chlorododecyl, oa 2-chlorotridecyl, oa 2-chloro-3-methylbutyl, oa 2-chloro-3-methylpentyl and oa 2-chloro-4-methylpentyl groups; and alkoxy-substituted oa alkyl groups, such as 2-oa methoxypropyl, oa 2-ethoxypropyl, oa 2-propoxypropyl, oa 2-butoxypropyl, oa 2-pentyloxypropyl, oa 2-nonyloxypropyl, oa 2-decyloxypropyl, oa 2-(2-methylbutyloxypropyl, oa 2-iso-propoxypropyl, oa 3-methoxybutyl, oa 3-ethoxybutyl, oa 3-propoxybutyl, oa 3-butyloxybutyl, oa 3-pentyloxybutyl, oa 3-hexyloxybutyl, oa 3-heptyloxybutl, oa 3-octyloxybutyl, oa 3-nonyloxybutyl, oa 3-decyloxybutyl, oa 3-(3-methylbutyloxy)butyl, oa 3-isopropyloxybutyl, oa 4-methoxypentyl, oa 4-ethoxypentyl, oa 4-propoxypentyl, oa 4-butyloxypentyl, oa 4-pentyloxypentyl, oa 4-hexyloxxypentyl, oa 4-decyloxpentyl, oa 4-(2-methyl-butyloxy)pentyl and 4-isopropoxy-pentyl groups.

Among these, preferred are alkyl groups containing 1 to 16, particularly 1 to 15, more particularly 1 to 14 carbon atoms.

In the formulae (1), (2) and (3), X is preferably —(-direct bond), O (ether oxygen linkage), C≡C or S, more preferably —, C≡C or O particularly—or O. Among $Y_1$, preferred are O, COO, $CH_2O$ and C≡C, particularly O, COO and C≡C.

In the formulae (1), (2) and (3), suitable examples of said cyclic group $A_1$ are

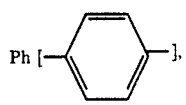

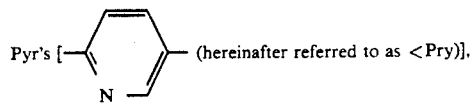

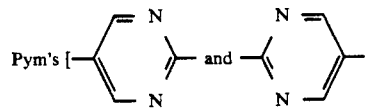

(hereinafter referred to as Pym> and <Prm, respectively)],

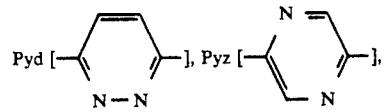

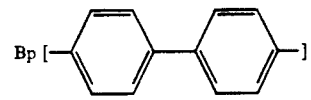

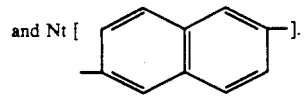

These cyclic groups are unsubstituted or are substituted with 1-4 halogen atoms, such as fluorine, chlorine and bromine atoms, or 1-2 substituent groups, such as cyano, nitro and trifluoromethyl groups. Exemplary of suitable substituted cyclic groups are F-substituted Ph's, such as

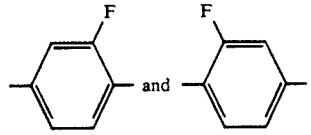

(hereinafter referred to as PhF and FPh, respectively), and F-substituted Bp's such as Ph-Phf and FPh-Ph.

Among these, preferred are Ph, and Pyr's.

In the formula (2), n is preferably 0 to 3, more preferably 0 to 1.

In the formula (2), illustrative examples of said cyclic group $A_2$ include the following:
1) Bp; 2) Nt; 3) Pym-Ph's [Pym>-Ph and <Pym-Ph] and Ph-Pym's [Ph-<Pym and Ph-Pym>], preferably Pym>-Ph, Ph-<Pym and Ph-Pym>; 4) $A_4$—$Y_2$—$A_5$, wherein $A_4$ and $A_5$ are independently selected from Ph and Bp; and 5) $A_1$—$Y_2$—Pyr, preferably those, wherein $A_1$ is Ph, Bp, Pyd or Nt.

In the general formula (3), illustrative examples of said cyclic groups $A_3$ include the following:
1) Nt; 2) $A_6$—$CH_2$—$CH_2$—$A_7$, wherein $A_6$ and $A_7$ are independently selected from Ph, Bp and Nt; and 3) $A_1$—$Y_2$—Pyr, preferably those, wherein $A_1$ is Ph, Bp, Pym>, Pyd or Nt.

In the above, each cyclic group (Ph, Pyr, Pym, Pyd, Pyz, Bp or Nt), constituting $A_1$, $A_2$, $A_3$, $A_4$, $A_5$, $A_6$ and $A_7$ may be independently selected from Ph, Bp and Nt; and 3) $A_1$—$Y_2$—Pyr, preferably those, wherein $A_1$ is Ph, Bp, <Pyr, Pym>, Pyd or Nt.

In the above, each cyclic group (Ph, Pyr, Pym, Pyd, Pyz, Bp or Nt), constituting $A_1$, $A_2$, $A_3$, $A_4$, $A_5$, $A_6$ and $A_7$ may be substituted with 1-4 fluorine atoms or with 1-2 substituents selected from the group consisting of Cl, cyano, nitro and trifluoromethyl groups; among which preferred are substituted with up to 4 fluorine atoms.

Illustrative examples of the compounds represented by the formulae (1), (2) and (3) include those shown in Table 1-1 to Table 9.

In these Tables and also hereinafter, are used the following abbreviated words: MET:methyl; ETH:ethyl; PRO:n-propyl; BUT:n-butyl; PEN:n-pentyl; H:n-hexyl; HEP:n-heptyl; OCT:n-octyl; NON:n-nonyl; DEC:n-decyl; UND:n-undecyl; DOD:n-dodecyl; iPr:i-propyl; $PF_8$:n-$C_6F_{13}CH_2CH_2$; $PF_{10}$:n-$C_8F_{17}CH_2CH_2$;

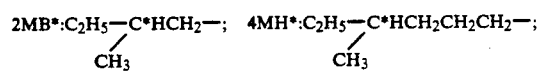

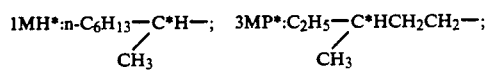

$LAC^*$:$C_2H_5$—OOC—$C^*H$—;   EOCM:$C_2H_5$—OOC—$CH_2$;
         |
        $CH_3$ nPrOMe:n-propoxymethyl; iPrOMe:i-propoxymethyl; nPrOEt:n-propoxyethyl; iPrOEt:i-propoxyethyl; nBuOMe:n-butoxymethyl; iBuOMe:i-butoxymethyl; EtOPr:3-ethoxypropyl; iPrOPr:3-(i-propoxy)-propyl; 2EOPr*:2-ethoxypropyl; 2POPr*:2-(n-propoxy)-propyl;

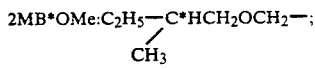

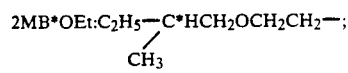

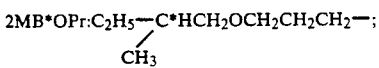

TABLE 1-1

Case of m = 0 (1-1)

$$R-Y_1-Nt-C^*H-R'$$
$$\phantom{R-Y_1-Nt-}|$$
$$\phantom{R-Y_1-Nt-}CN$$

| No. | R | $Y_1$ | R' |
|---|---|---|---|
| 1-1 | MET | O | MET |
| 1-2 | ETH | O | MET |
| 1-3 | PRO | O | MET |
| 1-4 | BUT | O | MET |
| 1-5 | PEN | O | MET |
| 1-6 | HEX | O | MET |
| 1-7 | HEP | O | MET |
| 1-8 | OCT | O | MET |
| 1-9 | NON | O | MET |
| 1-10 | DEC | O | MET |
| 1-11 | $PF_8$ | O | MET |
| 1-12 | $PF_{10}$ | O | MET |
| 1-13 | 2MB* | O | MET |
| 1-14 | 4MH* | O | MET |
| 1-15 | 1MH* | O | MET |
| 1-16 | LAC* | O | MET |
| 1-17 | MET | COO | MET |
| 1-18 | HEX | COO | MET |
| 1-19 | HEP | COO | MET |
| 1-20 | OCT | COO | MET |
| 1-21 | NON | COO | MET |
| 1-22 | DEC | COO | MET |
| 1-23 | MET | O | HEX |
| 1-24 | HEX | O | HEX |

TABLE 1-1-continued

Case of m = 0 (1-1)

$$R-Y_1-Nt-C^*H-R'$$
$$\phantom{R-Y_1-Nt-}|$$
$$\phantom{R-Y_1-Nt-}CN$$

| No. | R | $Y_1$ | R' |
|---|---|---|---|
| 1-25 | HEP | O | HEX |
| 1-26 | OCT | O | HEX |
| 1-27 | NON | O | HEX |
| 1-28 | DEC | O | HEX |
| 1-29 | $PF_8$ | O | HEX |
| 1-30 | $PF_{10}$ | O | HEX |
| 1-31 | 2MB* | O | HEX |
| 1-32 | 4MH* | O | HEX |
| 1-33 | 1MH* | O | HEX |
| 1-34 | LAC* | O | HEX |
| 1-35 | HEX | COO | HEX |
| 1-36 | HEP | COO | HEX |
| 1-37 | OCT | COO | HEX |
| 1-38 | NON | COO | HEX |
| 1-39 | DEC | COO | HEX |
| 1-40 | MET | O | iPr |
| 1-41 | HEX | O | iPr |
| 1-42 | HEP | O | iPr |
| 1-43 | OCT | O | iPr |
| 1-44 | NON | O | iPr |
| 1-45 | DEC | O | iPr |
| 1-46 | $PF_8$ | O | iPr |
| 1-47 | $PF_{10}$ | O | iPr |
| 1-48 | 2MB* | O | iPr |
| 1-49 | 4MH* | O | iPr |
| 1-50 | 1MH* | O | iPr |
| 1-51 | LAC* | O | iPr |
| 1-52 | HEX | COO | iPr |
| 1-53 | HEP | COO | iPr |
| 1-54 | OCT | COO | iPr |
| 1-55 | NON | COO | iPr |
| 1-56 | DEC | COO | iPr |

TABLE 1-2

Case of m = 1 (1-2)

$$R-X-A_1-Y_1-Nt-C^*H-R'$$
$$\phantom{R-X-A_1-Y_1-Nt-}|$$
$$\phantom{R-X-A_1-Y_1-Nt-}CN$$

| No. | R | X | $A_1$ | $Y_1$ | R' |
|---|---|---|---|---|---|
| 1-57 | HEX | — | Ph | $CH_2O$ | MET |
| 1-58 | HEX | — | Ph | $CH_2O$ | HEX |
| 1-59 | HEX | — | Ph | $CH_2O$ | iPr |
| 1-60 | HEX | O | Ph | $CH_2O$ | MET |
| 1-61 | HEX | O | Ph | $CH_2O$ | HEX |
| 1-62 | HEX | O | Ph | $CH_2O$ | iPr |
| 1-63 | HEX | — | Ph | COO | MET |
| 1-64 | HEX | — | Ph | COO | HEX |
| 1-65 | HEX | — | Ph | COO | iPr |
| 1-66 | HEX | O | Ph | COO | MET |
| 1-67 | HEX | O | Ph | COO | HEX |
| 1-68 | HEX | O | Ph | COO | iPr |
| 1-69 | HEX | O | PhF | COO | MET |
| 1-70 | HEX | O | PhF | COO | HEX |
| 1-71 | HEX | O | PhF | COO | iPr |
| 1-72 | HEX | O | FPh | COO | MET |
| 1-73 | HEX | O | FPh | COO | HEX |
| 1-74 | HEX | O | FPh | COO | iPr |
| 1-75 | HEX | — | Ph | C#C | MET |
| 1-76 | HEX | — | Ph | C#C | HEX |
| 1-77 | HEX | — | Ph | C#C | iPr |
| 1-78 | HEX | O | Ph | C#C | MET |
| 1-79 | HEX | O | Ph | C#C | HEX |
| 1-80 | HEX | O | Ph | C#C | iPr |
| 1-81 | HEX | O | PhF | C#C | MET |
| 1-82 | HEX | O | PhF | C#C | HEX |
| 1-83 | HEX | O | PhF | C#C | iPr |
| 1-84 | HEX | O | FPh | C#C | MET |
| 1-85 | HEX | O | FPh | C#C | HEX |
| 1-86 | HEX | O | FPh | C#C | iPr |
| 1-87 | HEX | — | <Pyr | COO | MET |
| 1-88 | HEX | — | <Pyr | COO | HEX |
| 1-89 | HEX | — | <Pyr | COO | iPr |
| 1-90 | HEX | O | <Pyr | COO | MET |
| 1-91 | HEX | O | <Pyr | COO | HEX |

TABLE 1-2-continued

Case of m = 1 (1-2)

$$R-X-A_1-Y_1-Nt-\underset{\underset{R'}{|}}{C^*H}$$ with CN on the C*

| No. | R | X | $A_1$ | $Y_1$ | R' |
|---|---|---|---|---|---|
| 1-92 | HEX | O | <Pyr | COO | iPr |
| 1-93 | DEC | — | Ph | CH₂O | MET |
| 1-94 | DEC | — | Ph | CH₂O | HEX |
| 1-95 | DEC | — | Ph | CH₂O | iPr |
| 1-96 | DEC | O | Ph | CH₂O | MET |
| 1-97 | DEC | O | Ph | CH₂O | HEX |
| 1-98 | DEC | O | Ph | CH₂O | iPr |
| 1-99 | DEC | — | Ph | COO | MET |
| 1-100 | DEC | — | Ph | COO | HEX |
| 1-101 | DEC | — | Ph | COO | iPr |
| 1-102 | DEC | O | Ph | COO | MET |
| 1-103 | DEC | O | Ph | COO | HEX |
| 1-104 | DEC | O | Ph | COO | iPr |
| 1-105 | DEC | O | PhF | COO | MET |
| 1-106 | DEC | O | PhF | COO | HEX |
| 1-107 | DEC | O | PhF | COO | iPr |
| 1-108 | DEC | O | FPh | COO | MET |
| 1-109 | DEC | O | FPh | COO | HEX |
| 1-110 | DEC | O | FPh | COO | iPr |
| 1-111 | DEC | — | Ph | C#C | MET |
| 1-112 | DEC | — | Ph | C#C | HEX |
| 1-113 | DEC | — | Ph | C#C | iPr |
| 1-114 | DEC | O | Ph | C#C | MET |
| 1-115 | DEC | O | Ph | C#C | HEX |
| 1-116 | DEC | O | Ph | C#C | iPr |
| 1-117 | DEC | O | PhF | C#C | MET |
| 1-118 | DEC | O | PhF | C#C | HEX |
| 1-119 | DEC | O | PhF | C#C | iPr |
| 1-120 | DEC | O | FPh | C#C | MET |
| 1-121 | DEC | O | FPh | C#C | HEX |
| 1-122 | DEC | O | FPh | C#C | iPr |
| 1-123 | DEC | — | <Pyr | COO | MET |
| 1-124 | DEC | — | <Pyr | COO | HEX |
| 1-125 | DEC | — | <Pyr | COO | iPr |
| 1-126 | DEC | O | <Pyr | COO | MET |
| 1-127 | DEC | O | <Pyr | COO | HEX |
| 1-128 | DEC | O | <Pyr | COO | iPr |

TABLE 2-1

Case of $A_2$ = Bp, n = 0 (2-1-1)

$$R-X-Bp-O-\underset{\underset{R'}{|}}{C^*H}$$ with CF₃ on the C*

| No. | R | X | $A_2$ = Bp | R' |
|---|---|---|---|---|
| 2-1 | HEP | O | Ph-Ph | HEX |
| 2-2 | OCT | O | Ph-Ph | HEX |
| 2-3 | NON | O | Ph-Ph | HEX |
| 2-4 | DEC | O | Ph-Ph | HEX |
| 2-5 | UND | O | Ph-Ph | HEX |
| 2-6 | DOD | O | Ph-Ph | HEX |
| 2-7 | HEP | — | Ph-Ph | HEX |
| 2-8 | OCT | — | Ph-Ph | HEX |
| 2-9 | NON | — | Ph-Ph | HEX |
| 2-10 | DEC | — | Ph-Ph | HEX |
| 2-11 | UND | — | Ph-Ph | HEX |
| 2-12 | DOD | — | Ph-Ph | HEX |
| 2-13 | DEC | O | Ph-Ph | PEN |
| 2-14 | DEC | — | Ph-Ph | PEN |
| 2-15 | DEC | O | Ph-Ph | OCT |
| 2-16 | DEC | — | Ph-Ph | OCT |
| 2-17 | DEC | O | Ph-Ph | DEC |
| 2-18 | DEC | — | Ph-Ph | DEC |
| 2-19 | PF₈ | O | Ph-Ph | HEX |
| 2-20 | PF₁₀ | O | Ph-Ph | HEX |
| 2-21 | 2MB* | O | Ph-Ph | HEX |
| 2-22 | 2MB* | — | Ph-Ph | HEX |
| 2-23 | 4MH* | O | Ph-Ph | HEX |
| 2-24 | 4MH* | — | Ph-Ph | HEX |
| 2-25 | 1MH* | — | Ph-Ph | HEX |
| 2-26 | DEC | O | Ph-Ph | nBuOMe |
| 2-27 | DEC | — | Ph-Ph | nBuOMe |
| 2-28 | DEC | O | Ph-Ph | iBuOMe |
| 2-29 | DEC | — | Ph-Ph | iBuOMe |
| 2-30 | DEC | O | Ph-Ph | 2MB*OMe |

TABLE 2-1-continued

Case of $A_2$ = Bp, n = 0 (2-1-1)

$$R-X-Bp-O-\underset{\underset{R'}{|}}{C^*H}$$ with CF₃ on the C*

| No. | R | X | $A_2$ = Bp | R' |
|---|---|---|---|---|
| 2-31 | DEC | — | Ph-Ph | 2MB*OMe |
| 2-32 | DEC | O | Ph-Ph | iPrOMe |
| 2-33 | DEC | — | Ph-Ph | iPrOMe |
| 2-34 | DEC | O | Ph-Ph | nPrOEt |
| 2-35 | DEC | — | Ph-Ph | nPrOEt |
| 2-36 | DEC | O | Ph-Ph | iPrOEt |
| 2-37 | DEC | — | Ph-Ph | iPrOEt |
| 2-38 | OCT | O | Ph-Ph | 2MB*OEt |
| 2-39 | NON | O | Ph-Ph | 2MB*OEt |
| 2-40 | DEC | O | Ph-Ph | 2MB*OEt |
| 2-41 | OCT | — | Ph-Ph | 2MB*OEt |
| 2-42 | NON | — | Ph-Ph | 2MB*OEt |
| 2-43 | DEC | — | Ph-Ph | 2MB*OEt |
| 2-44 | DEC | O | Ph-Ph | EtOPr |
| 2-45 | DEC | — | Ph-Ph | EtOPr |
| 2-46 | DEC | O | Ph-Ph | iPrOpr |
| 2-47 | DEC | — | Ph-Ph | iPrOPr |
| 2-48 | OCT | O | Ph-Ph | 2MB*OPr |
| 2-49 | NON | O | Ph-Ph | 2MB*OPr |
| 2-50 | DEC | O | Ph-Ph | 2MB*OPr |
| 2-51 | OCT | — | Ph-Ph | 2MB*OPr |
| 2-52 | NON | — | Ph-Ph | 2MB*OPr |
| 2-53 | DEC | — | Ph-Ph | 2MB*OPr |
| 2-54 | OCT | O | Ph-PhF | HEX |
| 2-55 | NON | O | Ph-PhF | HEX |
| 2-56 | DEC | O | Ph-PhF | HEX |
| 2-57 | OCT | — | Ph-PhF | HEX |
| 2-58 | NON | — | Ph-PhF | HEX |
| 2-59 | DEC | — | Ph-PhF | HEX |
| 2-60 | DEC | O | Ph-PhF | 2MB*OEt |
| 2-61 | DEC | O | Ph-PhF | 2MB*OPr |
| 2-62 | 2MB* | O | Ph-PhF | HEX |
| 2-63 | DEC | — | FPh-Ph | HEX |
| 2-64 | DEC | O | FPh-Ph | 2MB*OEt |
| 2-65 | 2MB* | O | FPh-Ph | HEX |
| 2-66 | 2EOPr* | O | Ph-Ph | HEX |
| 2-67 | 2POPr* | O | Ph-Ph | HEX |
| 2-68 | 2EOPr* | O | Ph-PhF | HEX |
| 2-69 | 2EOPr* | O | FPh-Ph | HEX |

TABLE 2-2

Case of $A_2$ = Bp, n = 1 (2-1-2)

$$R-X-Bp-CH_2-O-\underset{\underset{R'}{|}}{C^*H}$$ with CF₃ on the C*

| No. | R | X | $A_2$ = Bp | R' |
|---|---|---|---|---|
| 2-70 | DEC | O | Ph-Ph | HEX |
| 2-71 | DEC | — | Ph-Ph | HEX |
| 2-72 | DEC | O | Ph-Ph | PEN |
| 2-73 | DEC | O | Ph-PhF | HEX |
| 2-74 | DEC | — | Ph-PhF | HEX |
| 2-75 | DEC | O | FPh-Ph | HEX |

TABLE 3

Case of $A_2$ = Nt (2-2)

$$R-X-Nt-(CH_2)_n-O-\underset{\underset{R'}{|}}{C^*H}$$ with CF₃ on the C*

| No. | R | X | n | R' |
|---|---|---|---|---|
| 3-1 | HEX | O | 1 | HEX |
| 3-2 | HEP | O | 1 | HEX |
| 3-3 | OCT | O | 1 | HEX |
| 3-4 | NON | O | 1 | HEX |
| 3-5 | DEC | O | 1 | HEX |
| 3-6 | UND | O | 1 | HEX |
| 3-7 | DOD | O | 1 | HEX |
| 3-8 | PF₈ | O | 1 | HEX |
| 3-9 | PF₁₀ | O | 1 | HEX |
| 3-10 | 2MB* | O | 1 | HEX |
| 3-11 | 4MH* | O | 1 | HEX |
| 3-12 | 1MH* | O | 1 | HEX |
| 3-13 | 2EOPr* | O | 1 | HEX |

TABLE 3-continued

Case of $A_2$ = Nt (2-2)

$$R-X-Nt-(CH_2)_n-O-\overset{CF_3}{\underset{|}{C^*H}}-R'$$

| No. | R | X | n | R' |
|---|---|---|---|---|
| 3-14 | 2POPr* | O | 1 | HEX |
| 3-15 | DEC | O | 1 | PEN |
| 3-16 | DEC | O | 1 | OCT |
| 3-17 | DEC | O | 1 | DEC |
| 3-18 | HEX | O | 1 | nPrOEt |
| 3-19 | HEP | O | 1 | nPrOEt |
| 3-20 | OCT | O | 1 | nPrOEt |
| 3-21 | NON | O | 1 | nPrOEt |
| 3-22 | DEC | O | 1 | nPrOEt |
| 3-23 | HEX | O | 1 | iPrOEt |
| 3-24 | HEP | O | 1 | iPrOEt |
| 3-25 | OCT | O | 1 | iPrOEt |
| 3-26 | NON | O | 1 | iPrOEt |
| 3-27 | DEC | O | 1 | iPrOEt |
| 3-28 | HEX | O | 1 | 2MB*OEt |
| 3-29 | HEP | O | 1 | 2MB*OEt |
| 3-30 | OCT | O | 1 | 2MB*OEt |
| 3-31 | NON | O | 1 | 2MB*OEt |
| 3-32 | DEC | O | 1 | 2MB*OEt |
| 3-33 | HEX | O | 0 | HEX |
| 3-34 | HEP | O | 0 | HEX |
| 3-35 | OCT | O | 0 | HEX |
| 3-36 | NON | O | 0 | HEX |
| 3-37 | DEC | O | 0 | HEX |
| 3-38 | UND | O | 0 | HEX |
| 3-39 | DOD | O | 0 | HEX |
| 3-40 | PF8 | O | 0 | HEX |
| 3-41 | PF10 | O | 0 | HEX |
| 3-42 | 2MB* | O | 0 | HEX |
| 3-43 | 4MH* | O | 0 | HEX |
| 3-44 | 1MH* | O | 0 | HEX |
| 3-45 | 2EOPr* | O | 0 | HEX |
| 3-46 | 2POPr* | O | 0 | HEX |
| 3-47 | DEC | O | 0 | PEN |
| 3-48 | DEC | O | 0 | OCT |
| 3-49 | DEC | O | 0 | DEC |
| 3-50 | HEX | O | 0 | nPrOEt |
| 3-51 | HEP | O | 0 | nPrOEt |
| 3-52 | OCT | O | 0 | nPrOEt |
| 3-53 | NON | O | 0 | nPrOEt |
| 3-54 | DEC | O | 0 | nPrOEt |
| 3-55 | HEX | O | 0 | iPrOEt |
| 3-56 | HEP | O | 0 | iPrOEt |
| 3-57 | OCT | O | 0 | iPrOEt |
| 3-58 | NON | O | 0 | iPrOEt |
| 3-59 | DEC | O | 0 | iPrOEt |
| 3-60 | HEX | O | 0 | 2MB*OEt |
| 3-61 | HEP | O | 0 | 2MB*OEt |
| 3-62 | OCT | O | 0 | 2MB*OEt |
| 3-63 | NON | O | 0 | 2MB*OEt |
| 3-64 | DEC | O | 0 | 2MB*OEt |

TABLE 4

Case of $A_2$ = Pym—Ph, Ph—Pym, n = 0 (2-3)

$$R-X-A_2-O-\overset{CF_3}{\underset{|}{C^*H}}-R'$$

| No. | R | X | $A_2$ | R' |
|---|---|---|---|---|
| 4-1 | HEP | O | Pym>-Ph | HEX |
| 4-2 | OCT | O | Pym>-Ph | HEX |
| 4-3 | NON | O | Pym>-Ph | HEX |
| 4-4 | DEC | O | Pym>-Ph | HEX |
| 4-5 | UND | O | Pym>-Ph | HEX |
| 4-6 | DOD | O | Pym>-Ph | HEX |
| 4-7 | HEP | — | Pym>-Ph | HEX |
| 4-8 | OCT | — | Pym>-Ph | HEX |
| 4-9 | NON | — | Pym>-Ph | HEX |
| 4-10 | DEC | — | Pym>-Ph | HEX |
| 4-11 | UND | — | Pym>-Ph | HEX |
| 4-12 | DOD | — | Pym>-Ph | HEX |
| 4-13 | DEC | O | Pym>-Ph | PEN |
| 4-14 | DEC | — | Pym>-Ph | PEN |
| 4-15 | DEC | O | Pym>-Ph | OCT |
| 4-16 | DEC | — | Pym>-Ph | OCT |
| 4-17 | DEC | O | Pym>-Ph | DEC |
| 4-18 | DEC | — | Pym>-Ph | DEC |
| 4-19 | PF8 | O | Pym>-Ph | HEX |
| 4-20 | PF10 | O | Pym>-Ph | HEX |
| 4-21 | 2MB* | O | Pym>-Ph | HEX |
| 4-22 | 1MB* | O | Pym>-Ph | HEX |
| 4-23 | 4MH* | O | Pym>-Ph | HEX |
| 4-24 | 3MP* | — | Pym>-Ph | HEX |
| 4-25 | 1MH* | O | Pym>-Ph | HEX |
| 4-26 | 2EOPr* | O | Pym>-Ph | HEX |
| 4-27 | 2EOPr* | O | Pym>-Ph | PEN |
| 4-28 | 2POPr* | O | Pym>-Ph | HEX |
| 4-29 | 2POPr* | O | Pym>-Ph | PEN |
| 4-30 | 2MB* | O | Pym>-Ph | PEN |
| 4-31 | 4MH* | O | Pym>-Ph | PEN |
| 4-32 | DEC | O | Pym>-PhF | HEX |
| 4-33 | DEC | — | Pym>-PhF | HEX |
| 4-34 | PF10 | O | Pym>-PhF | HEX |
| 4-35 | 2MB* | O | Pym>-PhF | HEX |
| 4-36 | 2MB* | — | Pym>-PhF | HEX |
| 4-37 | 2EOPr* | O | Pym>-PhF | HEX |
| 4-38 | 2EOPr* | — | Pym>-PhF | HEX |
| 4-39 | HEP | O | Ph-<Pym | HEX |
| 4-40 | OCT | O | Ph-<Pym | HEX |
| 4-41 | NON | O | Ph-<Pym | HEX |
| 4-42 | DEC | O | Ph-<Pym | HEX |
| 4-43 | UND | O | Ph-<Pym | HEX |
| 4-44 | DOD | O | Ph-<Pym | HEX |
| 4-45 | OCT | — | Ph-<Pym | HEX |
| 4-46 | NON | — | Ph-<Pym | HEX |
| 4-47 | DEC | — | Ph-<Pym | HEX |
| 4-48 | UND | — | Ph-<Pym | HEX |
| 4-49 | DOD | — | Ph-<Pym | HEX |
| 4-50 | DEC | O | Ph-<Pym | PEN |
| 4-51 | DEC | — | Ph-<Pym | PEN |
| 4-52 | DEC | O | Ph-<Pym | OCT |
| 4-53 | DEC | — | Ph-<Pym | OCT |
| 4-54 | DEC | O | Ph-<Pym | DEC |
| 4-55 | DEC | — | Ph-<Pym | DEC |
| 4-56 | PF8 | O | Ph-<Pym | HEX |
| 4-57 | PF10 | O | Ph-<Pym | HEX |
| 4-58 | 2MB* | O | Ph-<Pym | HEX |
| 4-59 | 2MB* | O | Ph-<Pym | PEN |
| 4-60 | 4MH* | O | Ph-<Pym | HEX |
| 4-61 | 4MH* | O | Ph-<Pym | PEN |
| 4-62 | 1MH* | O | Ph-<Pym | HEX |
| 4-63 | 2EOPr* | O | Ph-<Pym | HEX |
| 4-64 | 2EOPr* | O | Ph-<Pym | PEN |
| 4-65 | 2POPr* | O | Ph-<Pym | HEX |
| 4-66 | 2POPr* | O | Ph-<Pym | PEN |
| 4-67 | DEC | O | FPh-<Pym | HEX |
| 4-68 | PF10 | O | FPh-<Pym | HEX |
| 4-69 | 2MB* | O | FPh-<Pym | HEX |
| 4-70 | 2EOPr* | O | FPh-<Pym | HEX |
| 4-71 | HEP | O | Ph-Pym> | HEX |
| 4-72 | OCT | O | Ph-Pym> | HEX |
| 4-73 | NON | O | Ph-Pym> | HEX |
| 4-74 | DEC | O | Ph-Pym> | HEX |
| 4-75 | UND | O | Ph-Pym> | HEX |
| 4-76 | DOD | O | Ph-Pym> | HEX |
| 4-77 | OCT | O | Ph-Pym> | HEX |
| 4-78 | NON | — | Ph-Pym> | HEX |
| 4-79 | DEC | — | Ph-Pym> | HEX |
| 4-80 | UND | — | Ph-Pym> | HEX |
| 4-81 | DOD | — | Ph-Pym> | HEX |
| 4-82 | DEC | O | Ph-Pym> | PEN |
| 4-83 | DEC | — | Ph-Pym> | PEN |
| 4-84 | DEC | O | Ph-Pym> | OCT |
| 4-85 | DEC | — | Ph-Pym> | OCT |
| 4-86 | DEC | O | Ph-Pym> | DEC |
| 4-87 | DEC | — | Ph-Pym> | DEC |
| 4-88 | PF8 | O | Ph-Pym> | HEX |
| 4-89 | PF10 | O | Ph-Pym> | HEX |
| 4-90 | 2MB* | O | Ph-Pym> | HEX |
| 4-91 | 2MB* | O | Ph-Pym> | PEN |
| 4-92 | 4MH* | O | Ph-Pym> | HEX |
| 4-93 | 4MH* | O | Ph-Pym> | PEN |

TABLE 4-continued

Case of $A_2$ = Pym—Ph, Ph—Pym, n = 0  (2-3)

$$R-X-A_2-O-\underset{|}{\overset{CF_3}{C^*H}}-R'$$

| No. | R | X | $A_2$ | R' |
|---|---|---|---|---|
| 4-94 | 1MH* | O | Ph-Pym> | HEX |
| 4-95 | 2EOPr* | O | Ph-Pym> | HEX |
| 4-96 | 2EOPr* | O | Ph-Pym> | PEN |
| 4-97 | 2POPr* | O | Ph-Pym> | HEX |
| 4-98 | 2POPr* | O | Ph-Pym> | PEN |

TABLE 5-1

Case of $A_2 = A_4-C\#C-A_5$, n = 0  (2-4-1)

$$R-X-A_4-C\#C-A_5-O-\underset{|}{\overset{CF_3}{C^*H}}-R'$$

| No. | R | X | $A_4$ | $A_5$ | R' |
|---|---|---|---|---|---|
| 5-1 | HEP | O | Ph | Ph | HEX |
| 5-2 | OCT | O | Ph | Ph | HEX |
| 5-3 | NON | O | Ph | Ph | HEX |
| 5-4 | DEC | O | Ph | Ph | HEX |
| 5-5 | UND | O | Ph | Ph | HEX |
| 5-6 | DOD | O | Ph | Ph | HEX |
| 5-7 | HEP | — | Ph | Ph | HEX |
| 5-8 | OCT | — | Ph | Ph | HEX |
| 5-9 | NON | — | Ph | Ph | HEX |
| 5-10 | DEC | — | Ph | Ph | HEX |
| 5-11 | UND | — | Ph | Ph | HEX |
| 5-12 | DOD | — | Ph | Ph | HEX |
| 5-13 | DEC | O | Ph | Ph | PEN |
| 5-14 | DEC | — | Ph | Ph | PEN |
| 5-15 | DEC | O | Ph | Ph | OCT |
| 5-16 | DEC | — | Ph | Ph | OCT |
| 5-17 | DEC | O | Ph | Ph | DEC |
| 5-18 | DEC | — | Ph | Ph | DEC |
| 5-19 | $PF_8$ | O | Ph | Ph | HEX |
| 5-20 | $PF_{10}$ | O | Ph | Ph | HEX |
| 5-21 | 2MB* | O | Ph | Ph | HEX |
| 5-22 | 2MB* | — | Ph | Ph | HEX |
| 5-23 | 4MH* | O | Ph | Ph | HEX |
| 5-24 | 4MH* | — | Ph | Ph | HEX |
| 5-25 | 1MH* | O | Ph | Ph | HEX |
| 5-26 | 2EOPr* | O | Ph | Ph | HEX |
| 5-27 | 2EOPr* | — | Ph | Ph | HEX |
| 5-28 | 2POPr* | O | Ph | Ph | HEX |
| 5-29 | 2POPr* | — | Ph | Ph | HEX |
| 5-30 | DEC | O | Ph | Ph | nPrOEt |
| 5-31 | DEC | — | Ph | Ph | nPrOEt |
| 5-32 | DEC | O | Ph | Ph | iPrOEt |
| 5-33 | DEC | — | Ph | Ph | iPrOEt |
| 5-34 | DEC | O | Ph | Ph | 2MB*OMe |
| 5-35 | DEC | — | Ph | Ph | 2MB*OMe |
| 5-36 | OCT | O | Ph | Ph | 2MB*OMe |
| 5-37 | OCT | — | Ph | Ph | 2MB*OMe |
| 5-38 | NON | O | Ph | Ph | 2MB*OMe |
| 5-39 | NON | — | Ph | Ph | 2MB*OMe |
| 5-40 | DEC | O | Ph | Ph | 2MB*OMe |
| 5-41 | DEC | — | Ph | Ph | 2MB*OMe |
| 5-42 | DEC | O | Ph | Ph | iPrOPr |
| 5-43 | DEC | — | Ph | Ph | iPrOPr |
| 5-44 | DEC | O | Ph | Ph | 2MB*OPr |
| 5-45 | DEC | — | Ph | Ph | 2MB*OPr |
| 5-46 | DEC | O | Ph | PhF | HEX |
| 5-47 | DEC | — | Ph | PhF | HEX |
| 5-48 | $PF_{10}$ | O | Ph | PhF | HEX |
| 5-49 | 2MB* | O | Ph | PhF | HEX |
| 5-50 | 2MB* | — | Ph | PhF | HEX |
| 5-51 | 2EOPr* | O | Ph | PhF | HEX |
| 5-52 | 2EOPr* | — | Ph | PhF | HEX |
| 5-53 | DEC | O | Ph | PhF | 2MB*OPr |
| 5-54 | DEC | — | Ph | PhF | 2MB*OPr |
| 5-55 | DEC | O | Ph | PhF | 2MB*OEt |
| 5-56 | DEC | — | Ph | PhF | 2MB*OEt |
| 5-57 | DEC | O | FPh | Ph | HEX |
| 5-58 | $PF_{10}$ | O | FPh | Ph | HEX |
| 5-59 | 2MB* | O | FPh | Ph | HEX |
| 5-60 | 2EOPr* | O | FPh | Ph | HEX |
| 5-61 | DEC | O | FPh | Ph | iPrOEt |
| 5-62 | DEC | O | FPh | Ph | 2MB*OEt |
| 5-63 | DEC | O | FPh | PhF | HEX |
| 5-64 | $PF_{10}$ | O | FPh | PhF | HEX |
| 5-65 | 2MB* | O | FPh | PhF | HEX |
| 5-66 | 2EOPr* | O | FPh | Ph | 2MB*OEt |
| 5-67 | DEC | — | Fph | PhF | iPrOEt |
| 5-68 | DEC | O | Fph | PhF | 2MB*OEt |

TABLE 5-2

Case of $A_2 = A_4-C\#C-A_5$, n = 1  (2-4-2)

$$R-X-A_4-C\#C-A_5-CH_2-O-\underset{|}{\overset{CF_3}{C^*H}}-R'$$

| No. | R, X, $A_4$, $A_5$ and R' |
|---|---|
| No. 5-1' to No. 5-68' | having the same R, X, $A_4$, $A_5$ and R' as No. 5-1 to N. 5-68, respectively. |

TABLE 5-3

Case of $A_2 = A_4-CH_2CH_2-A_5$, n = 0  (2-4-3)

$$R-X-A_4-CH_2CH_2-A_5-O-\underset{|}{\overset{CF_3}{C^*H}}-R'$$

| No. | R, X, $A_4$, $A_5$ and R' |
|---|---|
| No. 5-1'' to No. 5-68'' | having the same R, X, $A_4$, $A_5$ and R' as No. 5-1 to No. 5-68, respectively. |

TABLE 5-4

Case of $A_2 = Bp-C\#C-A_5$,  (2-4-4)

$$R-X-Bp-C\#C-A_5-(CH_2)_n-O-\underset{|}{\overset{CF_3}{C^*H}}-R'$$

| No. | R | X | $A_5$ | n | R' |
|---|---|---|---|---|---|
| 5-69 | HEX | O | Ph | 0 | HEX |
| 5-70 | HEX | — | Ph | 0 | HEX |
| 5-71 | HEP | O | Ph | 0 | HEX |
| 5-72 | HEP | — | Ph | 0 | HEX |
| 5-73 | OCT | O | Ph | 0 | HEX |
| 5-74 | OCT | — | Ph | 0 | HEX |
| 5-75 | 2MB* | O | Ph | 0 | HEX |
| 5-76 | HEX | O | Ph | 1 | HEX |
| 5-77 | HEX | — | Ph | 1 | HEX |
| 5-78 | HEX | O | PhF | 0 | HEX |
| 5-79 | HEX | — | PhF | 0 | HEX |
| 5-80 | HEX | O | PhF | 1 | HEX |
| 5-81 | HEX | — | PhF | 1 | HEX |

TABLE 5-5

Case of $A_2 = Bp-CH_2CH_2-A_5$  (2-4-5)

$$R-X-Bp-CH_2CH_2-A_5-(CH_2)_n-O-\underset{|}{\overset{CF_3}{C^*H}}-R'$$

| No. | R | X | $A_5$ | n | R' |
|---|---|---|---|---|---|
| 5-82 | HEX | O | Ph | 0 | HEX |
| 5-83 | HEX | — | Ph | 0 | HEX |
| 5-84 | HEP | O | Ph | 0 | HEX |
| 5-85 | HEP | — | Ph | 0 | HEX |
| 5-86 | OCT | O | Ph | 0 | HEX |
| 5-87 | OCT | — | Ph | 0 | HEX |
| 5-88 | 2MB* | O | Ph | 0 | HEX |
| 5-89 | HEX | O | PhF | 0 | HEX |
| 5-90 | HEX | — | PhF | 0 | HEX |

TABLE 6-1

Case of $A_2 = A_1-Y_2-<Pyr$, $n = 1$     (2-5-1)

$$R-X-A_1-Y_2-<Pyr-CH_2-O-\overset{CF_3}{\underset{|}{C^*H}}-R'$$

| No. | R | X | $A_1$ | $Y_2$ | R' |
|---|---|---|---|---|---|
| 6-1 | OCT | O | Ph | C#C | PEN |
| 6-2 | NON | O | Ph | C#C | PEN |
| 6-3 | DEC | O | Ph | C#C | PEN |
| 6-4 | OCT | O | Ph | C#C | HEX |
| 6-5 | NON | O | Ph | C#C | HEX |
| 6-6 | DEC | O | Ph | C#C | HEX |
| 6-7 | OCT | O | Ph | C#C | OCT |
| 6-8 | NON | O | Ph | C#C | OCT |
| 6-9 | DEC | O | Ph | C#C | OCT |
| 6-10 | OCT | O | Ph | C#C | DEC |
| 6-11 | NON | O | Ph | C#C | DEC |
| 6-12 | DEC | O | Ph | C#C | DEC |
| 6-13 | OCT | — | Ph | C#C | PEN |
| 6-14 | NON | — | Ph | C#C | PEN |
| 6-15 | DEC | — | Ph | C#C | PEN |
| 6-16 | OCT | — | Ph | C#C | HEX |
| 6-17 | NON | — | Ph | C#C | HEX |
| 6-18 | DEC | — | Ph | C#C | HEX |
| 6-19 | OCT | — | Ph | C#C | OCT |
| 6-20 | NON | — | Ph | C#C | OCT |
| 6-21 | DEC | — | Ph | C#C | OCT |
| 6-22 | OCT | — | Ph | C#C | DEC |
| 6-23 | NON | — | Ph | C#C | DEC |
| 6-24 | DEC | — | Ph | C#C | DEC |
| 6-25 | DEC | O | Ph | Ete | HEX |
| 6-26 | DEC | — | Ph | Ete | HEX |
| 6-27 | DEC | O | Ph | C#C | iPrOEt |
| 6-28 | DEC | — | Ph | C#C | iPrOEt |
| 6-29 | DEC | O | Ph | Ete | iPrOEt |
| 6-30 | DEC | — | Ph | Ete | iPrOEt |
| 6-31 | 2MB | O | Ph | C#C | HEX |
| 6-32 | 4MH | O | Ph | C#C | HEX |
| 6-33 | 2MB | O | Ph | Ete | HEX |
| 6-34 | 4MH | O | Ph | Ete | HEX |
| 6-35 | 4MH | O | Ph | C#C | iPrOEt |
| 6-36 | 4MH | O | Ph | Ete | iPrOEt |
| 6-37 | DEC | O | Ph | C#C | EOCM |
| 6-38 | DEC | O | Ph | Ete | EOCM |
| 6-39 | DEC | — | Ph | C#C | EOCM |
| 6-40 | DEC | — | Ph | Ete | EOCM |
| 6-41 | 4MH | O | Ph | C#C | EOCM |
| 6-42 | 4MH | O | Ph | Ete | EOCM |
| 6-43 | 2EOPr* | O | Ph | C#C | HEX |
| 6-44 | 2EOPr* | O | Ph | Ete | HEX |
| 6-45 | 2EOPr* | O | Ph | C#C | iPrOEt |
| 6-46 | 2EOPr* | O | Ph | Ete | iPrOEt |
| 6-47 | 2EOPr* | O | Ph | C#C | EOCM |
| 6-48 | 2EOPr* | O | Ph | Ete | EOCM |
| 6-49 | $PF_{10}$ | O | Ph | C#C | HEX |
| 6-50 | $PF_{10}$ | O | Ph | C#C | iPrOEt |
| 6-51 | $PF_{10}$ | O | Ph | C#C | EOCM |
| 6-52 | HEX | O | Bp | C#C | HEX |
| 6-53 | HEX | O | Bp | Ete | HEX |
| 6-54 | HEX | O | Bp | C#C | iPrOEt |
| 6-55 | HEX | O | Bp | Ete | iPrOEt |
| 6-56 | HEX | O | Bp | C#C | EOCM |
| 6-57 | HEX | O | Bp | Ete | EOCM |
| 6-58 | 4MH | O | Bp | C#C | HEX |
| 6-59 | 4MH | O | Bp | C#C | EOCM |
| 6-60 | 2EOPr* | O | Bp | C#C | HEX |
| 6-61 | HEX | O | Nt | C#C | HEX |
| 6-62 | KEX | O | Nt | Ete | HEX |
| 6-63 | HEX | O | Nt | C#C | iPrOEt |
| 6-64 | HEX | O | Nt | Ete | iPrOEt |
| 6-65 | HEX | O | Nt | C#C | EOCM |
| 6-66 | HEX | O | Nt | Ete | EOCM |
| 6-67 | 4MH | O | Nt | C#C | HEX |
| 6-68 | 4MH | O | Nt | C#C | EOCM |

TABLE 6-2

Case of $A_2 = A_1-Y_2-<Pyr$, $n = 0$     (2-5-2)

$$R-X-A_1-Y_2-<Pyr-O-\overset{CF_3}{\underset{|}{C^*H}}-R'$$

| No. | R, X, $A_1$, $Y_2$ and R' |
|---|---|
| No. 6-1' to No. 6-68' | having the same R, X, $A_1$, $Y_2$ and R' as No. 6-1 to No. 6-68, respectively. |

TABLE 7

Case of $A_3$ is Nt     (3-1)

$$R-X-Nt-COO-\overset{CF_3}{\underset{|}{C^*H}}-R'$$

| No. | R, X and R' |
|---|---|
| No. 7-1 to No. 7-32 | having the same R, X and R' as No. 3-1 to No. 3-32, respectively. |

TABLE 8-1

Case of $A_3 = Ph-CH_2CH_2-Ph$     (3-2-1)

$$R-X-Ph-CH_2CH_2-Ph-COO-\overset{CF_3}{\underset{|}{C^*H}}-R'$$

| No. | R | X | R' |
|---|---|---|---|
| 8-1 | OCT | O | PEN |
| 8-2 | OCT | O | HEX |
| 8-3 | OCT | O | OCT |
| 8-4 | OCT | O | DEC |
| 8-5 | OCT | — | PEN |
| 8-6 | OCT | — | HEX |
| 8-7 | OCT | — | OCT |
| 8-8 | OCT | — | DEC |
| 8-9 | NON | O | PEN |
| 8-10 | NON | O | HEX |
| 8-11 | NON | O | OCT |
| 8-12 | NON | O | DEC |
| 8-13 | NON | — | PEN |
| 8-14 | NON | — | HEX |
| 8-15 | NON | — | OCT |
| 8-16 | NON | — | DEC |
| 8-17 | DEC | O | PEN |
| 8-18 | DEC | O | HEX |
| 8-19 | DEC | O | OCT |
| 8-20 | DEC | O | DEC |
| 8-21 | DEC | — | PEN |
| 8-22 | DEC | — | HEX |
| 8-23 | DEC | — | OCT |
| 8-24 | DEC | — | DEC |
| 8-25 | $PF_{10}$ | O | HEX |
| 8-26 | 2MB* | O | HEX |
| 8-27 | 4MH* | O | HEX |
| 8-28 | 2EOPr* | O | HEX |
| 8-29 | DEC | O | EOCM |
| 8-30 | DEC | — | EOCM |
| 8-31 | DEC | O | iPrOEt |
| 8-32 | DEC | — | iPrOEt |

TABLE 8-2

Case of $A_3 = Ph-CH_2CH_2-PhF$     (3-2-2)

$$R-X-Ph-CH_2CH_2-PhF-COO-\overset{CF_3}{\underset{|}{C^*H}}-R'$$

| No. | R, X and R' |
|---|---|
| No. 8-1' to No. 8-32' | having the same R, X and R' as No. 8-1 to No. 8-32, respectively. |

TABLE 8-3

Case of $A_3 = Ph-CH_2CH_2-Bp$     (3-2-3)

$$R-X-Ph-CH_2CH_2-Bp-COO-\underset{\underset{C^*H-R'}{|}}{CF_3}$$

| No. | R | X | R' |
|---|---|---|---|
| 8-33 | PEN | O | PEN |
| 8-34 | PEN | O | HEX |
| 8-35 | HEX | O | PEN |
| 8-36 | HEX | O | HEX |
| 8-37 | 2MB | O | HEX |
| 8-38 | 4MH | O | HEX |
| 8-39 | 2EOPr* | O | HEX |
| 8-40 | HEX | O | EOCM |
| 8-41 | HEX | O | iPyOEt |
| 8-42 | PEN | — | PEN |
| 8-43 | PEN | — | HEX |
| 8-44 | HEX | — | PEN |
| 8-45 | HEX | — | HEX |
| 8-46 | HEX | — | EOCM |
| 8-47 | HEX | — | iPrOEt |

TABLE 8-4

Case of $A_3 = FPh-CH_2CH_2-Bp$     (3-2-4)

$$R-X-FPh-CH_2CH_2-Bp-COO-\underset{\underset{C^*H-R'}{|}}{CF_3}$$

| No. | R, X and R' |
|---|---|
| No. 8-33' to No. 8-41' | having the same R, X and R' as No. 8-33 to No. 8-41, respectively. |

TABLE 8-5

Case of $A_3 = Bp-CH_2CH_2-Ph$     (3-2-5)

$$R-X-Bp-CH_2CH_2-Ph-COO-\underset{\underset{C^*H-R'}{|}}{CF_3}$$

| No. | R, X and R' |
|---|---|
| No. 8-33'' to No. 8-41'' | having the same R, X and R' as No. 8-33 to No. 8-41, respectively. |

TABLE 8-6

Case of $A_3 = Bp-CH_2CH_2-PhF$     (3-2-6)

$$R-X-Bp-CH_2CH_2-PhF-COO-\underset{\underset{C^*H-R'}{|}}{CF_3}$$

| No. | R, X and R' |
|---|---|
| No. 8-33''' to No. 8-41''' | having the same R, X and R' as No. 8-33 to No. 8-41, respectively. |

TABLE 8-7

Case of $A_3 = Nt-CH_2CH_2-Ph$     (3-2-7)

$$R-X-Nt-CH_2CH_2-Ph-COO-\underset{\underset{C^*H-R'}{|}}{CF_3}$$

| No. | R, X and R' |
|---|---|
| No. 8-33'''' to No. 8-41'''' | having the same R, X and R' as No. 8-33 to No. 8-41, respectively. |

TABLE 8-8

Case of $A_3 = Nt-CH_2CH_2-Ph$     (3-2-8)

$$R-X-Nt-CH_2CH_2-Ph-COO-\underset{\underset{C^*H-R'}{|}}{CF_3}$$

| No. | R, X and R' |
|---|---|
| No. 8-33''''' to No. 8-41''''' | having the same R, X and R' as No. 8-33 to No. 8-41, respectively. |

TABLE 9

Case of $A_3 = A_1-Y_2-<Pyr$     (3-3)

$$R-X-A_1-Y_2-<Pyr-COO-\underset{\underset{C^*H-R'}{|}}{CF_3}$$

| No. | R, X, $A_1$, $Y_2$ and R' |
|---|---|
| No. 9-1 to No. 9-68 | having the same R, X, $A_1$, $Y_2$ and R' as No. 6-1 to No. 6-68, respectively. |

[A] Compounds of the formula (1) of this invention can be produced in accordance with the following reactions.

[I] In case of $R=CH_3$, $m=0$ and $Y_1=O$

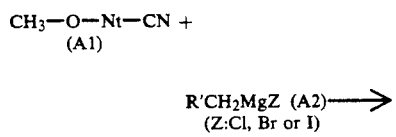

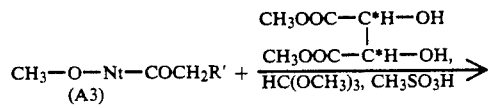

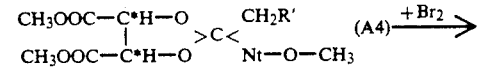

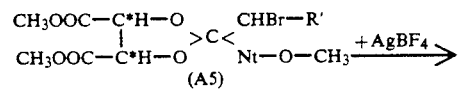

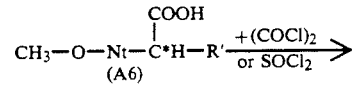

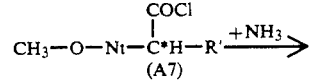

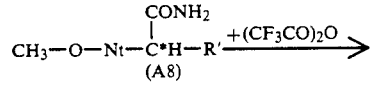

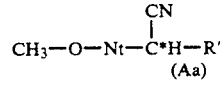

[II] In case of $m=0$ and $Y_1=O$

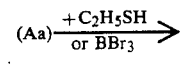

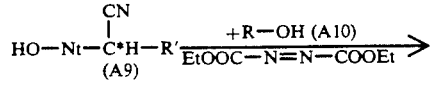

[III] In case of $m=0$ and $Y_1=COO$

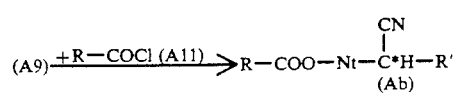

[IV] In case of m=1, $A_1$=Ph and $Y_1$=$CH_2O$

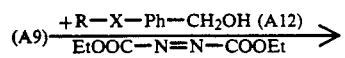

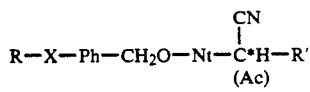

[V] In case of m=1, $A_1$=Ph (including F-substituted Ph) and $Y_1$=COO

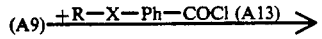

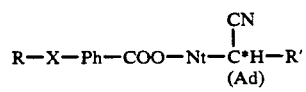

[VI] In case of m=1, $A_1$=Ph (including F-substituted Ph) and $Y_1$=C#C

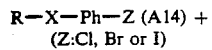

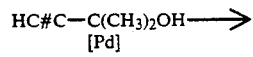

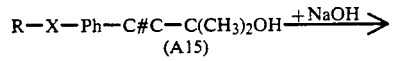

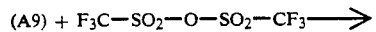

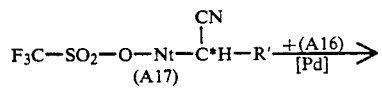

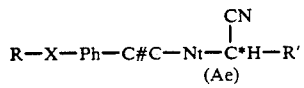

[VII] In case of m=1, $A_1$=<Pyr and $Y_1$=$CH_2O$

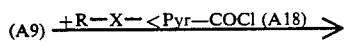

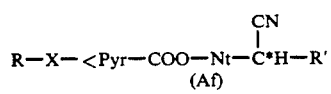

These reactions can be carried out as follows.

[I] (A1) is alkylated by reaction with (A2), such as methyl magnesium iodide, and then reacted with optically active dimethyl tartrate, methane sulfonic acid and trimethyl ortho-formate to obtain (A4). (A4) is brominated with $Br_2$, followed by reacting silver tetrafluoroborate therewith to obtain (A6). (A6) is reacted with oxalyl chloride or thionyl chloride to derive an acid chloride (A7), which is then reacted with ammonia to obtain an amide (A8), followed by dehydrating (A8) with trifluoroacetic anhydride to obtain a compound of this invention represented by the formula (Aa).

[II] (A9) is produced by reacting (Aa) with ethane thiol or boron tribromide to remove the methyl group.

(A9) is etherified with (A10), such as n-decyl alcohol, and diethylazodicarboxylate to obtain a compound of this invention represented by the formula (Aa').

[III] (A9) is esterified with an acid halide (A11), such as enanthyl chloride, to obtain a compound of this invention represented by the formula (Ab).

[IV] (A9) is etherified with (A12), such as p-hexyloxybenzyl alcohol, to obtain a compound of this invention represented by the formula (Ac).

[V] (A9) is esterified with (A13), such as 4-decyloxy-3-fluoro-benzoyl chloride, to obtain a compound of this invention represented by the formula (Ad).

[VI] (A14), such as 4-decyloxy-3-fluoro-iodobenzene, is reacted with 3-methyl-1-butyne-3-ol to obtain (A15), followed by reacting (A15) with sodium hydroxide to obtain (A16).

(A9) is reacted with trifluoromethanesulfonic anhydride to obtain (A17), followed by reacting (A16) therewith to obtain a compound of this invention represented by the formula (Ae).

[VII] (A9) is esterified with (A18), such as 2-decyloxy-nicotinyl chloride, to obtain a compound of this invention represented by the formula (Af).

[B] Compounds of the formula (2), wherein $A_2$ is Bp, of this invention can be produced in accordance with the following reactions. (Hereinafter, Z,Z':Cl, Br or I; Z":Br or I; M:Li, Na or K; Me:methyl; Et;ethyl; R":alkyl)

[I] In case of $A_2$=Ph-Ph and n=0

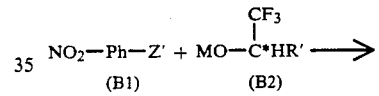

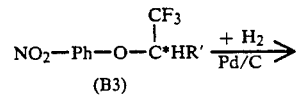

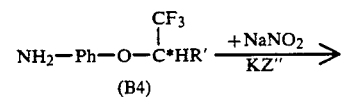

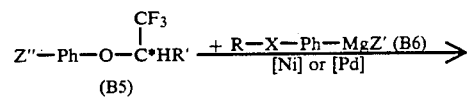

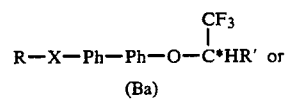

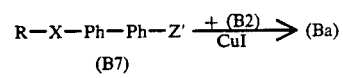

[II] In case of $A_2$=Ph-PhF and n=0

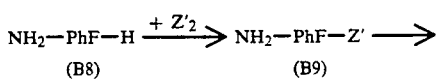

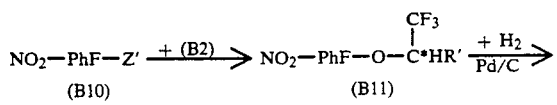

-continued

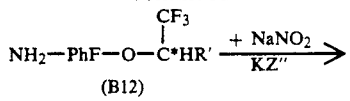
(B12)

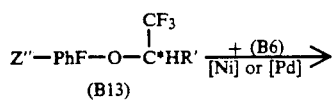
(B13)

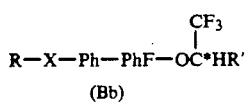
(Bb)

[III] In case of $A_2 = Ph\text{-}Ph$ and $n = 1$

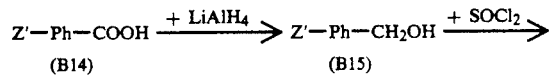
(B14)  (B15)

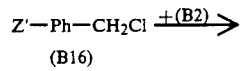
(B16)

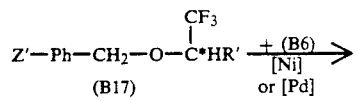
(B17)

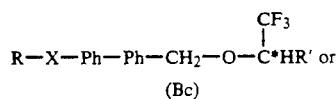
(Bc)

$$R-X-Ph-Ph-COOH + LiAlH_4 \longrightarrow$$
(B18)

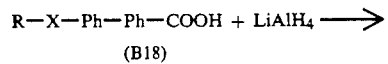
(B19)

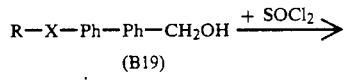 (Bc)
(B20)

[IV] In case of $A_2 = Ph\text{-}PhF$ and $n = 1$

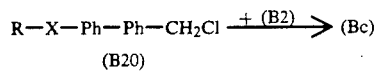
(B21)

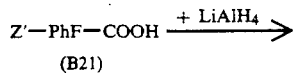
(B22)  (B23)

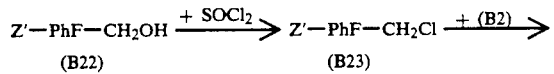
(B24)

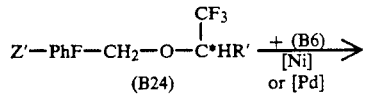
(Bd)

These reactions can be carried out as follows.

[I] (B1) and (B2) are heated in an anhydrous solvent, such as anhydrous dimethylformamide, dimethyl sulfoxide or tetrahydrofuran (hereinafter referred to as DMF, DMSO and THF, respectively), to obtain (B3), followed by reducing (B3) with hydrogen under Pd/C catalyst to obtain (B4). (B4) is diazotized with $NaNO_2$, followed by reacting an alkali metal halide therewith to obtain (B5). (B5) and (B6) are reacted in an anhydrous solvent, such as anhydrous ether or THF, under an atmosphere of an inert gas, such as nitrogen, in the presence of catalyst, such as zero- or bi-valent nickel catalyst, or zero- or bi-valent palladium catalyst, to obtain a compound of this invention represented by the formula (Ba).

The compound (Ba) may also be produced by heating (B7) and (B2) under reflux in anhydrous DMF in the presence of cuprous iodide.

[II] Meta-fluoro-aniline (B8) is halogenized to obtain (B9), followed by oxidizing the amino group to form (B10). (B10) and (B2) are heated in an anhydrous solvent, such as anhydrous DMF, DMSO or THF, to obtain (B11), followed by reducing (B11) with hydrogen under Pd/C catalyst to obtain (B12). (B12) is diazotized with $NaNO_2$, followed by reacting an alkali metal halide therewith to obtain (B13). (B13) and (B6) are reacted in an anhydrous solvent, such as anhydrous ether or THF, under an atmosphere of an inert gas (such as nitrogen), in the presence of catalyst, such as zero- or bi-valent nickel catalyst, or zero- or bi-valent palladium catalyst, to obtain a compound of this invention represented by the formula (Bb).

[III] (B14) is reduced with lithium aluminum hydride in an anhydrous solvent, such as anhydrous ether or THF, to obtain (B15), followed by halogenating the OH group thereof with a halogenating reagent (such as thionyl chloride) to obtain (B16). (B16) and (B2) are reacted in an anhydrous solvent, such as anhydrous DMF or DMSO, at room temperature or under heating to produce (B17), followed by reacting (B6) therewith in an anhydrous solvent, such as anhydrous ether or THF), under an atmosphere of an inert gas, in the presence of catalyst, such as zero- or bi-valent nickel catalyst, or zero- or bi-valent palladium catalyst, to obtain a compound of this invention represented by the formula (Bc).

The compound (Bc) may also be produced by reducing (B18) with lithium aluminum hydride in an anhydrous solvent, such as anhydrous ether or THF, to obtain (B19), followed by halogenating the OH group thereof with a halogenating reagent (such as thionyl chloride) to obtain (B20) and then reacting (B20) with (B2) in an anhydrous solvent, such as anhydrous DMF or DMSO, at room temperature or under heating.

[IV] (B21) is reduced with lithium aluminum hydride in an anhydrous solvent, such as anhydrous ether or THF, to obtain (B22), followed by halogenating the OH group thereof with a halogenating reagent, such as thionyl chloride, to obtain (B23). (B23) and (B2) are reacted in an anhydrous solvent, such as anhydrous DMF or DMSO, at room temperature or under heating to produce (B24), followed by reacting (B6) therewith in an anhydrous solvent, such as anhydrous ether or THF, under an atmosphere of an inert gas, in the presence of catalyst, such as zero- or bivalent nickel catalyst, or zero- or bivalent palladium catalyst, to obtain a compound of this invention represented by the formula (Bd).

(B2), the raw materials of the above compounds, can be produced in accordance with the following reactions.

[V] In case of R' free from oxygen atom

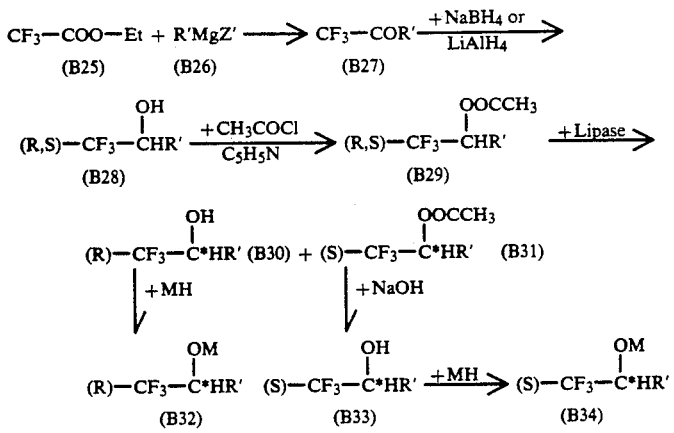

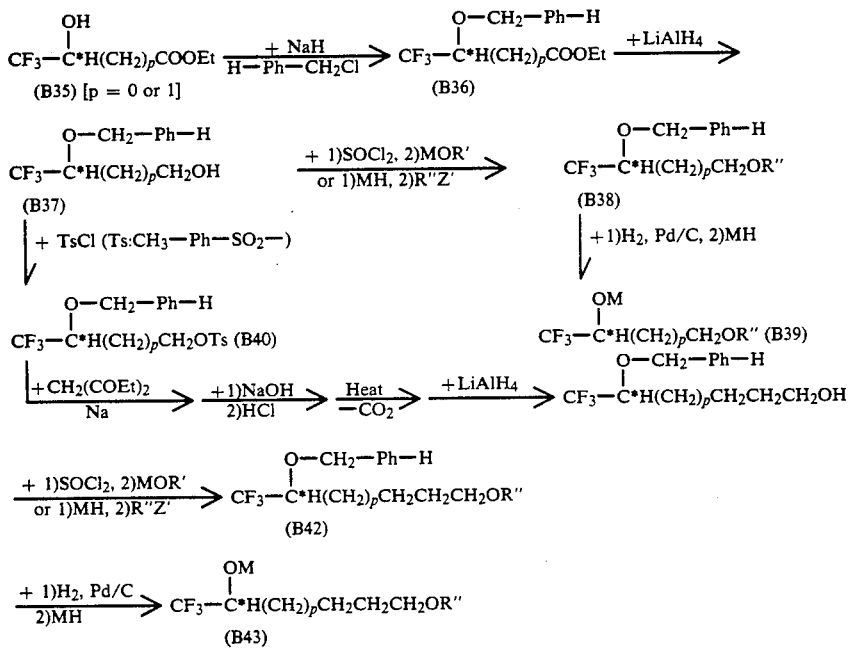

[VI] In case of R' containing oxygen atom

These reactions can be carried out as follows.

[V] In case of R' free from oxygen atom, (B27), obtained by reacting ethyl trifluoroacetate with a Grignard's reagent at a temperature below −20° C., is reduced with sodium borohydride or lithium aluminumhydride to obtain racemic compounds (B28). Racemic esters (B29), obtained by reacting (B28) with an acid chloride, such as acetyl chloride, are asymmetrically hydrolyzed in an aqueous solution using lipase and then isolated, followed by reacting therewith an alkali metal hydride, such as sodium hydride, to obtain a metal salt of optically active alcohol (B32) as a raw material for the compounds of this invention. On the other hand, unreacted ester (B31), recovered unreacted in asymmetric hydrolysis, is chemically hydrolyzed to obtain another optically active alcohol (B33) of reverse steric configuration, which can also similarly converted into a metal salt (B34) and used as a raw material for the compounds of this invention.

[VI] In case of R' containing oxygen atom, OH group of (B35) is benzyl-etherified into (B36), followed by reducing it with lithium aluminum hydride to obtain (B37). (B38) is prepared by halogenating (B37) with a halogenating agent, such as thionyl chloride), and then reacting therewith an alkali metal alkoxide, or by changing (B37) into an alkoxide with an alkali metal hydride and then reacting it with an alkyl halide. After hydrogenolysis of (B38), followed by reaction with an alkali metal hydride, such as sodium hydride, there can be obtained a metal salt (B39) usable as a raw material for the compounds of the invention.

Optically active compounds (B35) can be obtained by known methods, such as those written in "Oil Chemistry", No. 35, p. 608–613, and Preprint of "The 13th Fluorochemistry Discussion", 4D113.

Optically active sites of R, R' and R" in the above and also hereinafter can be derived, respectively, from the corresponding oa alcohols or oa carboxylic acids. Those oa alcohols and/or oa carboxylic acids are commercially available, or can be prepared by asymmetric reduction of the corresponding ketones with enzymes, microorganisms or asymmetric metal catalysts, or derived from naturally occurring oa compounds (such as oa amino acids, oa hydroxy acids and esters thereof), or synthetic oa compounds (such as oa 2-fluoroalkyl alcohols, 2-chloroalkyl alcohols and oa epoxy compounds).

[C] Compounds of the formula (2), wherein $A_2$ is Nt, of this invention can be produced in accordance with the following reactions. (Z,Z':Cl, Br or I; Z":Br or I; M:Li, Na or K; Et:ethyl; R":alkyl)

[I] In case of $A_2$ is Nt and n=1

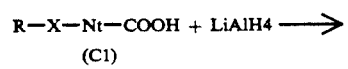
(C1)

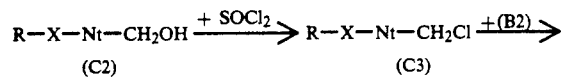
(C2) (C3)

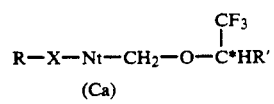
(Ca)

(C1) is reduced with lithium aluminum hydride to obtain (C2), followed by halogenating the OH group with a halogenating reagent, such as thionyl chloride, to obtain (C3). (C16) and (B2) are reacted in anhydrous DMF or DMSO at room temperature or under heating to obtain a compound of the invention represented by the formula (Ca).

[II] In case of $A_2$ is Nt and n=0

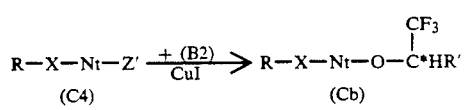
(C4) (Cb)

A compound of the invention represented by (Cb) can be produced by heating (C4) and (B2) under reflux in anhydrous DMF in the presence of cuprous iodide.

[D] Compounds of the formula (2), wherein $A_2$=-Pym-Ph or Ph-Pym and n=0, can be produced in accordance with the following reactions.

[I] In case of $A_2$ is Pym>-Ph

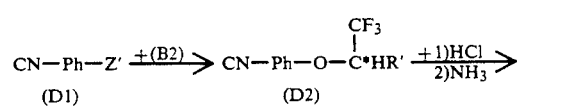
(D1) (D2)

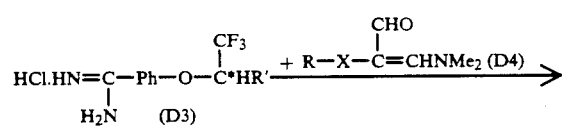

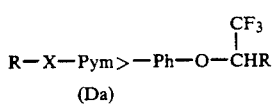
(Da)

[II] In case of $A_2$ is Pym>-PhF

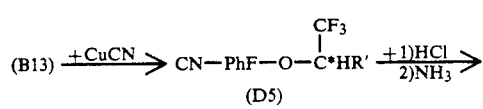
(D5)

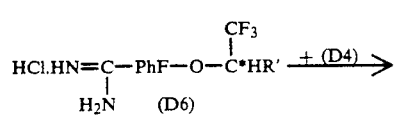

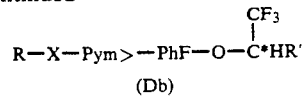
(Db)

[III] In case of $A_2$ is FPh-<Pym

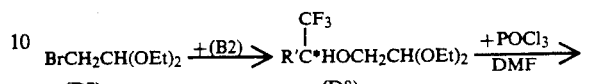
(D7) (D8)

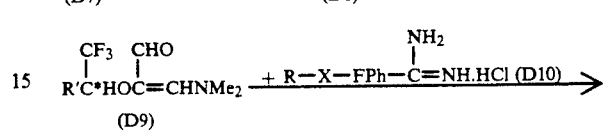
(D9)

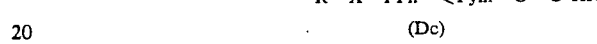
(Dc)

[IV] In case of $A_2$ is Ph-Pym>

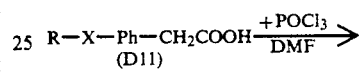
(D11)

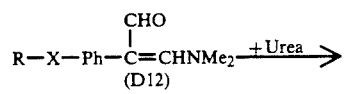
(D12)

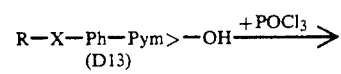
(D13)

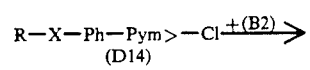
(D14)

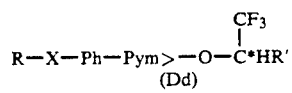
(Dd)

These reactions can be carried out as follows.

[I] (B2), as mentioned above [B], is reacted with (D1) in an anhydrous solvent (such as anhydrous DMF, DMSO or THF) under heating to obtain (D2). (D2) is reacted in dry ethanol with gaseous hydrogen chloride and then reacted with gaseous ammonia to obtain (D3). (D3) and (D4) are heated in ethanol or methanol in the presence of a base (such as sodium metal) under reflux to obtain a compound of this invention represented by the formula (Da).

[II] (B13), as mentioned above [B], is reacted with cuprous cyanide in DMF to obtain (D5). (D5) is reacted in dry ethanol with gaseous hydrogen chloride and then reacted with gaseous ammonia to obtain (D6). (D6) and (D4) are heated in ethanol or methanol in the presence of a base (such as sodium metal) under reflux to obtain a compound of this invention represented by the formula (Db).

[III] (B2) is reacted with bromo-acetoaldehyde diethyl acetal in an anhydrous solvent (such as anhydrous DMF, DMSO or THF) under heating to obtain (D8), which is then reacted with a Wilsmeier reagent (such as reaction products of phosphorus oxychloride with DMF) to produce (D9). (D9) and (D10) are heated in ethanol or methanol in the presence of a base (such as sodium metal) under reflux to obtain a compound of this invention represented by the formula (Dc).

[IV] (D11) is reacted With a Vilsmeier reagent (such as reaction products of phosphorus oxychloride with DMF) to produce (D12). (D12) is reacted with urea and then with phosphorus oxychloride to obtain (D14). (D14) and (B2) are reacted in an anhydrous solvent (such as anhydrous DMF, DMSO or THF) under heating to obtain a compound of this invention represented by the formula (Dd).

(D4), the raw materials of the above compounds, can be produced in accordance with the following reactions.

[I] In case where X is O

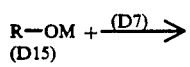
(D15)

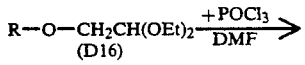
(D16)

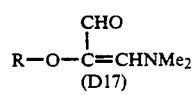
(D17)

[II] In case where X is—(direct bond)

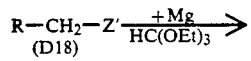
(D18)

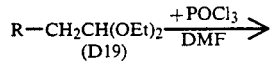
(D19)

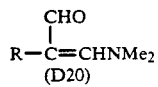
(D20)

These reactions can be carried out as follows.

[I] (D15) is reacted with bromo acetoaldehyde diethyl acetal in an anhydrous solvent (such as DMF, DMSO or THF) under heating to obtain (D16), which is then reacted with a Vilsmeier reagent (such as reaction products of phosphorus oxychloride with DMF) to produce (D17).

[II] (D19), obtained by reacting (D18) With ethyl orthoformate and a Grignard' reagent prepared from magnesium, is reacted with a Vilsmeier reagent (such as reaction products of phosphorus oxychloride with DMF) to produce (D20).

[E] Compounds of the formula (2), wherein $A_2 = A_4—Y_2—A_5$, can be produced in accordance with the following reactions. ($A_4$:Ph, FPh, Ph-Ph or FPh-Ph)

[I] In case of $Y_2 = C\#C$

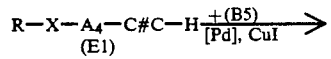
(E1)

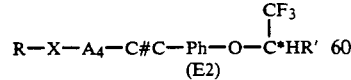
(E2)

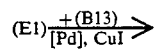

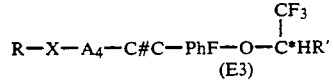
(E3)

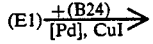

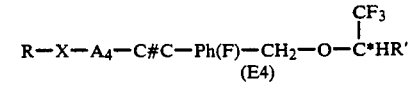
(E4)

[II] In case of $Y_2 = CH_2CH_2$

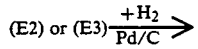

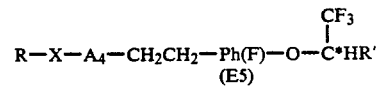
(E5)

These reactions can be carried out as follows.

[I] Compounds, containing $A_4-C\#C-A_5$ as $A_2$, for example (E2), (E3) and (E4), can be produced by reacting respectively the corresponding halides, such as (B5), (B13) and (B24) described above [B], with (E1) in triethylamine in an atmosphere of inert gas using zero- or bi-valent palladium catalyst.

[II] Compounds, containing $A_4—CH_2CH_2—A_5$ as $A_2$, for example (E5), can be produced by hydrogenation reduction with Pd/C of the corresponding compounds containing $A_4—C\#C—A_5$ as $A_2$, such as (E2), (E3) and (E4).

[F] compounds of the formula (2), wherein $A_2 = A_1—Y_2—Pyr$, can be produced in accordance with the following reactions.

[I] In case of $Y_2 = C\#C$, n=0

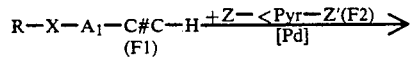
(F1)

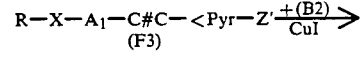
(F3)

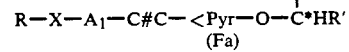
(Fa)

(F1) and (F2) are reacted in triethylamine in an atmosphere of inert gas using zero- or bi-valent palladium catalyst to obtain (F3). (F3) and (B2), as mentioned above [B], are heated under reflux in an anhydrous DMF in the presence of cuprous iodide to obtain a compound of the invention represented by the formula (Fa).

[II] In case of $Y_2 = C\#C$, n=1

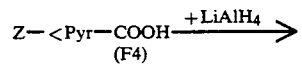
(F4)

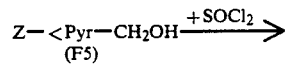
(F5)

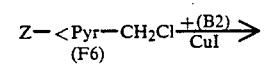
(F6)

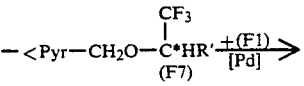
(F7)

-continued

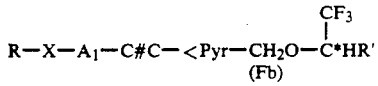
(Fb)

(F4) is reacted subsequently with LiAlH$_4$, SOCl$_2$ and then (B2) in the same manner as described in [B] [IV] forming (B24) from (B21) to obtain (F7). (F1) and (F7) are reacted in triethylamine in an atmosphere of inert gas using zero- or bi valent palladium catalyst to obtain a compound of the invention represented by the formula (Fb).

[III] In case of Y$_2$=CH$_2$CH$_2$

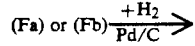

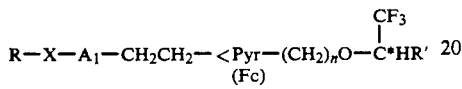
(Fc)

By hydrogenating (Fa) or (Fb) within an atmosphere of hydrogen using palladium carbon, a compound of this invention represented by the formula (Fc) is obtained.

(F1) can be prepared in the same manner as (H1) described below, wherein A$_6$ is substituted with A$_1$.

[G] Compounds of the formula (3), wherein A$_3$ is Nt, of the invention can be produced in accordance with the following reactions.

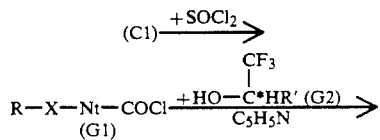

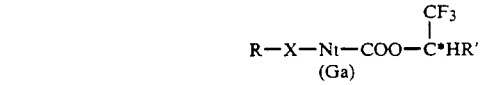
(Ga)

(C1), described above [C], is reacted with thionyl chloride to form an acid halide (G1), followed by reacting therewith an optically active alcohol (G2) in the presence of a base (such as pyridine) to obtain a compound of this invention represented by the formula (Ga).

Optically active alcohols (G2) can be obtained as the intermediates for (B2), and include (B28), (B30), (B33), and precursors (before reaction with MH) of (B39) and (B43), as mentioned above [V] and [VI] in [B].

[H] Compounds of the formula (3). wherein A$_3$ is A$_6$—Y$_3$—A$_7$, of the invention can be produced in accordance with the following reactions.

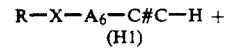 [I]

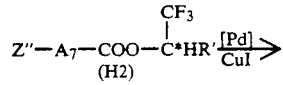

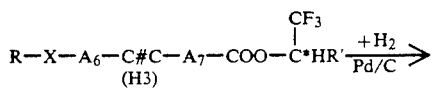

-continued

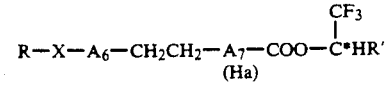
(Ha)

(H1) and (H2) are reacted in triethylamine in an atmosphere of inert gas using zero- or bi-valent palladium catalyst to obtain (H3). By hydrogenating (H3) within an atmosphere of hydrogen using palladium carbon, a compound of this invention represented by the formula (Ha) is obtained.

[II] (H1) can be prepared as follows.

i) In case of X=O

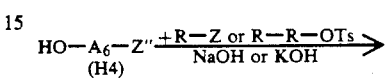

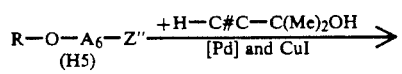

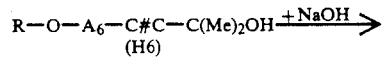

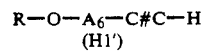
(H1')

(H4) is reacted in the presence of a base (such as sodium hydroxide) with an alkylating agent (such as alkyl halide) to obtain (H5). (H5) is reacted with 3 methyl 1-butyn-3 ol in triethylamine under an atmosphere of inert gas using zero- or bi-valent palladium catalyst to form (H6), followed by reacting powdery sodium hydroxide in anhydrous toluene to produce (H1').

ii) In case of X=—(direct bond), R=R''—CH$_2$C-H$_2$—

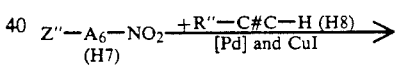

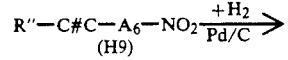

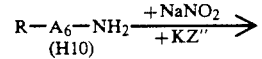

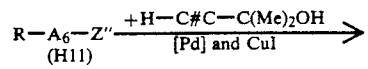

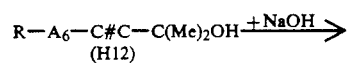

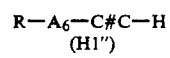
(H1'')

(H7) and (H8) are reacted in triethylamine in an atmosphere of inert gas using zero- or bi valent palladium catalyst to obtain (Hg). After diazotization of (H9), an alkali metal halide is reacted therewith to produce (H11). (H11) is reacted with 3-methyl-1-butyn-3-ol in triethylamine under an atmosphere of inert gas using zero- or bi-valent palladium catalyst to form (H12), followed by reacting powdery sodium hydroxide in anhydrous toluene to produce (H1'').

[III] (H2) can be prepared as follows.

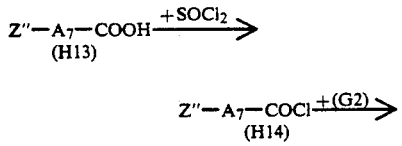

(H13) is reacted with thionyl chloride to form an acid halide (H14), followed by reacting therewith an optically active alcohol (G2), described above [G], to obtain (H2).

[J] Compounds of the formula (3), wherein $A_3$ is $A_1-Y_2-Pyr$, of the invention can be produced in accordance with the following reactions

[I] In case of $Y_2 = C\#C$ (F1) +

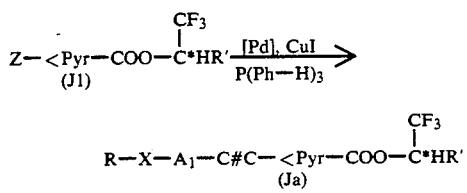

or (F1) +

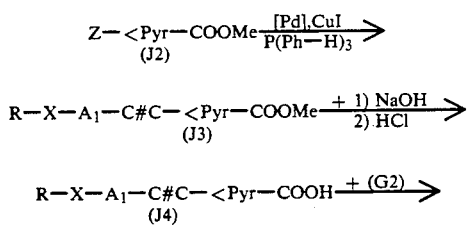

(F1) and (J1) are reacted in triethylamine in an atmosphere of inert gas using zero- or bi valent palladium catalyst to obtain a compound of this invention represented by the formula (Ja).

(Ja) may also be produced by reacting (F1) with (J2) in triethylamine in an atmosphere of inert gas using zero- or bi-valent palladium catalyst to obtain (J3), and thereafter hydrolyzing (J3) with an alkali (such as sodium hydroxide) and then treating with an acid (such as hydrochloric acid) to form (J4), followed by esterifying (J4) with an optically active alcohol (G2) mentioned above

[G], using a dehydrating agent (such as N,N'-dicyclohexylcarbodiimide).

[II] In case of $Y_2 = CH_2CH_2$

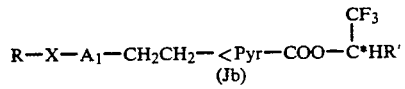

By hydrogenating (Ja) within an atmosphere of hydrogen using palladium carbon, a compound of this invention represented by the formula (Jb) is obtained wherein $A_6$ is substituted with $A_1$.

In general, liquid crystals are used in the forms of liquid crystal compositions containing two or more components; and optically active compounds of the present invention can be used as a component of liquid crystal compositions.

This invention provides a liquid crystal composition containing as components thereof a mixture of a plurality of liquid crystal compounds, said liquid crystal compounds comprising at least one compound represented by the formulae (1), (2) or (3).

Compounds of the formulae (1), (2) or (3) include ones which present liquid crystals by themselves, and ones which do not present liquid crystals by themselves but can provide liquid crystal compositions.

Liquid crystal compositions in accordance with the present invention may contain one or more liquid crystals other than the compounds of the formulae (1), (2) or (3). Examples of suitable liquid crystals include: smectic liquid crystals, for example, smectic liquid crystals free from any optically active site, such as 2-p-alkyloxyphenyl-5-alkylpyrimidines, 2-p-alkanoyloxyphenyl-5-alkylpyrimidines, 2-p-alkyloxycarbonyl-phenyl-5-alkylpyrimidines, 2-p-alkylphenyl-5-p-alkyloxy-phenylpyrimidines, 2-p-alkyloxy-m-fluorophenyl-5-alkylpyrimidines, 2-p-alkyloxyphenyl-5-(trans-4-alkylcyclohexyl)-pyridines, 2-p-alkyloxy-m-fluorophenyl-5-alkylpyridines, 2-p-(p'-alkylphenyl)phenyl-5-alkylpyrimidines, 2-p-alkylphenyl- 5-p-alkylphenylpyrimidines, 2-alkyloxyphenyl-5-alkyl picolinates, 2-p-alkyloxyphenyl-5-alkyloxypyrazines, 2-p-alkyloxyphenyl-5-alkyloxypyrimidines, 2-p-alkylphenyl-5-alkyloxypyrimidines, p'-(alkyloxycarbonyl)phenyl esters of 2-alkyloxy-4'-biphenyl-carboxylic acids, alkyl esters of 4-alkyloxy-4'-biphenyl carboxylic acids, and the like; ferroelectric liquid crystals, such as p'-(2-methylbutoxycarbonyl)phenyl esters of oa 4-alkyloxy-4'-biphenylcarboxylic acids, 2-methylbutyl esters of oa 4-n-alkyloxy-4'-biphenylcarboxylic acids, oa p-alkyloxybenzylidine-p'-amino-2-chloro-propyl cinnamates, oa p-alkyloxybenzylidine-p'-amino-2-chloropropyl cinnamates and the like; usual chiral smectic liquid crystals, such as oa 4-(p-alkyloxybiphenyl-p'-oxycarbonyl)-4'-(2-methylbutyloxycarbonyl)cyclohexanes, oa p-n-alkyloxybenzylidene-p'-(2-methylbutyloxycarbonyl)anilines, and the like; and two or more of these smectic liquid crystals, ferroelectric liquid crystals and/or chiral smectic liquid crystals Liquid crystal compositions in accordance with the present invention may contain other components, for example, chiral compounds showing no liquid crystalline properties, pleochroic dyes (such as anthraquinone dyes, azo dyes and the like), and so on.

Content (% by weight) of each component in the liquid crystal compositions are, for example, as follows: the compound(s) of the formula (1): usually 0.1–20%, preferably at least 1%, more preferably 2–10%; other smectic liquid crystal(s): usually 80–99.9%, preferably at least 90%, more preferably 95–98%; pleochroic dye(s): usually 0–5%.

By applying voltage, ferroelectric liquid crystal compositions exhibit a photo-switching phenomena, which is applied for producing display elements of quick response. See for example, JPN Patent Publication Nos. 107216/1981 and 118744/1984, and N. A. Clark and S. T. Lagerwall: Applied Physics Letters, 36, 899 (1980).

Liquid crystals, showing ferroelectricity, according to the present invention, exhibit an optical switching phenomena by the application of voltage applying, and can provide rapid response display devices, such as those described in JPN Laid-open Patents No. 107216/1981 and No. 118744/1984, and N. A. Clark and S. T. Lagerwall, "Applied Physics Letters" 36, 899 (1980).

The liquid crystal compositions of this invention can be used as photo-switching elements (display devices), for instance, by sealing in vacuum into liquid crystal cells having cell distance of 0.5-10 microns, preferably 0.5-3 microns, followed by providing polarizers on both sides.

The above liquid crystal cells can be produced by combining, through a spacer, two surface-aligned glass substrates provided with transparent electrodes. Examples of suitable spacers are alumina beads, glass fiber and polyimide film. Alignment can be done by conventional alignment treatment, such as application of polyimide membrane, rubbing treatment, oblique vapor-deposition of SiO.

Having generally described the present invention, reference will now be made to certain examples, which are included solely for purposes of illustration and are not intended to be limitative.

In the following examples, % represents % by weight; and the structure of the compounds was confirmed with analysis of NMR (nuclear magnetic resonance), MS (mass spectrum) and IR (infrared adsorption), and elemental analysis.

EXAMPLE 1

Preparation of Compound No. 1-1 in Table 1-1

1) In accordance with a known method, as described in Gradiano Castaldi et al, J. Org. Chem. 52, 3018 (1987), oa (6-methoxy-2-naphthyl)-propanoic acid was prepared.

2) To 50.0 g of oxalyl chloride, were added 10.0 g of oa (6-methoxy-2-naphthyl)-propanoic acid, and stirred for 24 hours at room temperature, followed by distilling off the excess oxalyl chloride to obtain 10:8 g of oa (6-methoxy-2-naphthyl)-propanoic acid chloride, which were used as such (without particularly purifying) in the following reaction.

3) Into 300 ml of dry toluene, were dissolved 10.8 g of oa (6-methoxy-2-naphthyl)-propanoic acid chloride, followed by introducing dry ammonia at a temperature not more than 15° C. for 30 minutes. Stirring was continued at room temperature for 3 hours, and then precipitated while solid was filtered off. The resulting white solid was washed with toluene and then water, followed by recrystallizing with ethanol to obtain 10.0 g of oa (6-methoxy-2-naphthyl)-propanamide.

4) In 50 ml of dry THF, were suspended 3.0 g of oa (6-methoxy-2-naphthyl)-propanamide, followed by adding thereto 8.3 g of trifluoroacetic anhydride and then stirring at room temperature for 12 hours. The resulting reaction mixture was poured into 200 ml of iced water, and then precipitated white solid was filtered off. After purifying with silica gel column, the product was recrystallized twice with ethanol to obtain 2.1 g of oa (6-methoxy-2-naphthyl)propanonitrile (Compound No. 1-1) of this invention.

Figure 1B:
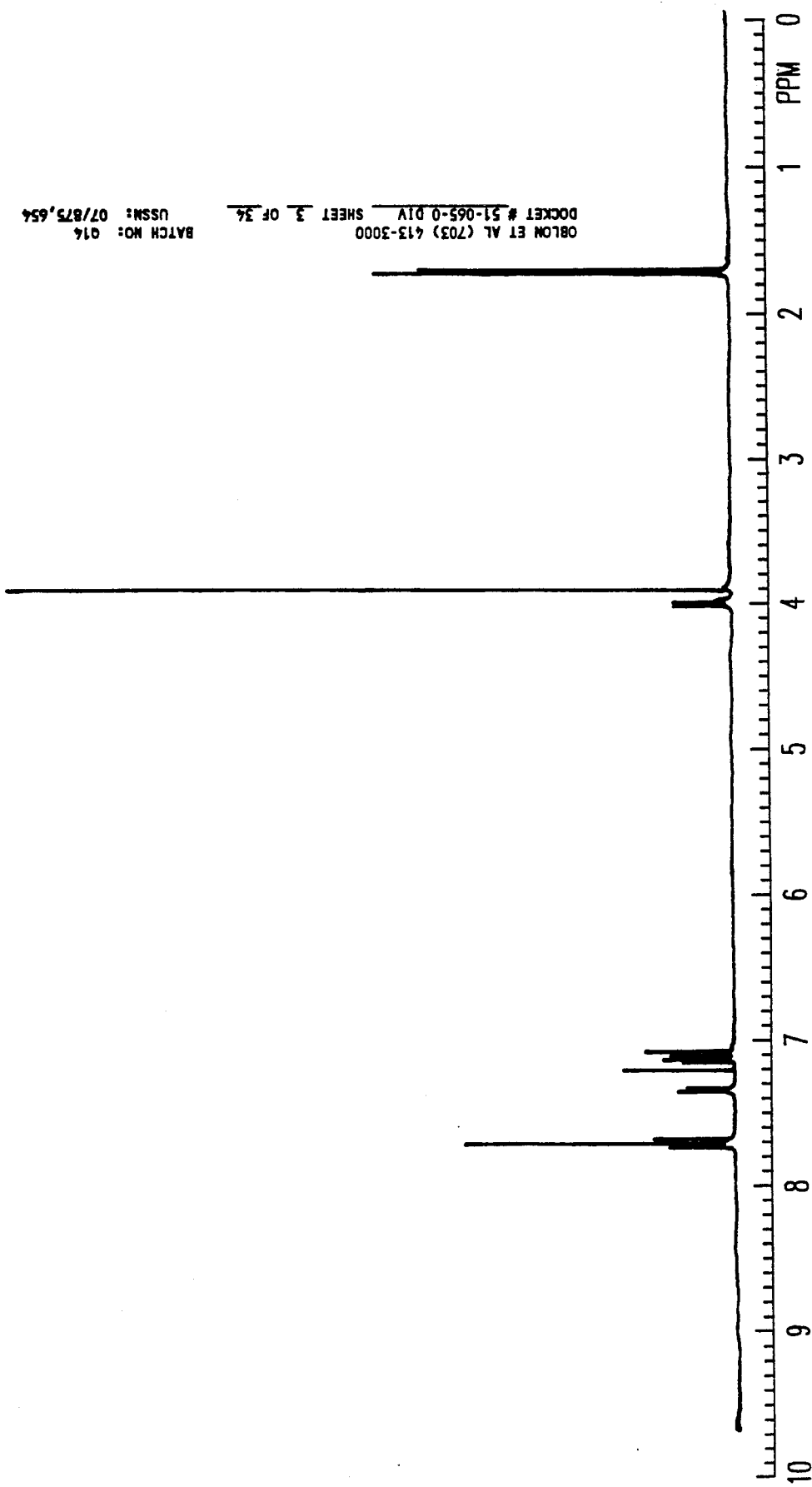

IR spectrum and $^1$H-NMR spectrum the compound were as shown in FIG. 1(a) and FIG. 1(b), respectively. Elemental analysis (%) [theoretical] was as follows:

C:79.87 [79.59], H:6.10 [6.20], N:6.60 [6.63]

EXAMPLE 2

Preparation of Compound No. 1-10 in Table 1-1

1) 15.6 g of boron tribromide, were dissolved in 100 ml of methylene chloride and cooled to −10° C. To this, 80 ml of methylene chloride solution of 6.0 g oa (6-methoxy-2-naphthyl)-propanonitrile were added dropwise over 2 hours, followed by stirring for 7 hours at room temperature. The resulting reaction mixture was poured into 500 ml of iced water and extracted with ether, followed by washing the ether phase twice with water and then distilling off the solvent. The resulting solid was recrystallized with chloroform-hexane mixture to obtain 4.5 g of oa (6-hydroxy-2-naphthyl)-propanonitrile.

2) Into 20 ml of dry THF, were dissolved 1.5 g of oa (6-hydroxy-2-naphthyl)-propanonitrile and 3.0 g of triphenylphosphine, and cooled to 5° C. To this solution, were added dropwise 2.0 g of diethyl azodicarboxylate and then 1.2 g of n-decyl alcohol, and stirred at room temperature for 12 hours. The resulting reaction mixture was extracted with ether, followed by washing three times the ether phase with water and then distilling off the ether. The resulting oily product was extracted with hexane, and the hexane-soluble matter was recrystallized with methanol to obtain 0.7 g of oa (6-n-decyloxy-2-naphthyl)propanonitrile (Compound No. 1-10) of this invention.

Figure 2A:
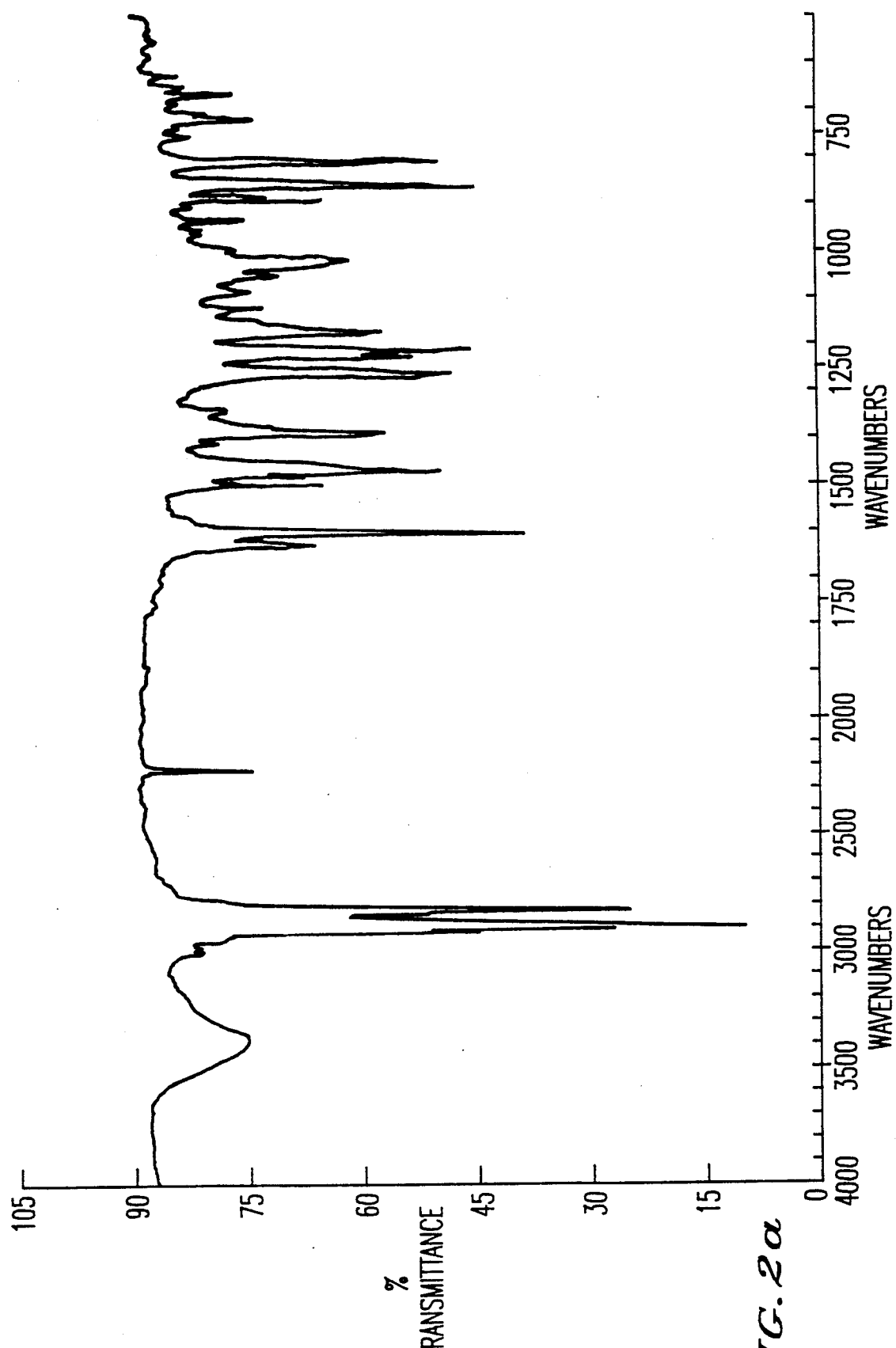
Figure 2B:
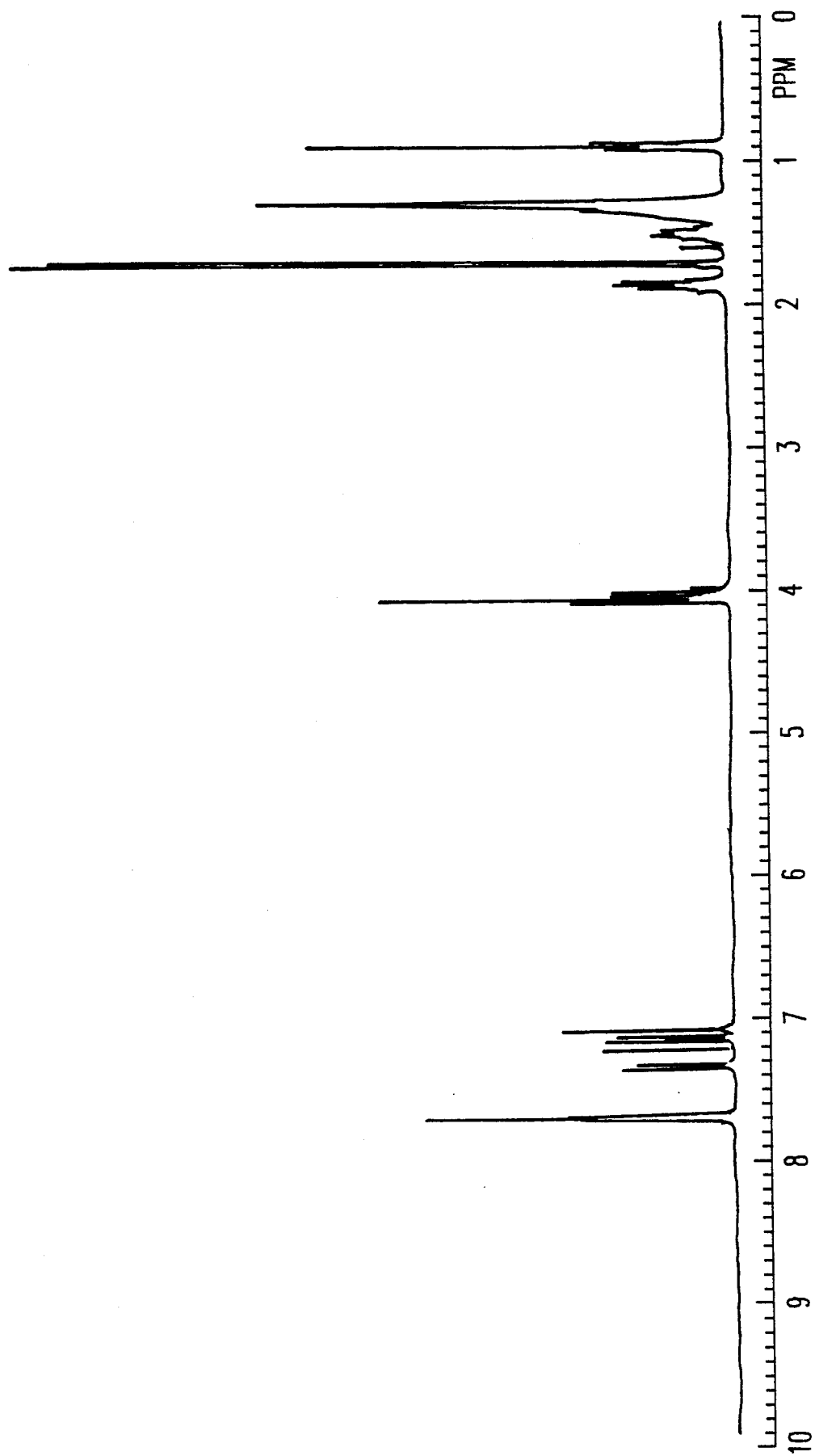

IR spectrum and $^1$H-NMR spectrum of the compound were shown in FIG. 2(a) and FIG. 2(b), respectively. Elemental analysis (%) [theoretical] was as follows:

C:81.77 [81.85], H:9.29 [9.26], N:4.17 [4.15]

EXAMPLE 3

Preparation of Compound No. 1-13 in Table 1-1

Example 2) was repeated except that 0.67 g of oa 2-methyl-1-butanol was used instead of 1.2 g of decyl alcohol, and that the hexane-soluble matter was purified using liquid chromatography instead of recrystallization with methanol, to obtain 0.5 g of Compound No. 1-13 of this invention.

Figure 3A:
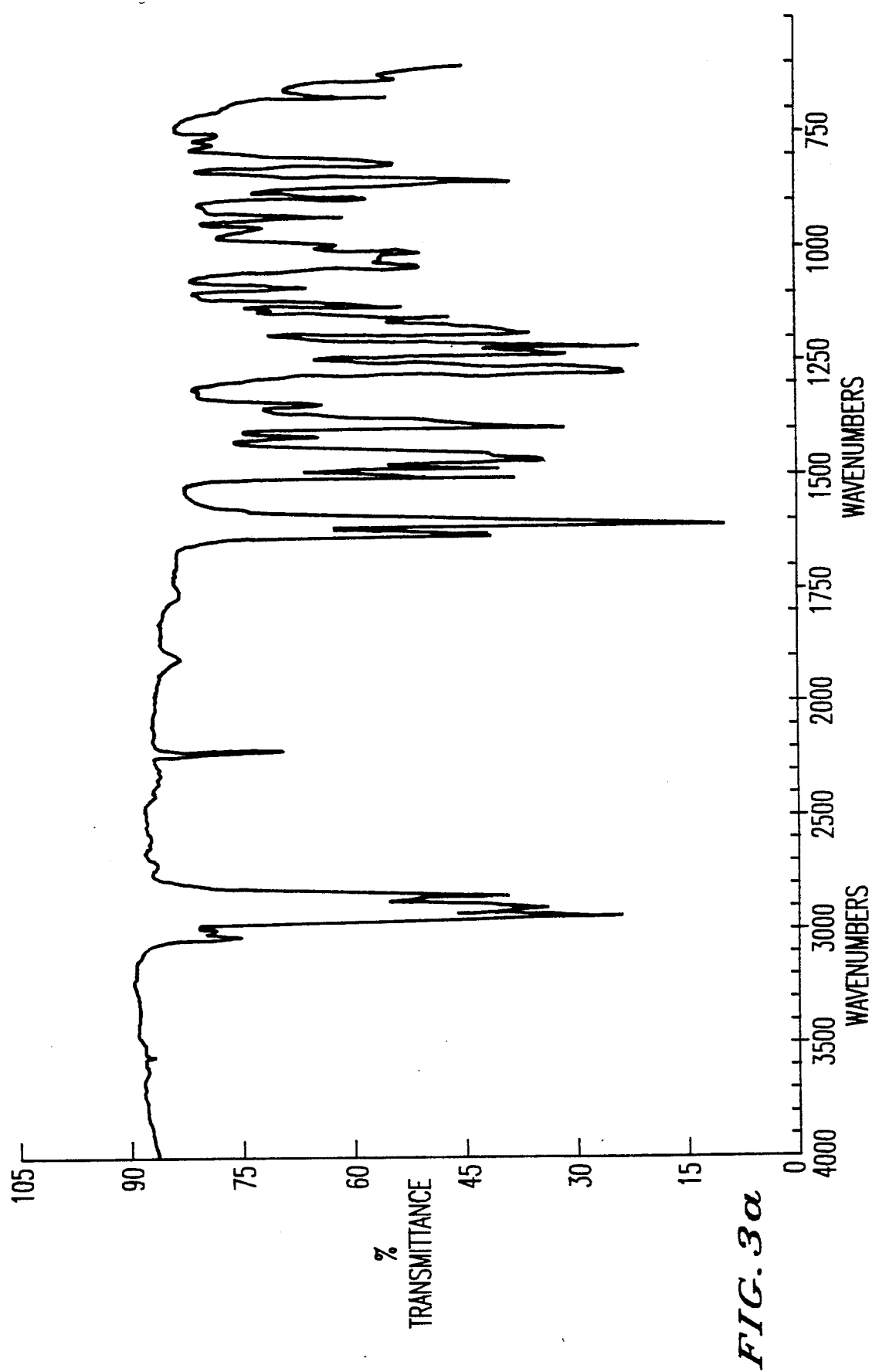
Figure 3B:
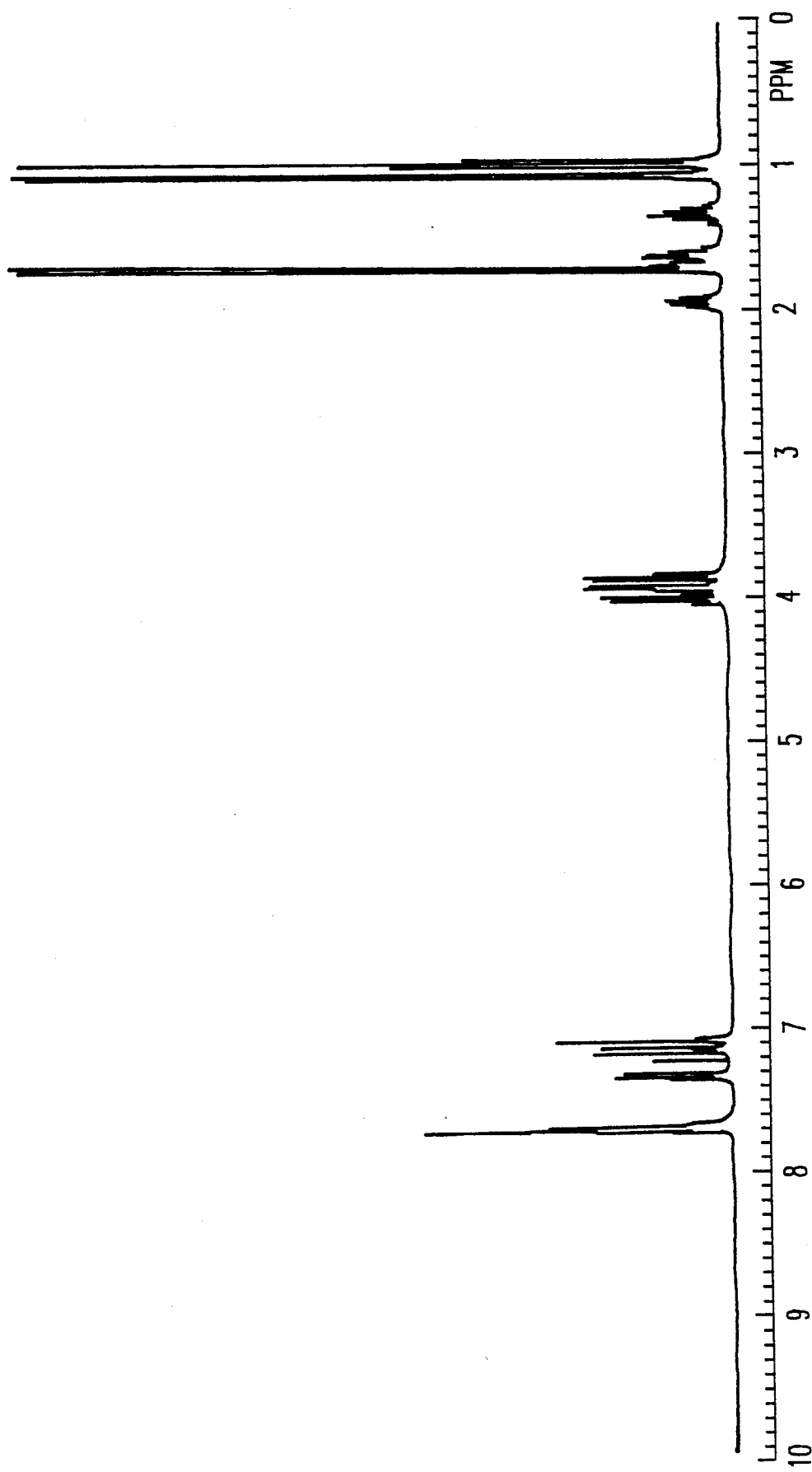

IR spectrum and $^1$H-NMR spectrum of the compound were as shown in FIG. 3(a) and FIG. 3(b), respectively. Elemental analysis (%) [theoretical] was as follows:

C:80.79 [80.86], H:7.94 [7.92], N:5.20 [5.24]

EXAMPLE 4

Preparation of Compound No. 1-66 in Table 1-2

1) Into 20 ml of dry toluene, were dissolved 1.5 g of oa (6-hydroxy-2-naphthyl)-propanonitrile and then 1.0 ml of pyridine and stirred at room temperature. To this solution, were added dropwise 10 ml of dry toluene solution of 2.2 g of 4-n-hexyloxybenzoic acid chloride (prepared from 4-n-hexyloxybenzoic acid with thionyl chloride), and stirred at room temperature for 4 hours. The resulting reaction mixture was washed subsequently with water, 1N-HCl, water, saturated NaHCO$_3$ aqueous solution and then water, followed by distilling off the solvent. The resulting solid was recrystallized twice with ethanol to obtain 2.1 g of Compound No. 1-66 of this invention.

Figure 4A:
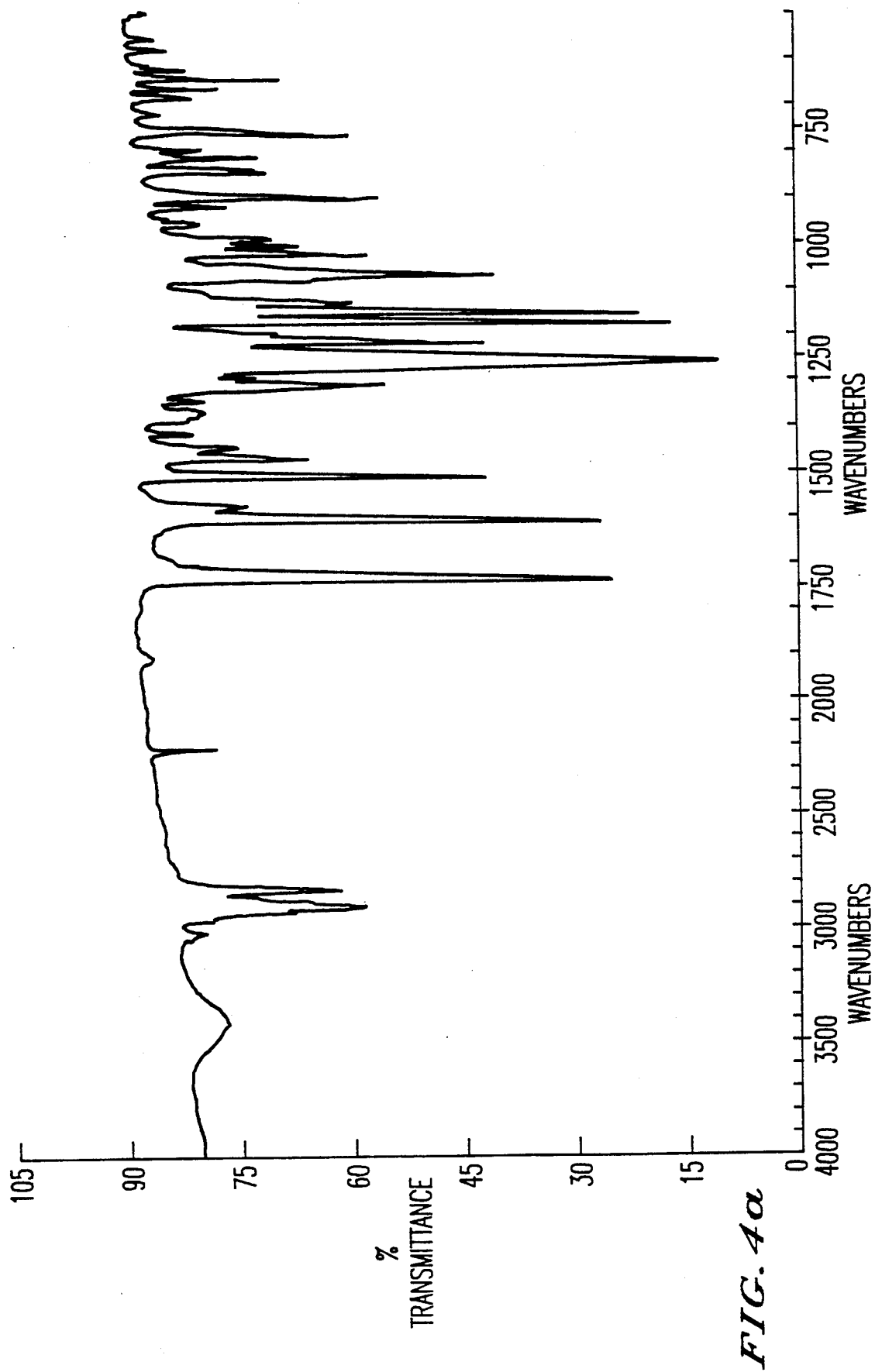
Figure 4B:
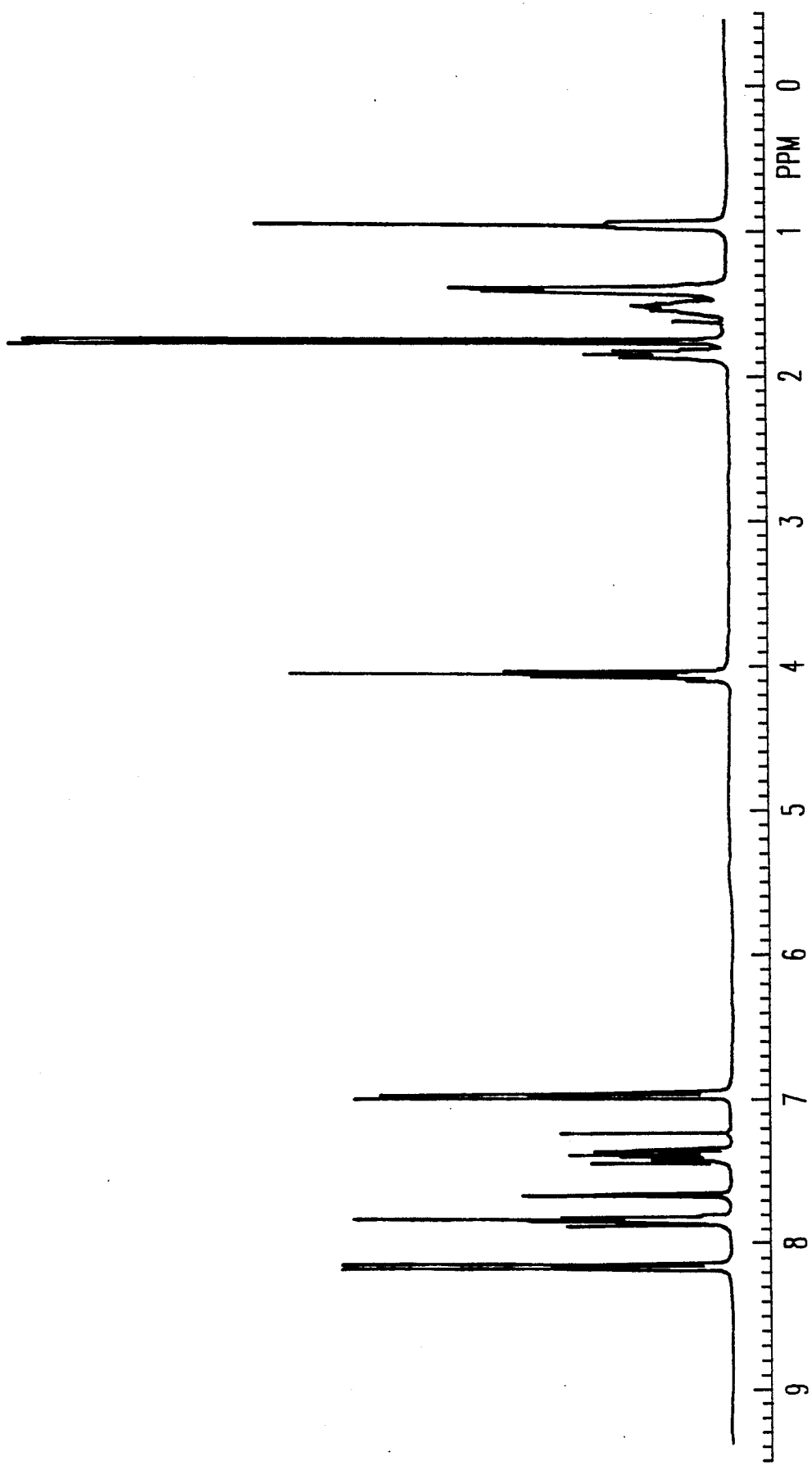

IR spectrum and $^1$H-NMR spectrum of the compound were as shown in FIG. 4(a) and FIG. 4(b), respectively. Elemental analysis (%) [theoretical] was as follows:

C:77.70 [77.78], H:6.88 [6.78], N:3.49 [3.49]

EXAMPLE 5

Preparation of Compound No. 1-63 in Table 1-2

Example 4 was repeated except that 2.0 g of 4-hexylbenzoic acid chloride (prepared from 4-n-hexylbenzoic acid with thionyl chloride) were used instead of 2.2 g of 4-n-hexyloxybenzoic acid chloride to obtain 2.2 g of Compound No. 1-63 of this invention.

Figure 5A:
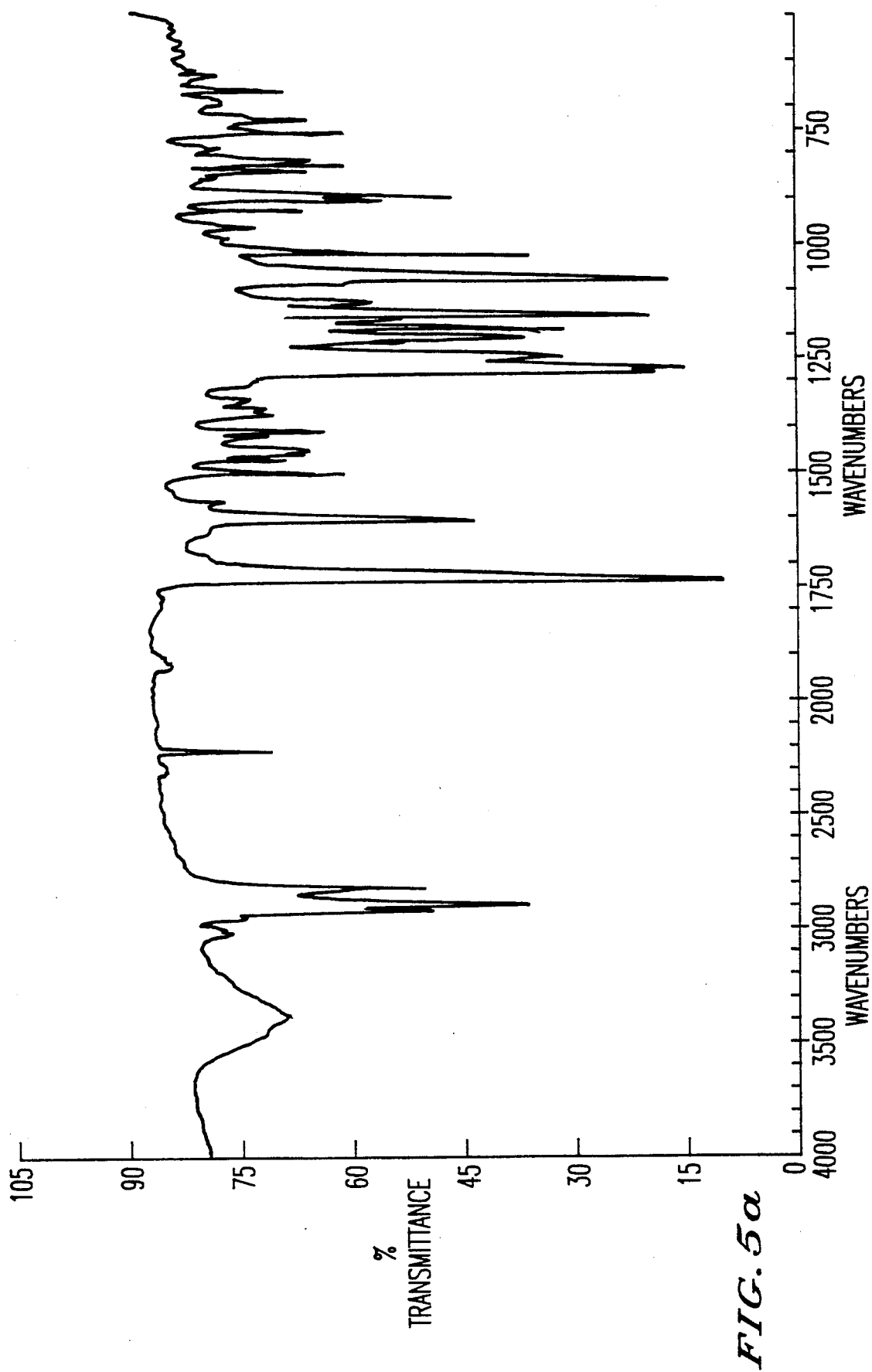
Figure 5B:
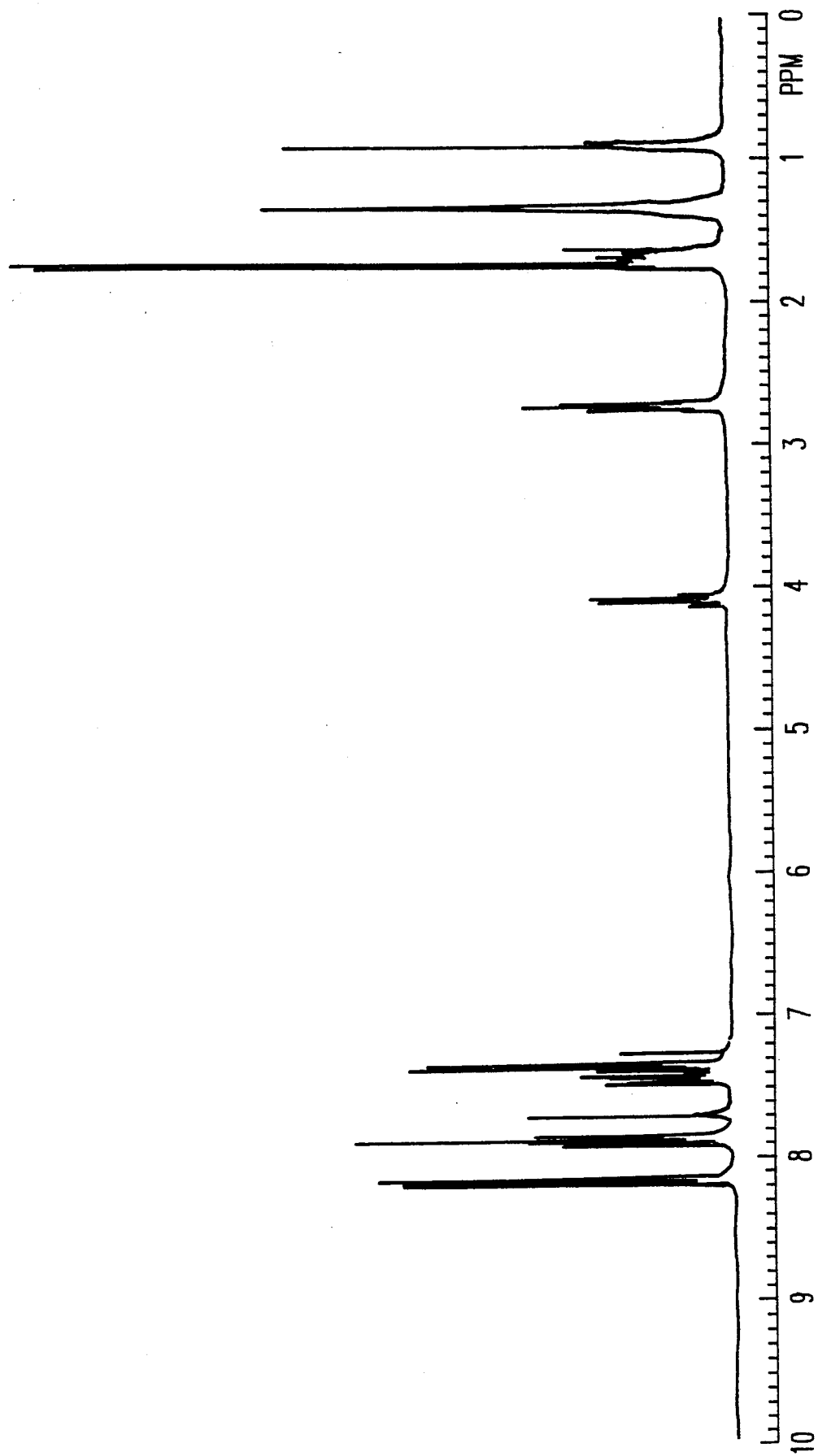

IR spectrum and $^1$H-NMR spectrum of the compound were shown in FIG. 5(a) and FIG. 5(b), respectively. Elemental analysis (%) [theoretical] was as follows:

C:81.12 [81.01], H:710 [7.06], N:3.63 [3.63]

EXAMPLE 6

Preparation of Compound No. 2-4 in Table 2-1

Into 100 ml of dry DMF containing 0.4 g of sodium hydride (purity 60%), were added dropwise 1.84 g of R-form oa 1-trifluoromethyl-heptanol, at room temperature with such a speed not causing too rapid generation of hydrogen, to prepare sodium salt (alkoxide) or R-form oa 1-trifluoromethyl-heptanol. After addition was over, stirring was continued further an hour at room temperature, followed by adding thereto 4.36 g of p-n-decyloxy-p'-iodo-biphenyl and 1.90 g of cuprous iodide and then refluxing for 3 hours. After cooling, the product was introduced into iced water, and extracted with hexane. The hexane phase was washed subsequently with water, 1N-HCl aqueous solution and then water, followed by distilling off the hexane to obtain a black oil. This oil was dissolved into hexane, and purified with silica gel column to obtain 1.2 g of liquid oa p-n-decyloxy-p'-(1-trifluoromethyl-heptyloxy)biphenyl [Compound No. 2-4] of this invention.

Figure 6A:
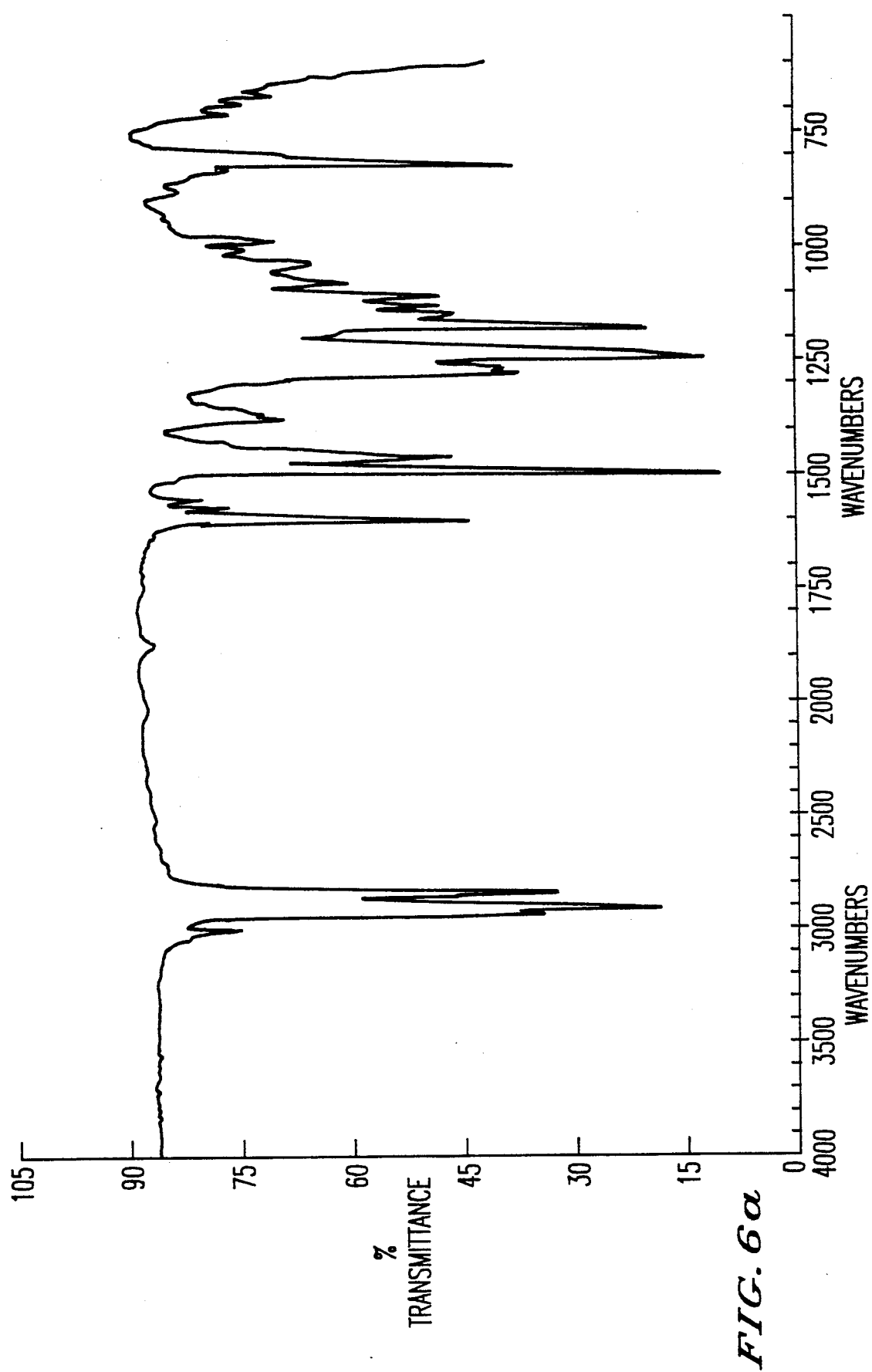
Figure 6B:
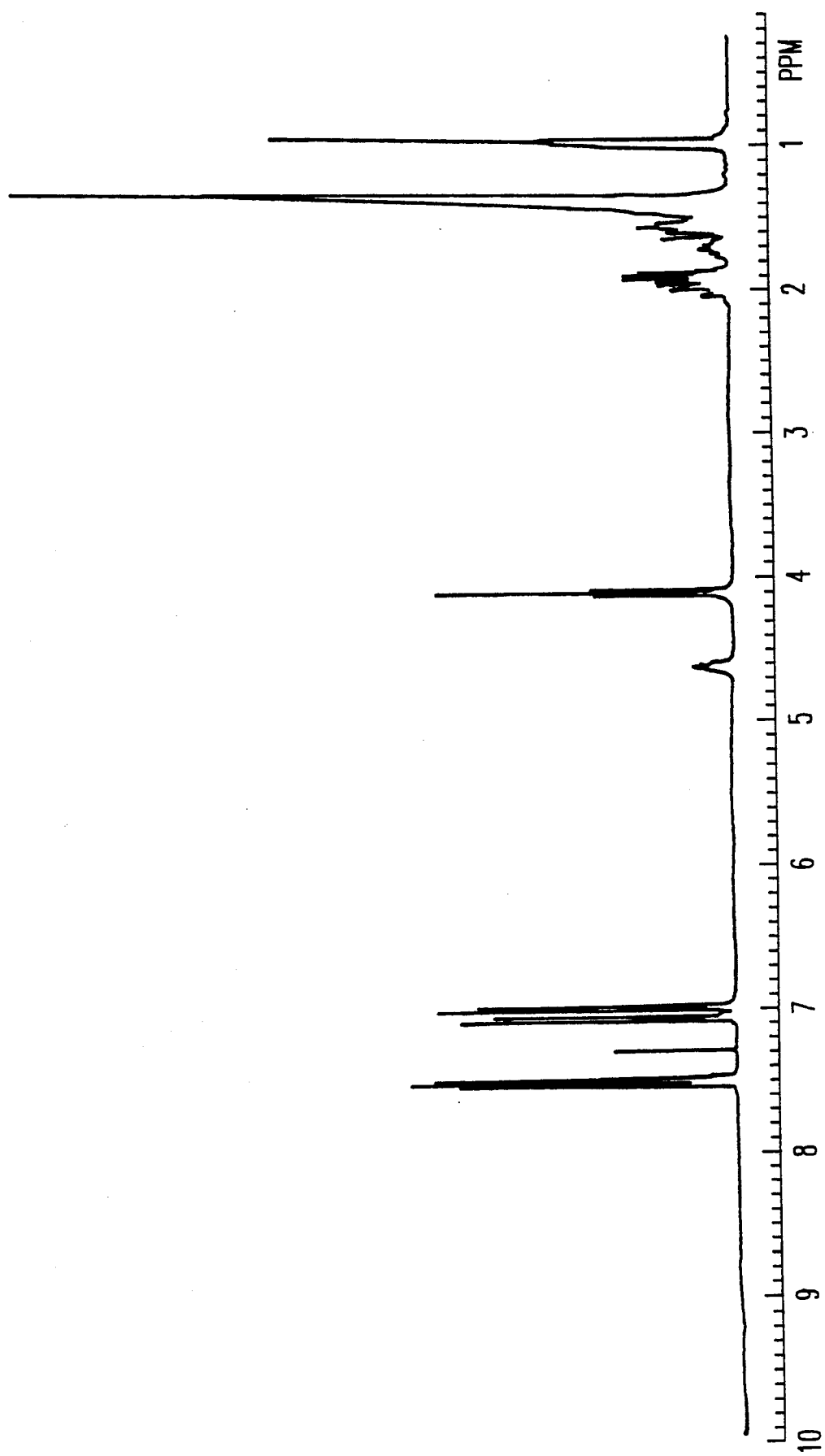
Figure 6C:
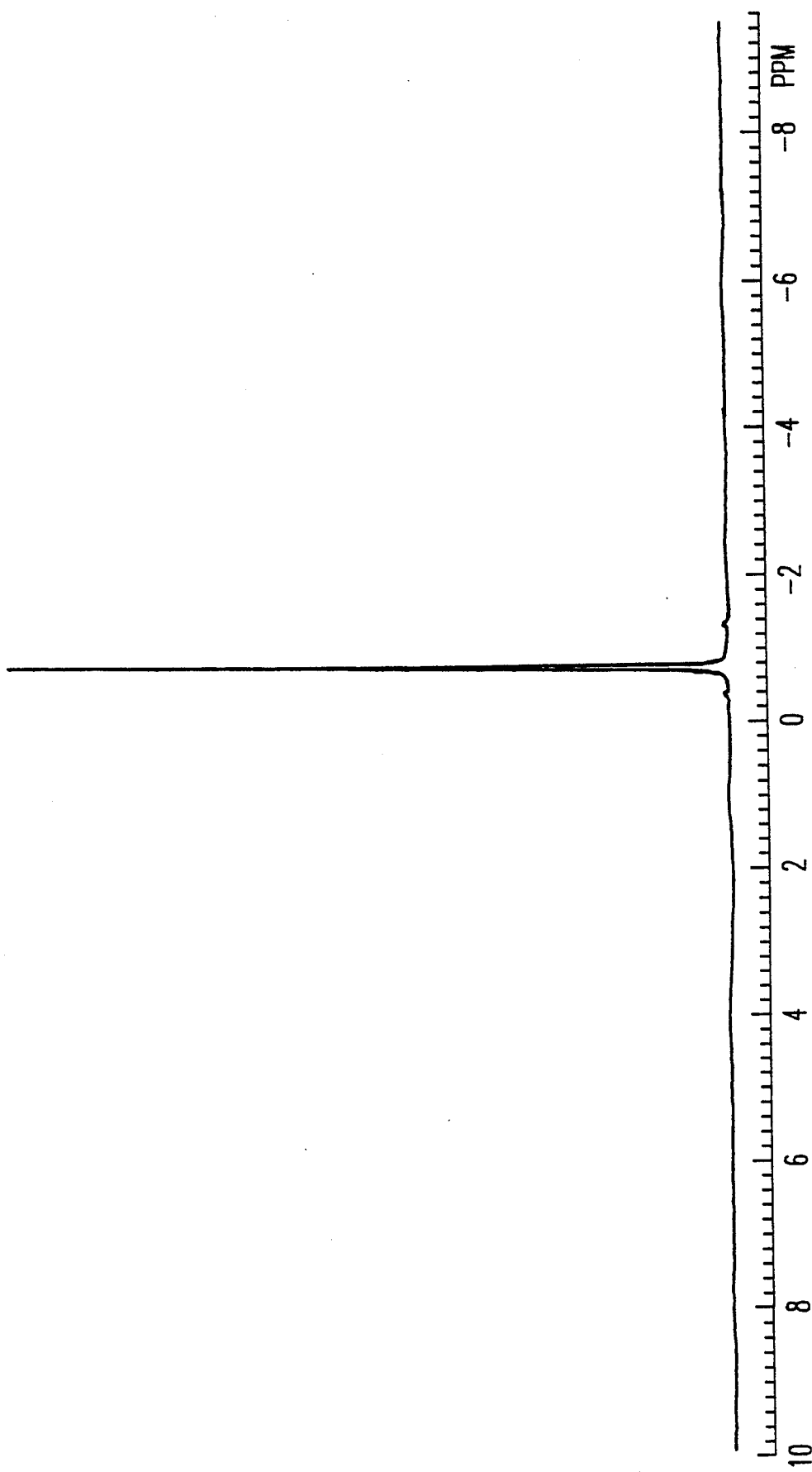

IR spectrum, $^1$H-NMR spectrum and F-NMR spectrum of the compound were as shown in FIG. 6(a), FIG. 6(b) and FIG. 6(c), respectively. Elemental analysis (%) [theoretical] was as follows: C:73.32 [73.17], H:8.61 [8.74], 0:6.39 [6.58], F:11.68 [11.59]

EXAMPLE 7

Preparation of Compound No. 2-70 in Table 2-2

Example 6 was repeated except that 3.59 g of p-n-decyloxy-p'-chloromethylbiphenyl (prepared reducing p-n-decyloxy-p'-carboxybiphenyl with lithium aluminum hydride, followed by chlorinating with thionyl chloride) were used instead of 4.36 g of p-n-decyloxy-p'-iodo-biphenyl and 1.90 g of cuprous iodide, and that refluxing was carried out for 3 hours instead of 2 hours, to obtains 2.9 g of liquid oa p-n-decyloxy-p'-(1-trifluoromethyl-heptyloxymethyl)biphenyl [Compound No. 2-70] of this invention.

Figure 7A:
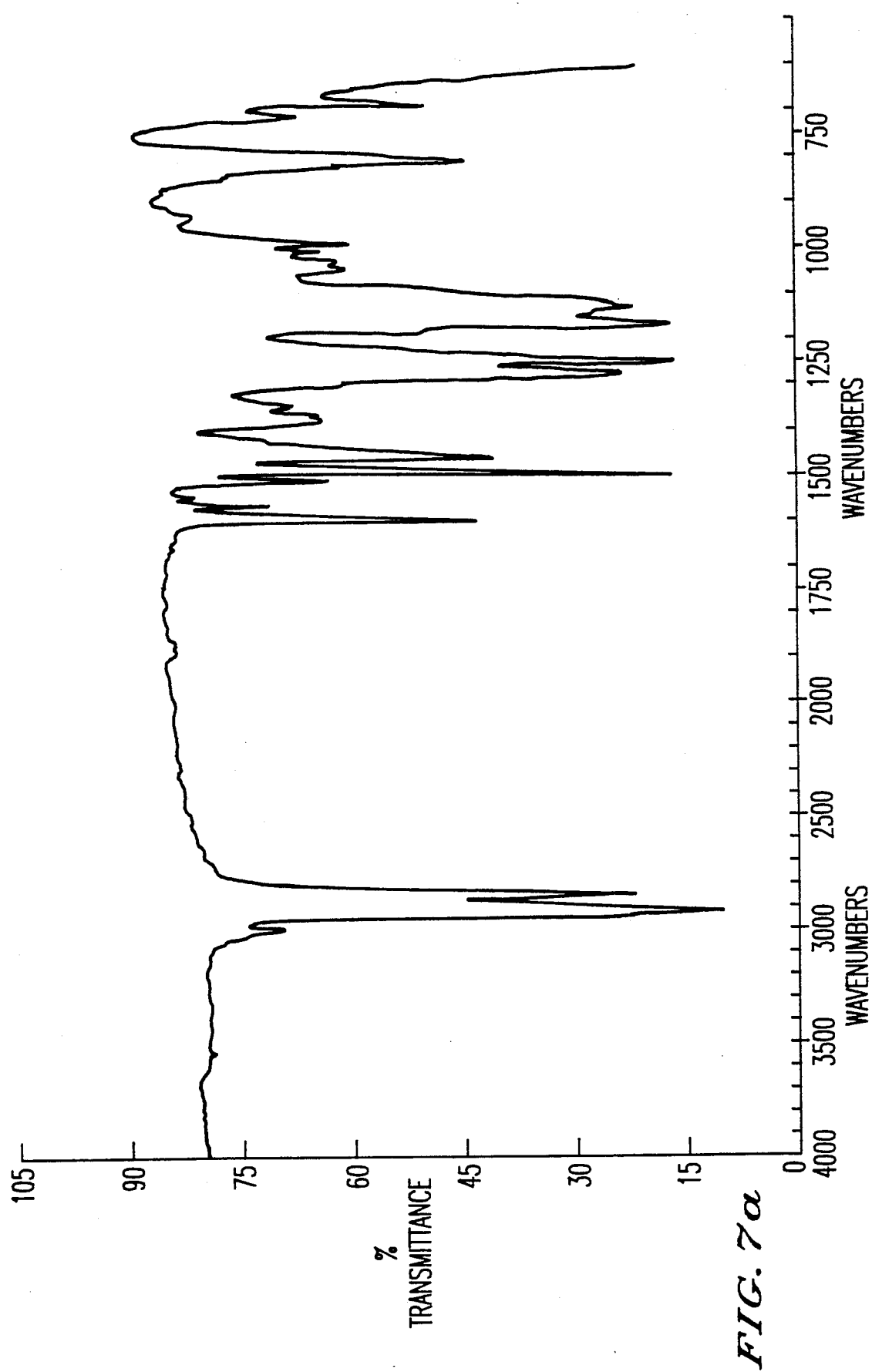
Figure 7B:
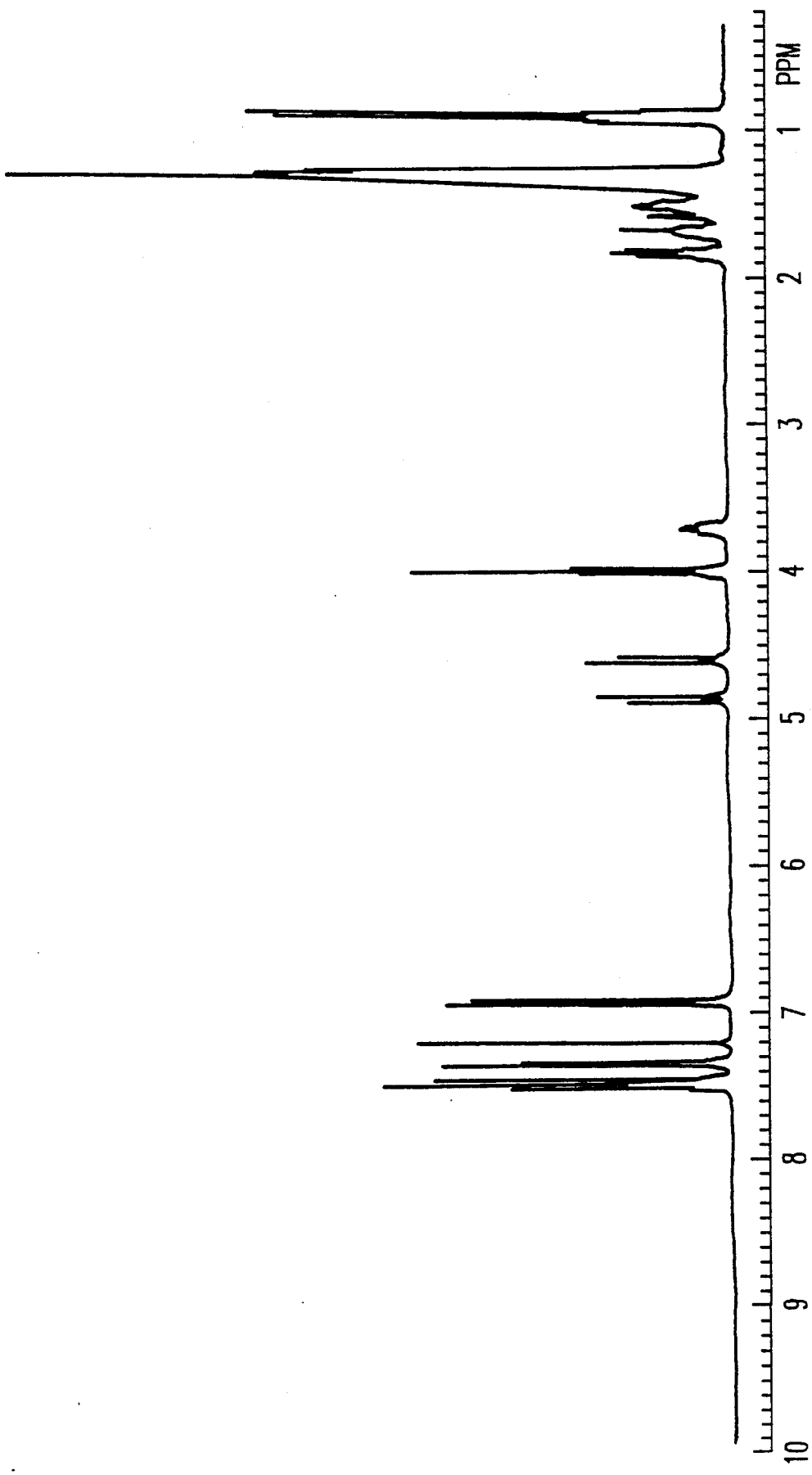
Figure 7C:
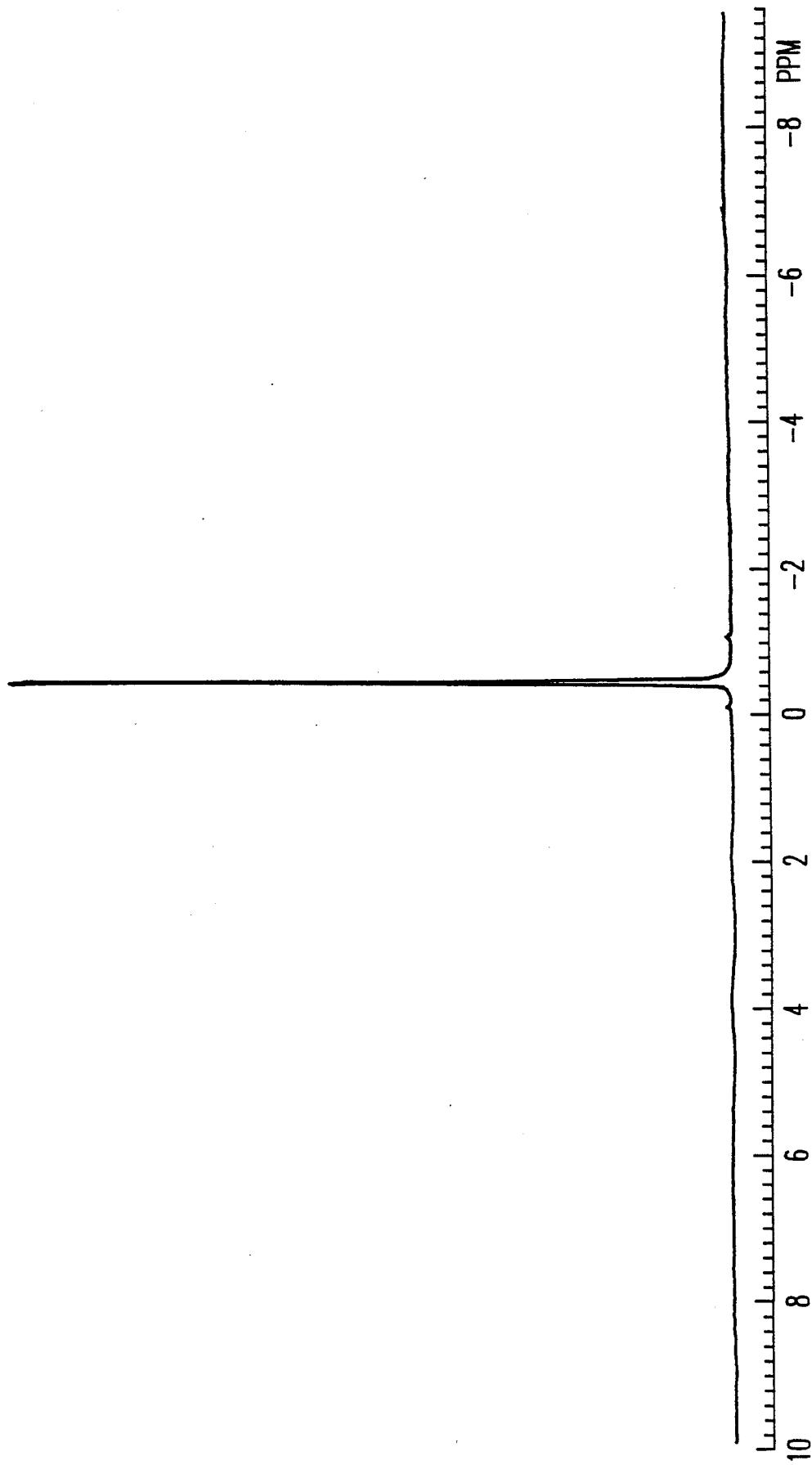

IR spectrum, $^1$H-NMR spectrum and F-NMR spectrum of the compound were as shown in FIG. 7(a), FIG. 7(b) and FIG. 7(c), respectively. Elemental analysis (%) [theoretical] was as follows: C:73.37 [73.52], H:8.98 [8.89], 0:6.43 [6.32], F:11.22 [11.27]

EXAMPLE 8

Preparation of Compound No. 4-10 in Table 4

1) Into 100 ml of dry DMF containing 0.86 g of sodium hydride (purity 60%), were added dropwise 3.9 g of R-form oa 1-trifluoromethyl-heptanol, at room temperature with such a speed not causing too rapid generation of hydrogen, to prepare sodium salt (alkoxide) of R-form oa 1-trifluoromethyl-heptanol After addition was over, stirring was continued further an hour at room temperature, followed by adding thereto 4.80 g of p-iodo-benzonitrile and then refluxing for 2 hours. After cooling, the product was introduced into iced water, and extracted with hexane The hexane phase was washed subsequently with water, 1N-HCl aqueous solution and then water, followed by purifying with silica gel column to obtain 5.16 g of oily oa p-(1-trifluoromethyl-heptyloxy)- benzonitrile.

2) Into 20 ml of dry ethanol containing 3.76 g of oa p-(1-trifluoromethyl-heptyloxy)-benzonitrile, about 1 g of dry hydrogen chloride was introduced under stirring at a temperature below 10° C. After stirring at room temperature for 3 days, solvent was distilled off to obtain any oily product To this, were added slowly 20 ml of dry ethanol containing about 2 g of ammonia under cooling with ice, followed by stirring at room temperature for 3 days. Ethanol and ammonia were removed to obtain 3.40 g of oily oa p-(1-trifluoromethyl-heptyloxy)-benzamidine hydrochloride. This oily hydrochloride was solidified by trituration in hexane to use the following reaction.

3) To a solution prepared from 30 ml of anhydrous ethanol and 0.35 g of sodium metal, were added 1.60 g of the above hydrochloride and 1.20 g of alpha-n-decyl-beta-dimethylaminoacrolein and heated under reflux for 6 hours. After completion of the reaction, solvent was removed and then the product was extracted with toluene. The toluene phase was washed with 1N hydrochloric acid aqueous solution and then with water, followed by distilling off the toluene to obtain a yellow oily material. The material was dissolved into hexane, and purified with silica gel column to obtain 0.65 g of oa 5-n-decyl-2-[p-(1-trifluoromethylheptyloxy)phenylpyrimidine [Compound No. 4-10] of this invention.

Figure 8A:
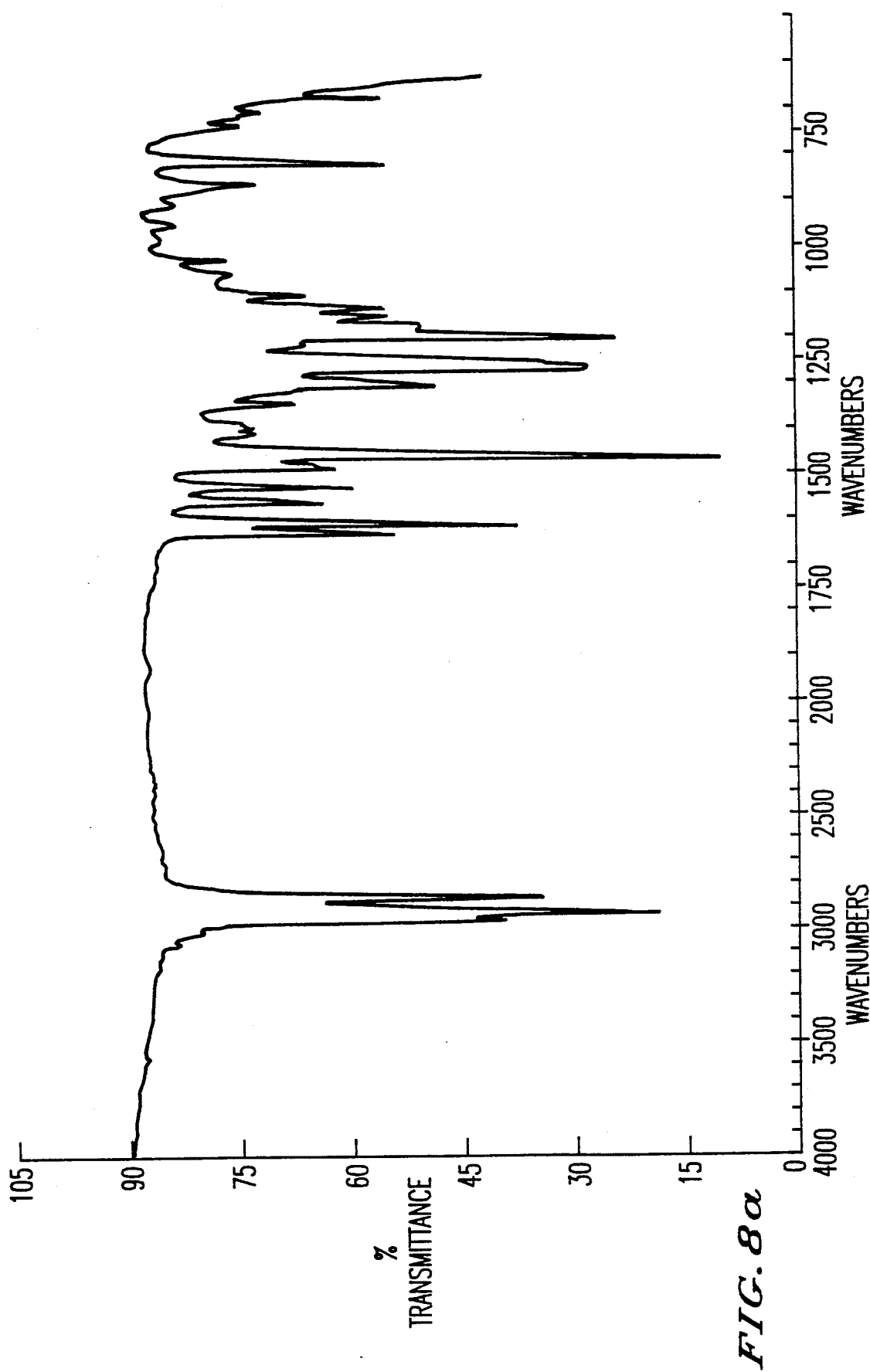
Figure 8B:
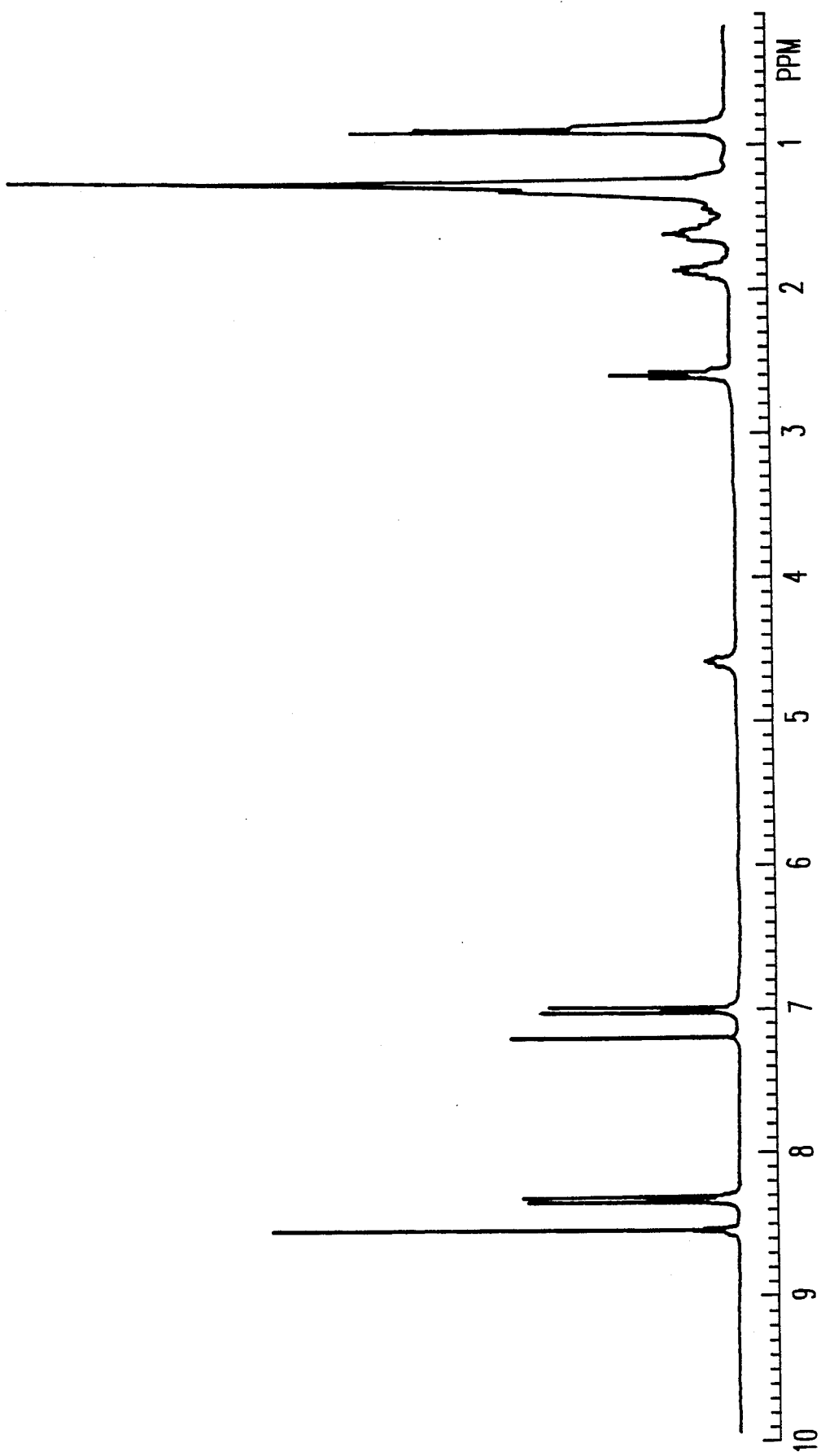
Figure 8C:
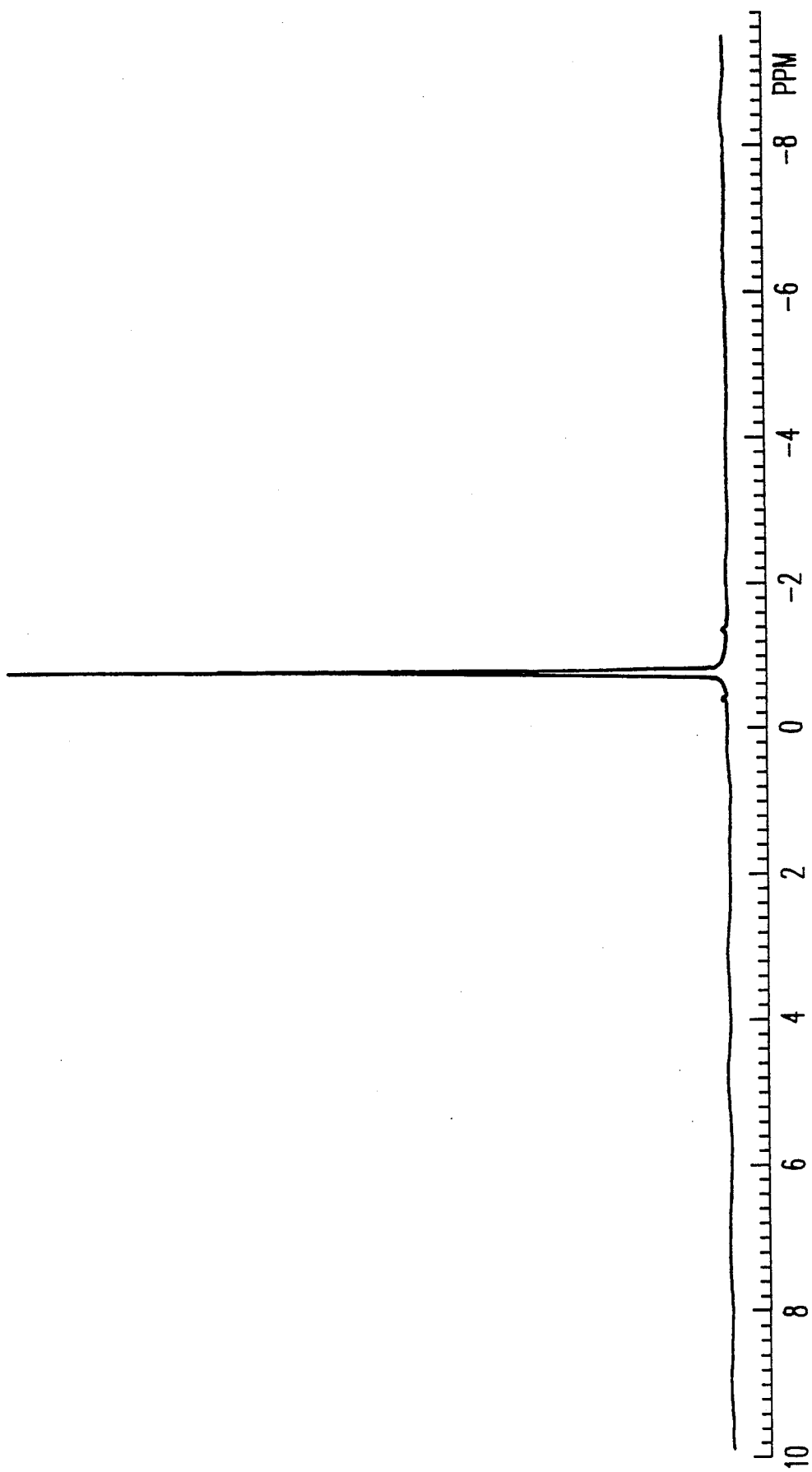

IR spectrum, $^1$H-NMR spectrum and F-NMR spectrum of the compound were as shown in FIG. 8(a), FIG. 8(b) and FIG. 8(c), respectively. Elemental analysis (%) [theoretical] was as follows: C:70.03 [70.29], H:8.71 [8.58], N:5.99 [5.86], 0:3.44 [3.35], F:11.83 [11.92]

EXAMPLE 9

Preparation of Compound No. 5-4 in Table 5-1

1) Into 200 ml of dry DMF containing 2.0 g of sodium hydride (purity 60%), were added dropwise 9.2 g of S-form oa 1-trifluoromethyl-heptanol, at room temperature with such a speed not causing too rapid generation of hydrogen, to prepare sodium salt (alkoxide) of S-form oa 1-trifluoromethyl-heptanol. After the addition was over, stirring was continued further an hour at room temperature, followed by adding thereto 12.4 g of p-iodo-nitro-benzene and then refluxing for 2 hours. After cooling, the product was introduced into iced water, and extracted with hexane. The hexane phase was washed subsequently with water, 1N-hydrochloric acid aqueous solution and then water, followed by purifying with silica gell column to obtain 7.7 g of oily oa p-(1-trifluoromethylheptyloxy)nitrobenzene.

2) To 100 ml of dry ethanol containing 77.7 g of oa p-(1-trifluoromethyl-heptyloxy)-nitrobenzene, was added 0.5 g of 5% Pd/C (5% palladium carbon) followed by carrying out reduction within an atmosphere of hydrogen at normal pressure under stirring at room temperature. After it was confirmed that no absorption of hydrogen was observed, the catalyst was removed by filtration and then the ethanol was distilled off to obtain 6.7 g of oily oa p-(1-trifluoromethylheptyloxy)-aniline.

3) To 200 ml of water containing 25 g of 36% hydrochloric acid, were added 6.7 g of oa p-(1-trifluoromethyl-heptyloxy)-aniline, and cooled to a temperature below 5° C., followed by adding thereto dropwise 1.7 g of sodium nitrite dissolved in 10 ml of water. After the addition was over, stirring was continued for an hour, and then 20 g of potassium iodide dissolved in 20 ml of water were added thereto, followed by putting back the temperature gradually to room temperature and stirring was continued until no evolution of nitrogen was observed. After completion of the reaction, the product was extracted with hexane. The hexane phase was washed subsequently with water, an aqueous solution of sodium hydrogen sulfite and then water, followed by distilling off the hexane to obtain 77 g of oily oa p-(1-trifluoromethylheptyloxy)iodobenzene.

4) Using 40 mg of dichloro-bis-triphenylphosphin palladium and 10 mg of cuprous iodide as the catalyst, 1.3 g of p-n-decyloxyphenylacetylene and 1.9 g of oa p-(1-trifluoromethyl-heptyloxy)iodobenzene were reacted in 50 ml of triethylamine under an atmosphere of nitrogen at room temperature for 24 hours. After completion of the reaction, the triethylamine was removed and then the product was extracted with toluene. The toluene phase was washed with 1N hydrochloric acid aqueous solution and then with water, followed by distilling off the toluene to obtain a black oily material. This material was dissolved into hexane, and purified by passing through a short silica gel column and then recrystallizing twice with ethanol to obtain 2.0 g of white crystalline oa p-n-decyloxy-p'-(1-trifluoromethyl-heptyloxy)tolan [Compound No. 5-4] of this invention.

Figure 9A:
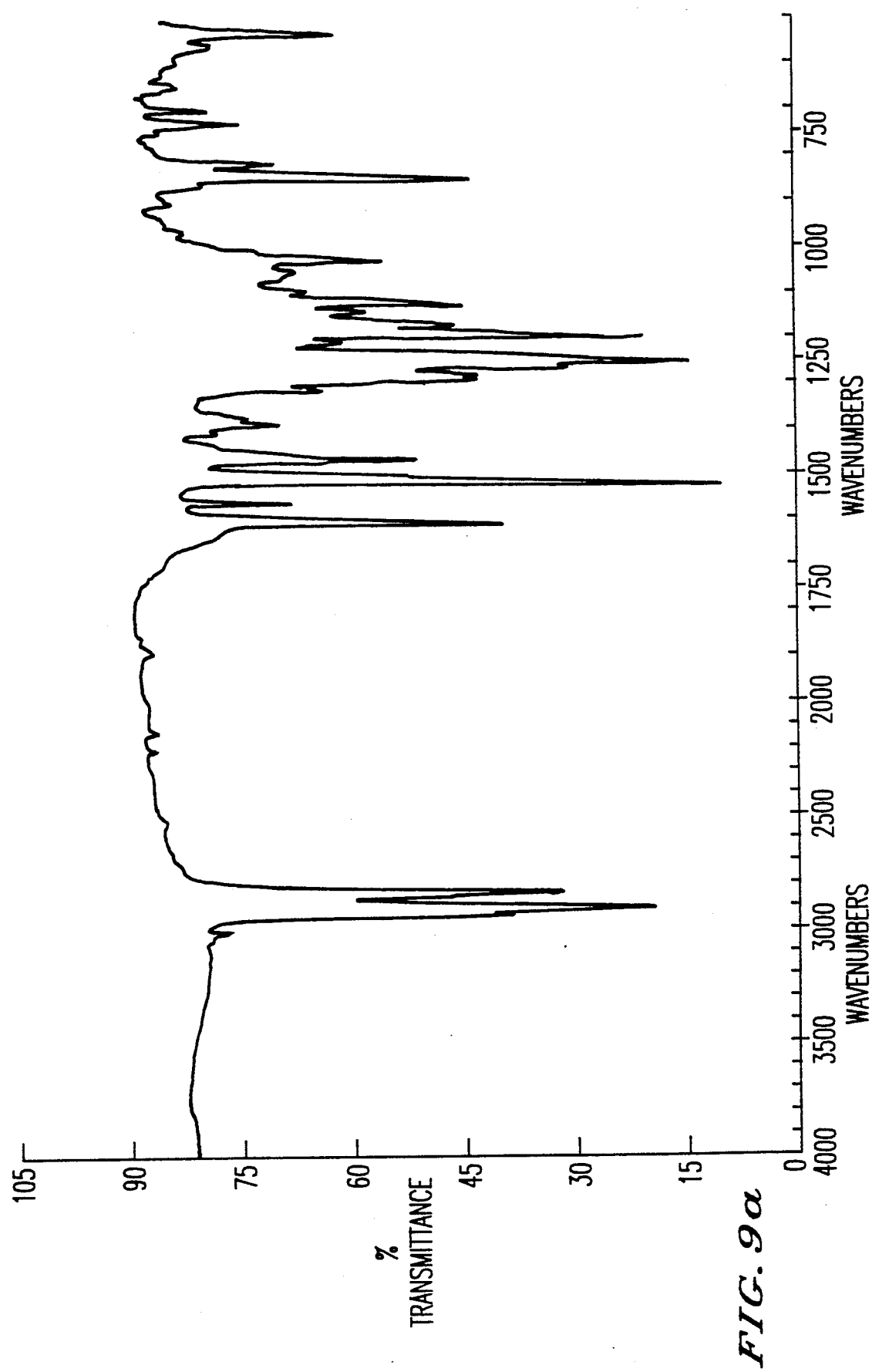
Figure 9B:
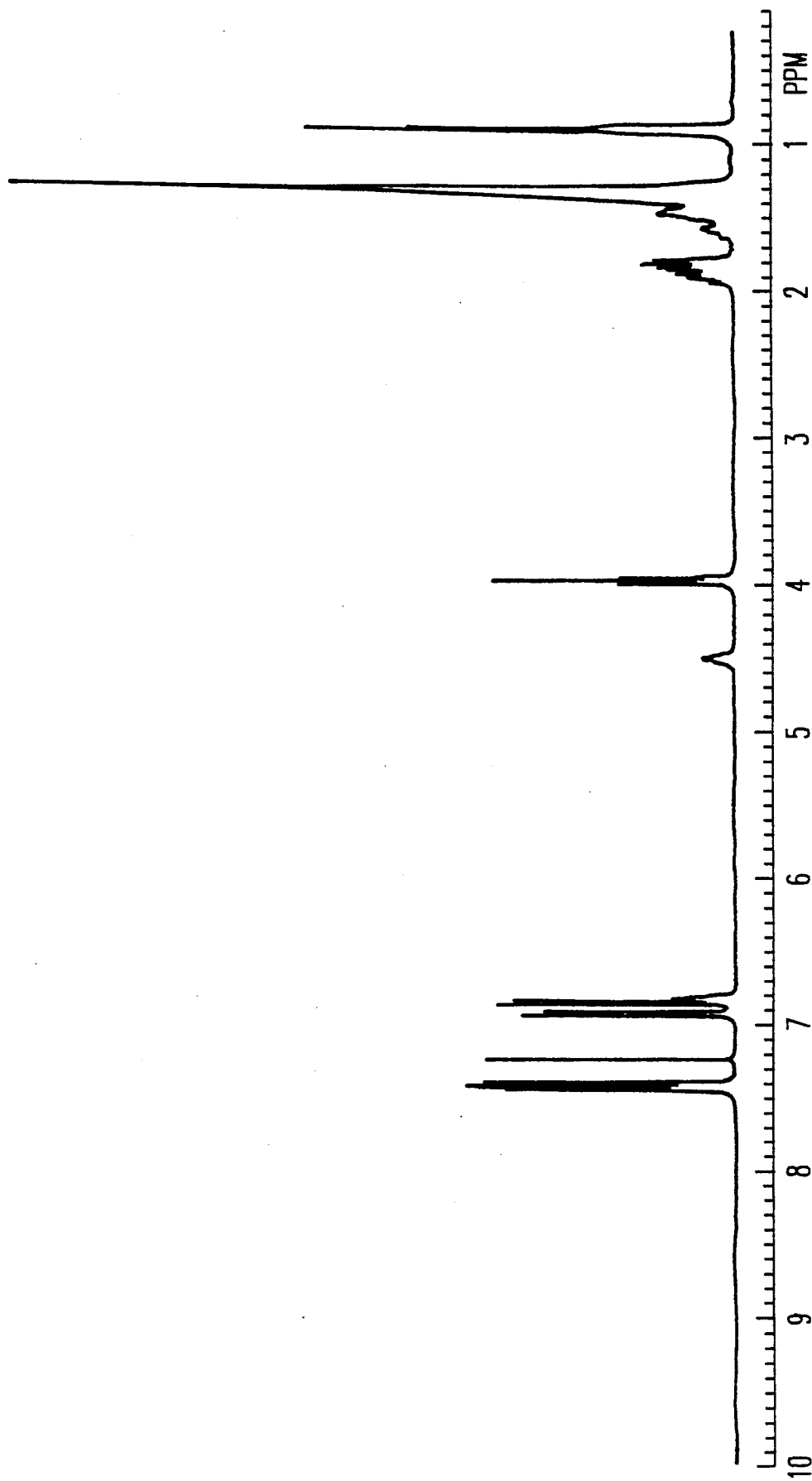
Figure 9C:
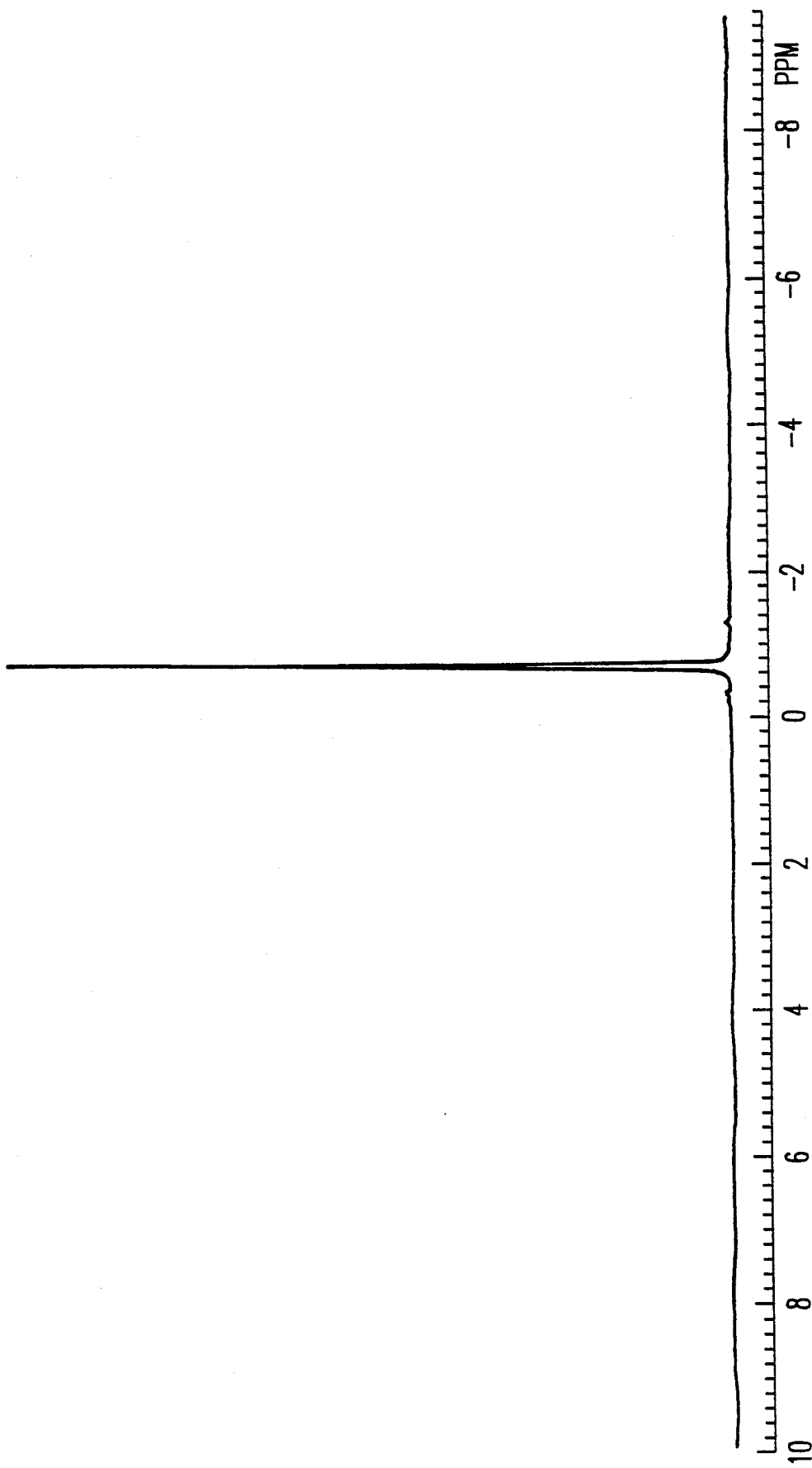

IR spectrum, 1H-NMR spectrum and F-NMR spectrum of the compound were as shown in FIG. 9(a), FIG. 9(b) and FIG. 9(c), respectively. Elemental analysis (%) [theoretical] was as follows: C:74.51 [74.42], H:8.19 [8.33], 0:6.29 [6.20], F:11.01 [11.05]

EXAMPLE 10

Preparation of Compound No. 5-4' in Table 5-2

1) Into 100 ml of dry DMF containing 0.4 g of sodium hydride (purity 60%), were added dropwise 1.84 g of S-form oa 1-trifluoromethyl-heptanol, at room temperature with such a speed not causing too rapid generation of hydrogen, to prepare sodium salt (alkoxide) of S-form oa 1-trifluoromethyl-heptanol. After the addition was over, stirring was continued further an hour at room temperature, followed by adding thereto 2.50 g of p-chloromethyl-iodobenzene (prepared by reducing p-iodobenzoic acid with lithium aluminum hydride and then chlorinating with thionyl chloride) and then stirring for 24 hours at room temperature. After completion of the reaction, the product was introduced into iced water, and extracted with hexane. The hexane phase was washed subsequently with water, 1N-hydrochloric acid aqueous solution and then water, followed by distilling off the hexane to obtain 3.8 g of oily oa p-(1-trifluoro-methylheptyloxymethyl)iodobenzene.

2) Example 9, 2) was repeated except using 2.0 g of oa instead of 1.9 g of oa p-(1-trifluoromethylheptyloxy)iodobenzene, to obtain 2.20 g of while crystalline oa p-n-decyloxy-p'-(1-trifluoromethyl-heptyloxy,methyl)-tolan [Compound No. 5-4'] of this invention.

Figure 10A:
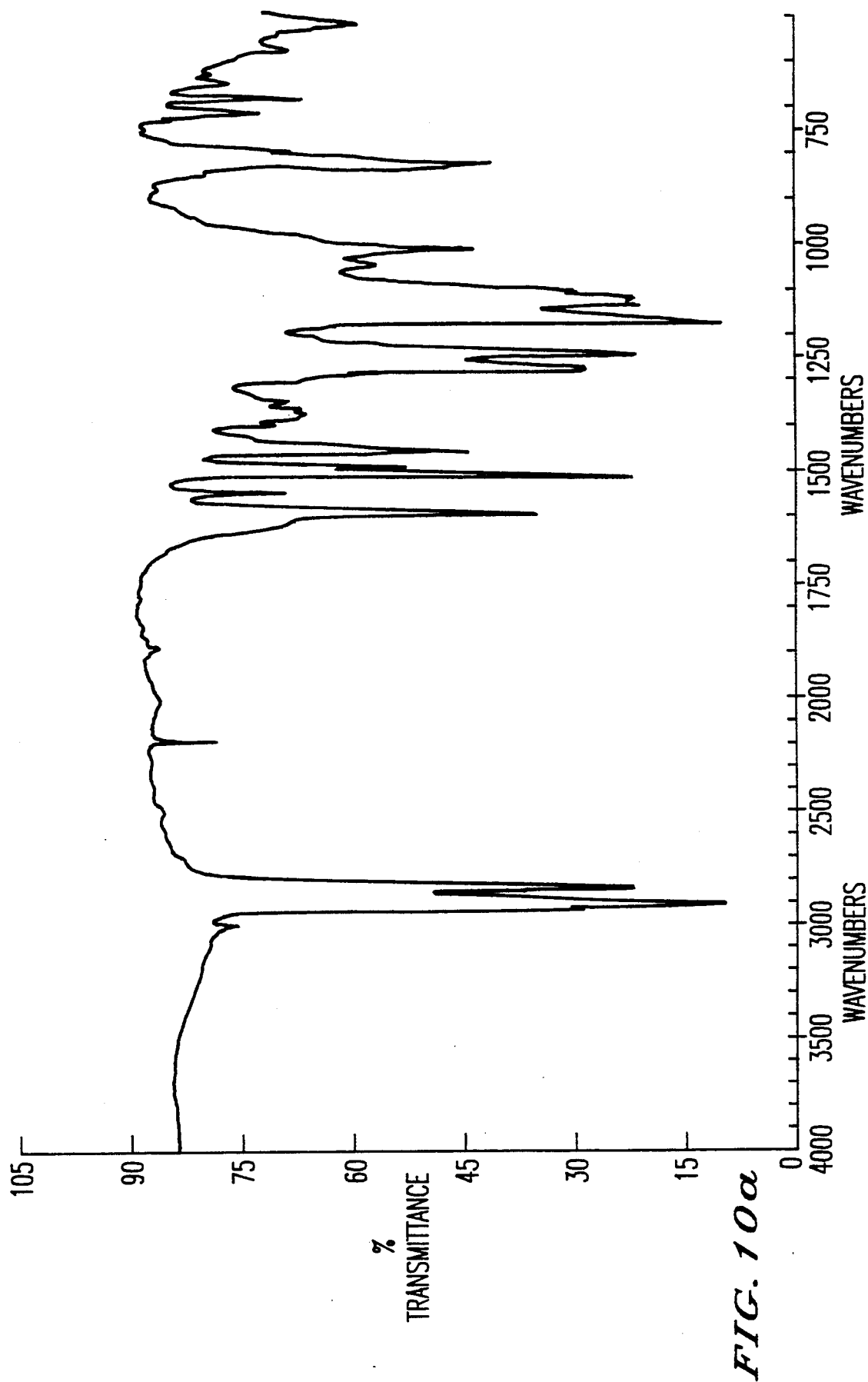
Figure 10B:
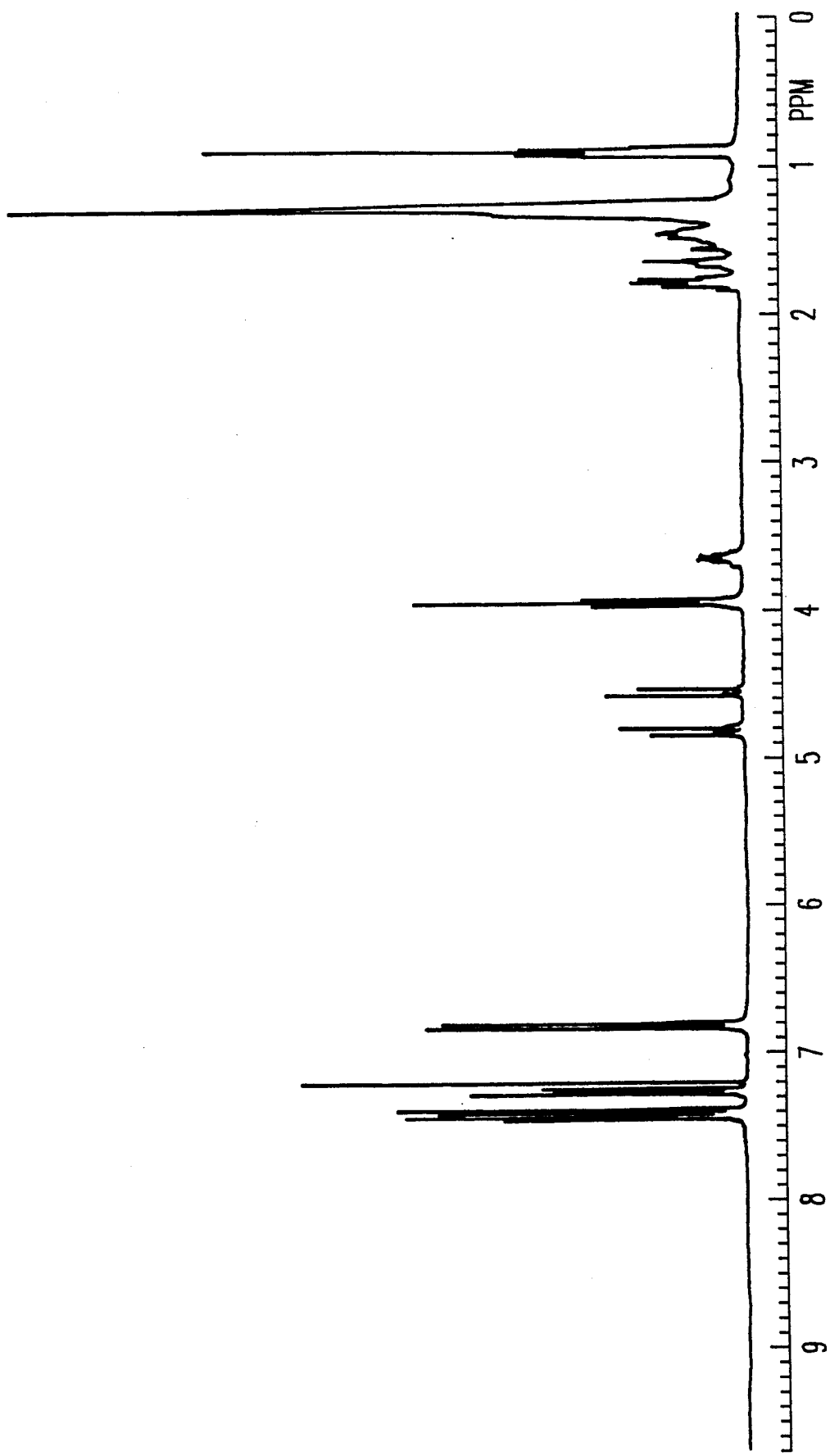
Figure 10C:
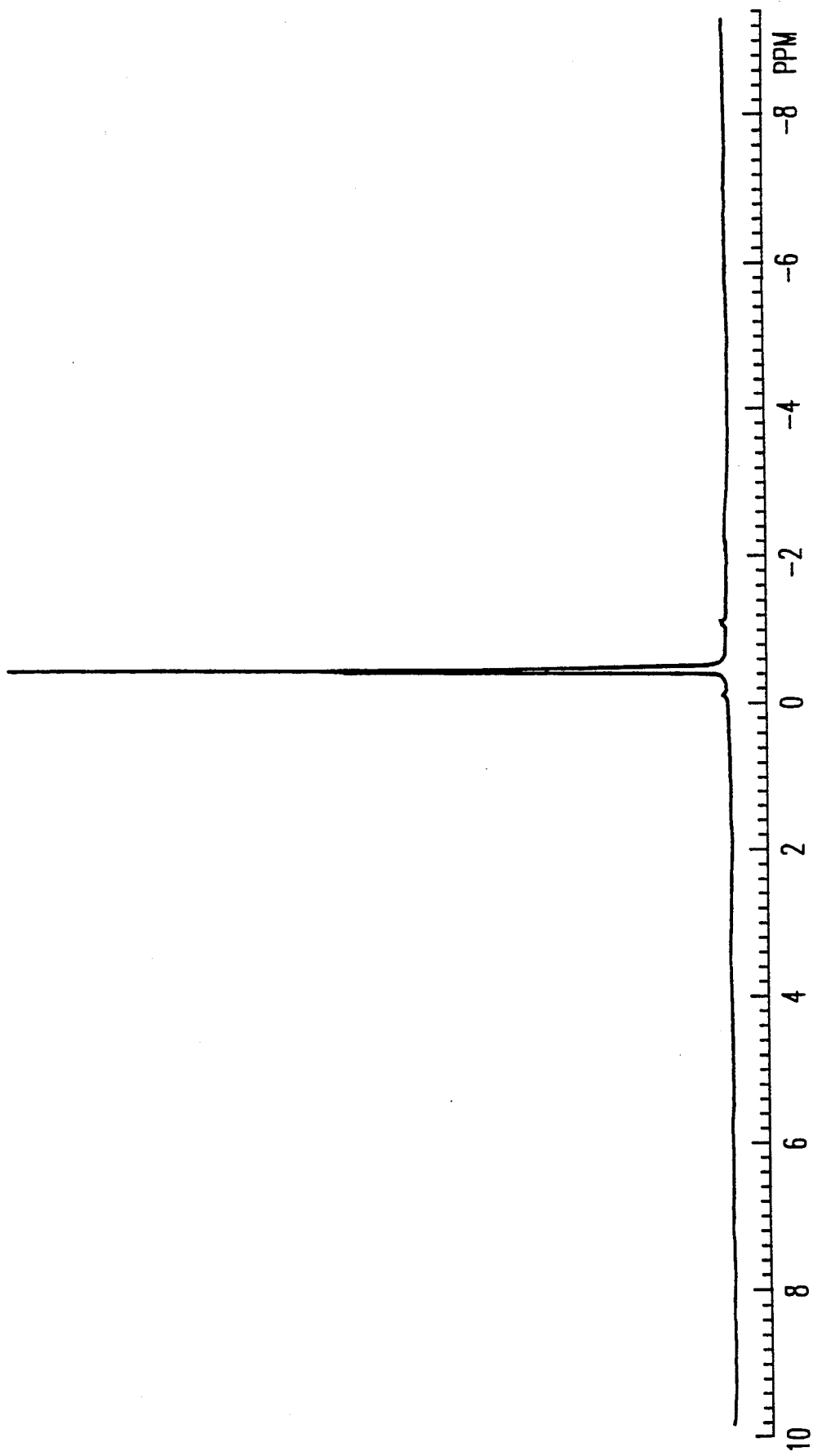

IR spectrum, 1H-NMR spectrum and F-NMR spectrum of the compound were as shown in FIG. 10(a), FIG. 10(b) and FIG. 10(c), respectively. Elemental analysis (%) [theoretical] was as follows: C:74.80 [74.72], H:8.41 [8.49], 0:5.81 [6.04], F:10.98 [10.75].

EXAMPLE 11

Preparation of Compound No. 7-5 in able 7

To 0.90 g of 2-n-decyloxy-6-carboxy-naphthalene, 5 ml of thionyl chloride were added and refluxed for 2 hours. Thereafter, excess thionyl chloride was removed under reduced pressure to obtain an oily acid chloride, which was used as such (without purification) in the following reaction.

This acid chloride was dissolved into 10 ml of dry pyridine, to which, under cooling, 0.55 g of 1-trifluoromethyl-heptanol were added dropwise slowly. After the addition was over, stirring was continued an hour under cooling with ice and then reacting them at 80° C. for 6 hours. After completion of the reaction, the product was introduced into iced water, and extracted with toluene. The toluene phase was washed subsequently with 1N-hydrochloric acid aqueous solution, water, saturated aqueous solution of sodium hydrogen carbonate and then water, followed by distilling off the toluene to obtain a pale yellow oily material. This material was dissolved into hexane, followed by purifying with silica gel column to obtain oa 2-n-decyloxy-6-(1-trifluoromethyl-heptyloxycarbonyl) naphthalene [Compound No. 7-5] of this invention.

Figure 11A:
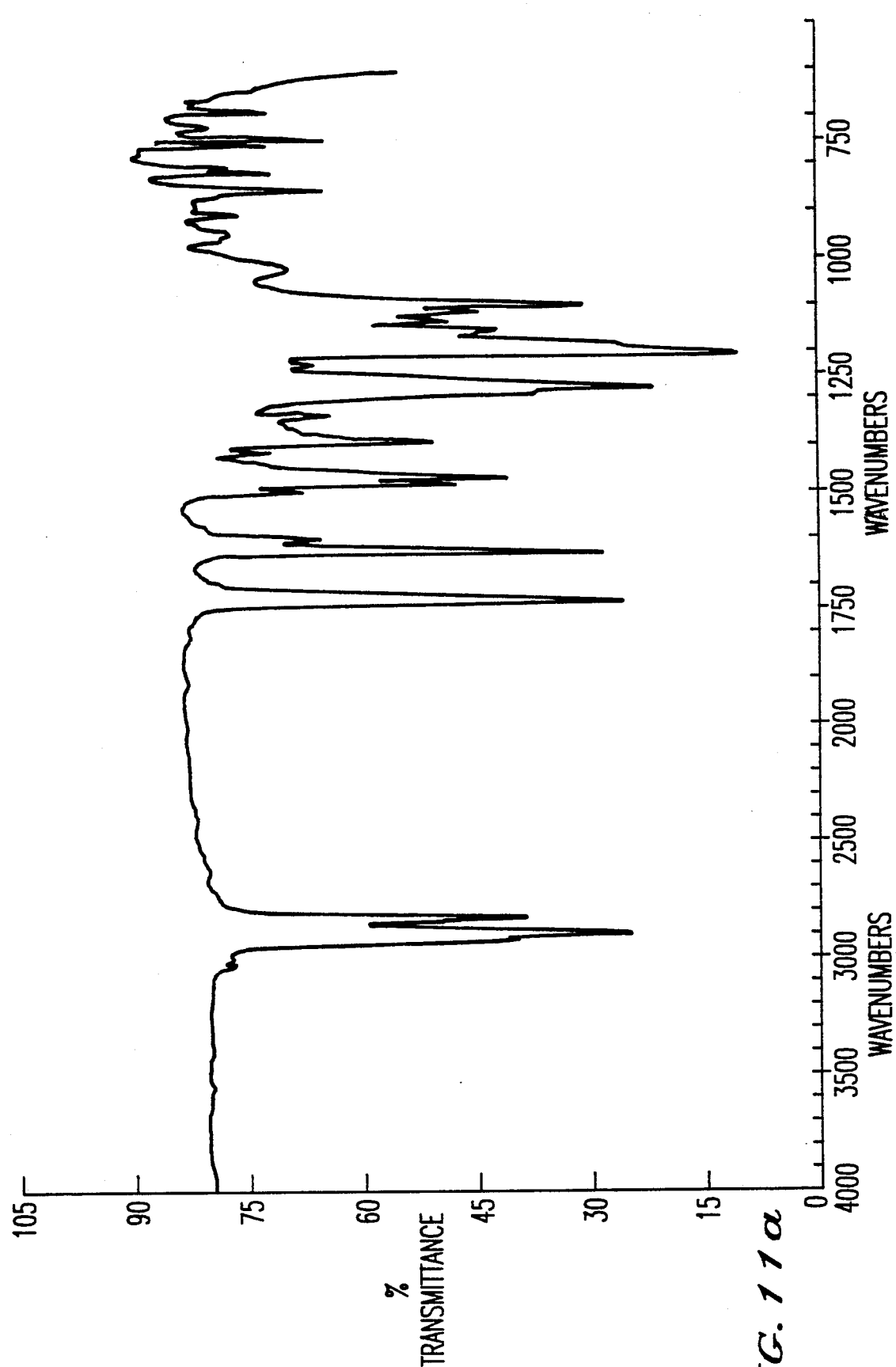
Figure 11B:
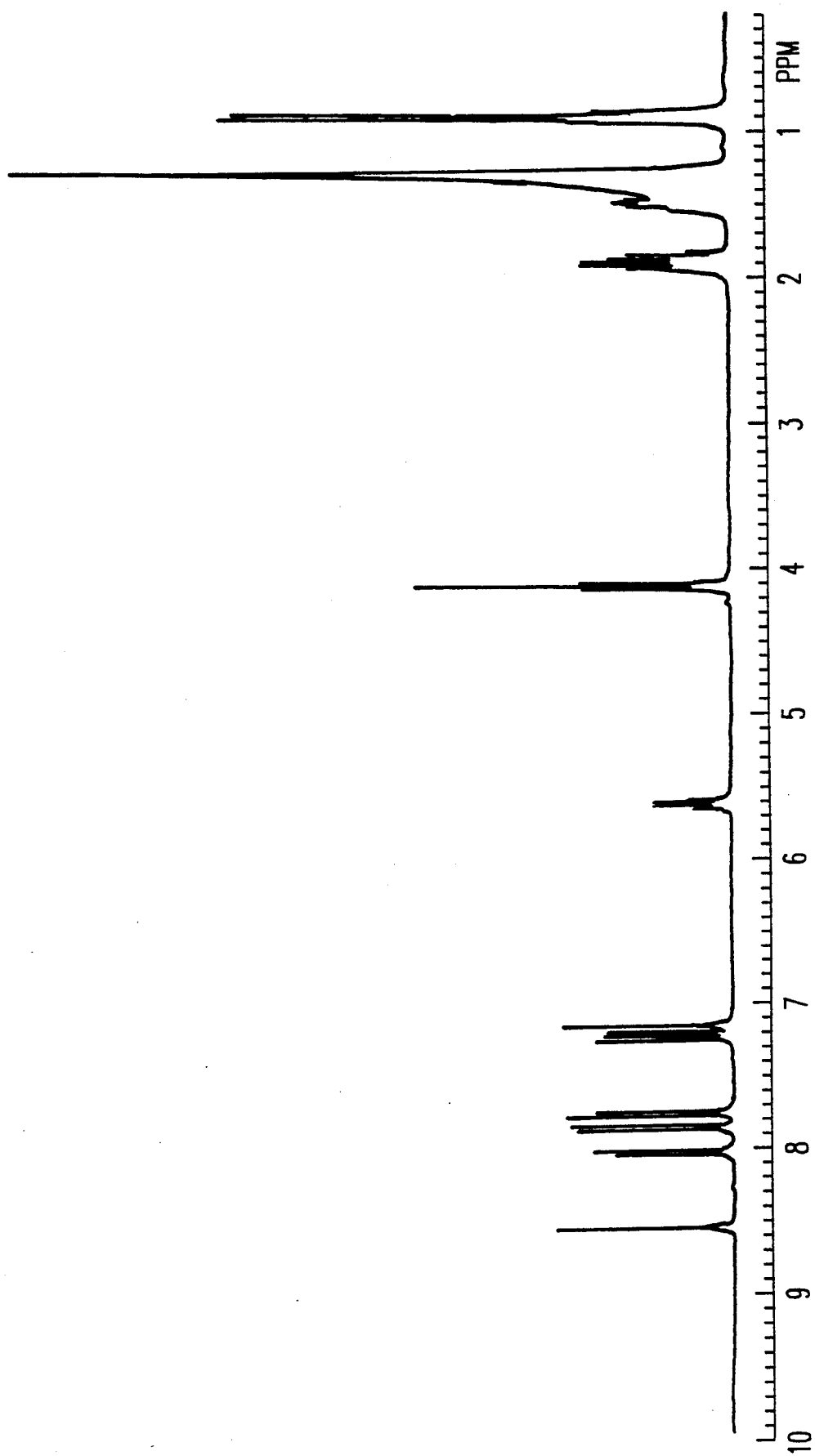
Figure 11C:
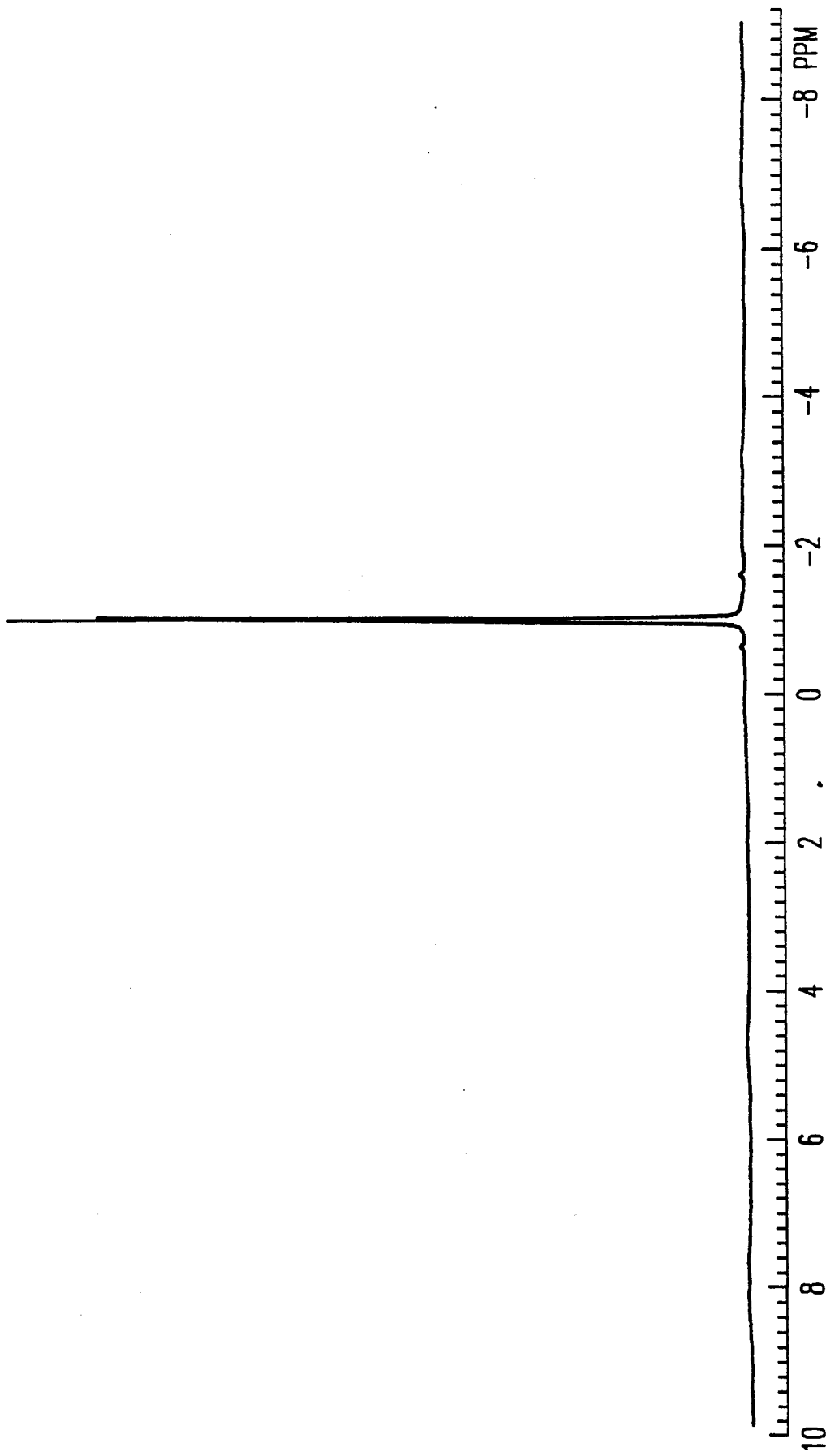

IR spectrum, 1H-NMR spectrum and F-NMR spectrum of the compound were as shown in FIG. 11(a), FIG. 11(b) and FIG. 11(c), respectively. Elemental analysis (%) [theoretical] was as follows: C:70.28 [70.44], H:8.41 [8.30], 0:9.83 [9.72], F:11.48 [11.54]

EXAMPLE 12

Preparation of Compound No. 8-18 in Table 8-1

1) To 34.0 g of p-iodo-phenol dissolved in 350 ml of DMSO, were added 7.4 g of sodium hydroxide dissolved in 50 ml of water and stirred to obtain a homogeneous solution. Then, 32.4 g of n-decyl bromide were added and stirred at room temperature for 3 days. The resulting solution was introduced into 1 l of iced water, and extracted three times with hexane. The hexane phase was washed with water, followed by distilling off the hexane to obtain 46.6 g of oily p-n-decyloxy-iodobenzene.

Using 320 mg of dichloro-bis-triphenylphosphine palladium and 80 mg of cuprous iodide as the catalyst, 30 g of p-n-decyloxy-iodobenzene and 8.4 g of oa 3-methyl-1-butyne-3-ol were reacted in 200 ml of triethylamine under an atmosphere of nitrogen at room temperature for 24 hours. After completion of the reaction, the triethylamine was removed and then the product was extracted with hexane. The hexane phase was washed with 1N hydrochloric acid aqueous solution and then with water, followed by distilling off the hexane to obtain 22.8 g of a solid compound of the formula:

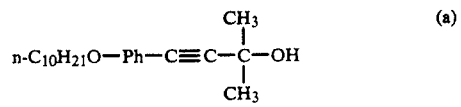

(a)

To 22.8 g of this compound dissolved in 400 ml of dry toluene, were added 9.9 g of sodium hydroxide powder, followed by heating under reflux for an hour. After cooling, the product was washed with water and then the toluene was removed. The resulting black oil was extracted with methanol, followed by removing methanol to obtain 13.2 g of oily p-n-decyloxyphenylacetylene.

2) Using 48 mg of dichloro-bis-triphenylphosphin palladium and 12 mg of cuprous iodide as the catalyst, 1.0 g of p-n-decyloxyphenylacetylene and 1.6 g of S-form oa p-(1-trifluoromethylheptyloxycarbonyl)iodobenzene (prepared by reacting S-form oa 1-trifluoromethyl-heptanol with p-iodo-benzoic acid chloride obtained by reaction of p-iodo-benzoic acid with thionyl chloride) were reacted in 30 ml of triethylamine under an atmosphere of nitrogen at room temperature for 24 hours. After completion of the reaction, the triethylamine was removed and then the product was extracted with hexane. The hexane phase was washed with 1N hydrochloric acid aqueous solution and then with water, followed by treating with silica gel column and then with water, followed by treating with silica gel column and then recrystalyzing with ethanol to obtain 1.4 g of a compound of the formula:

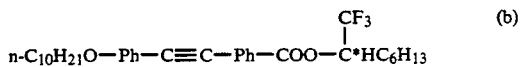

(b)

3) To 25 ml of ethanol containing 0.3 g of this compound, was added 0.05 g of 5% Pd-C catalyst, followed by carrying out hydrogenation within an atmosphere of hydrogen at normal pressure under stirring at room temperature. After it was confirmed that no absorption of hydrogen was observed, the catalyst was removed by filtration and then the ethanol was removed under reduced pressure. The resulting oil was dissolved into hexane and purified with silica gel column to obtain 0.24 g of an oily compound [Compound No. 8-18] of this invention.

Figure 12A:
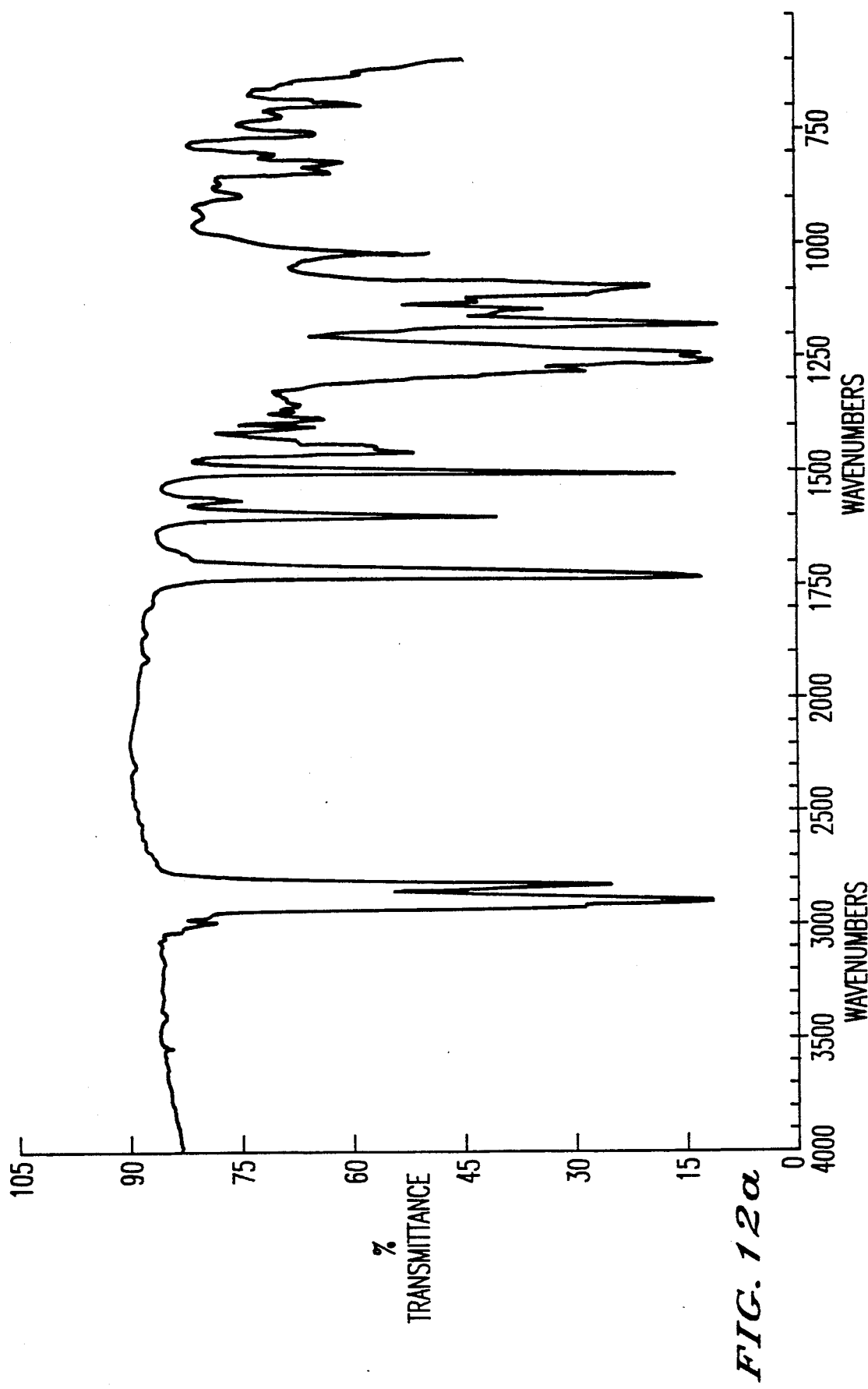
Figure 12B:
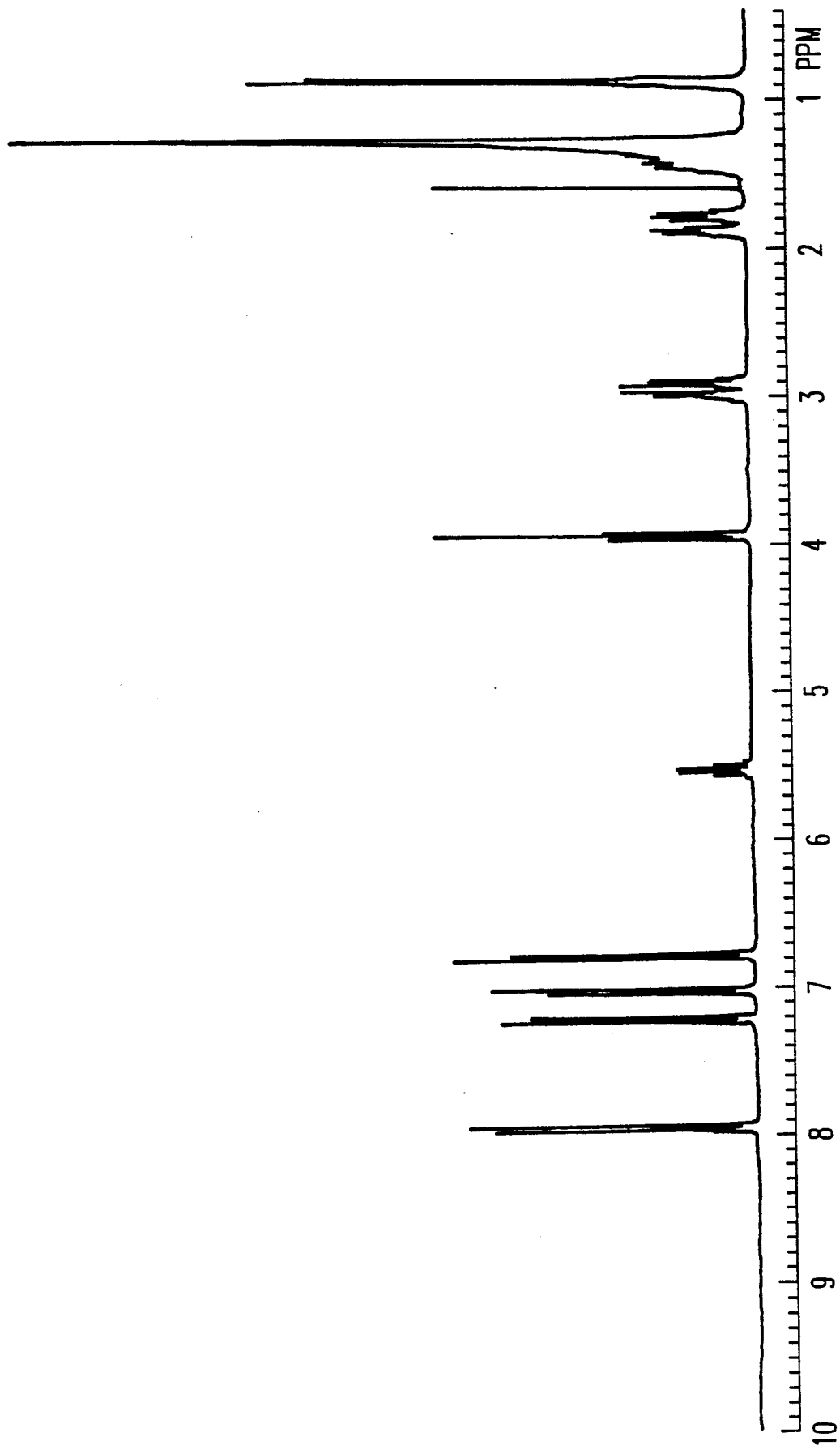
Figure 12C:
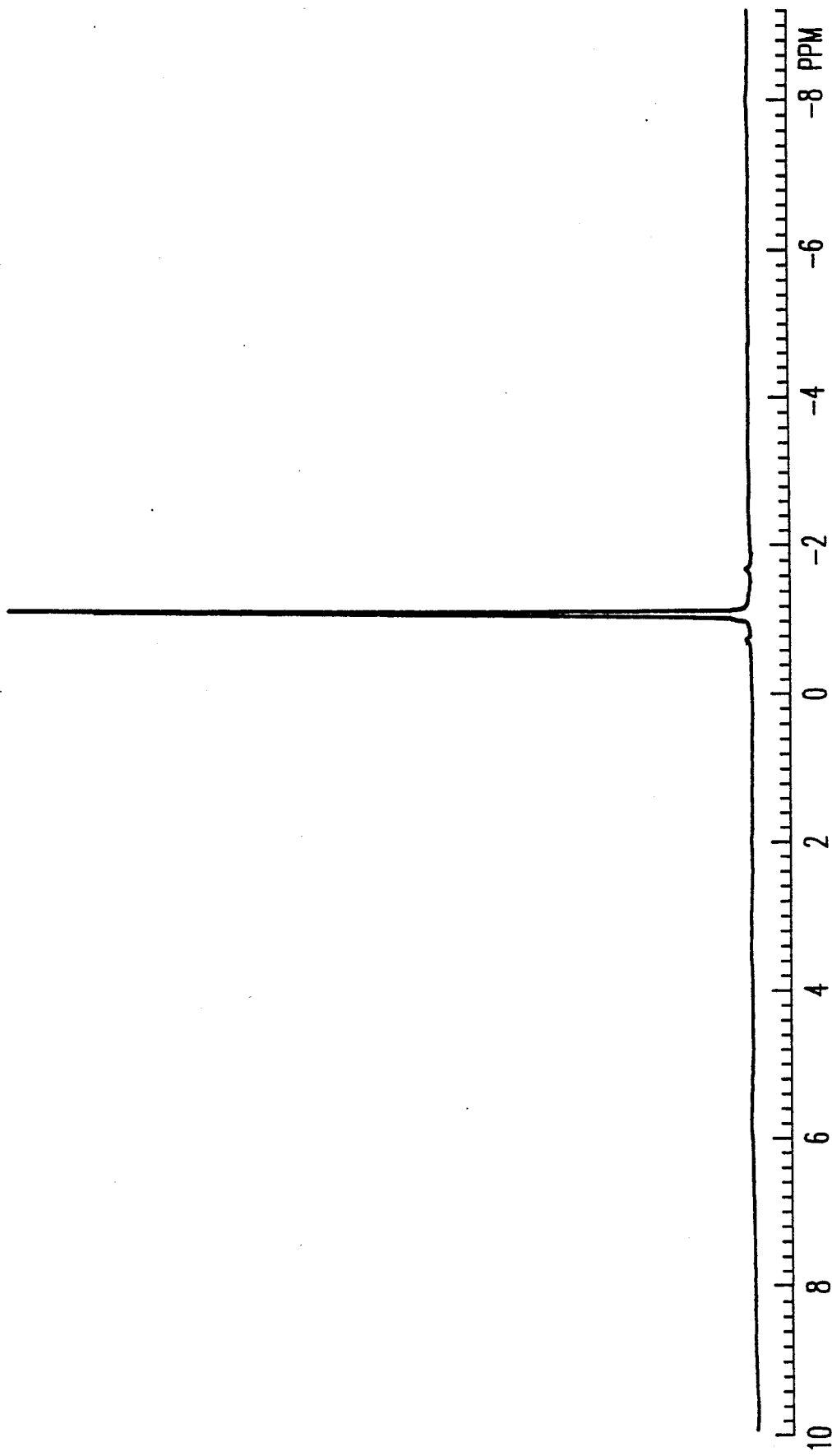

IR spectrum, $^1$H-NMR spectrum and F-NMR spectrum of the compound were as shown in FIG. 12(a), FIG. 12(b) and FIG. 12(c), respectively. Elemental analysis (%) [theoretical] was as follows: C:72.01 [72.26], H:8.72 [8.58], F:10.62 [10.40].

EXAMPLE 13

Preparation of Compound No. 9-6 in Table 9

1) To 50 ml of anhydrous methylene chloride containing dissolved therein 2.0 g of 2-chloronicotinic acid and 2.4 g of R-form oa 1-trifluoromethyl-heptanol, were added 2.7 g of N',N'-dicyclohexylcarbodiimide and 300 mg of 4-dimethylaminopyridine and stirred at room temperature for 2 days. After completion of reaction, the methylene chloride was removed, and then the product was extracted with hexane. The hexane phase was washed with 1N sodium hydroxide aqueous solution and then with water, followed by treating with silica gel column to obtain 2.8 g of liquid R-form oa 1-trifluoromethylheptyl 2-chloro-nicotinate.

2) Using 40 mg of dichloro-bis-triphenylphosphen palladium, 60 mg of triphenyl phosphine and 10 mg of cuprous iodide as the catalyst, 0.91 g of p-n-decyloxyphenylacetylene [prepared in Example 12] and 1.15 g of R-form oa 1-trifluoromethyl-heptyl 2-chloro-nicotinate were reacted in 30 ml of triethylamine under reflux within an atmosphere of nitrogen for 10 hours. After completion of the reaction, the triethylamine was removed and then the product was extracted with hexane. The hexane phase was washed with 1N hydrochloric acid aqueous solution and then with water, followed by treating with silica gel column and then recrystallizing with ethanol to obtain 0.52 g of a compound [Compound No. 9-6] of this invention.

Figure 13A:
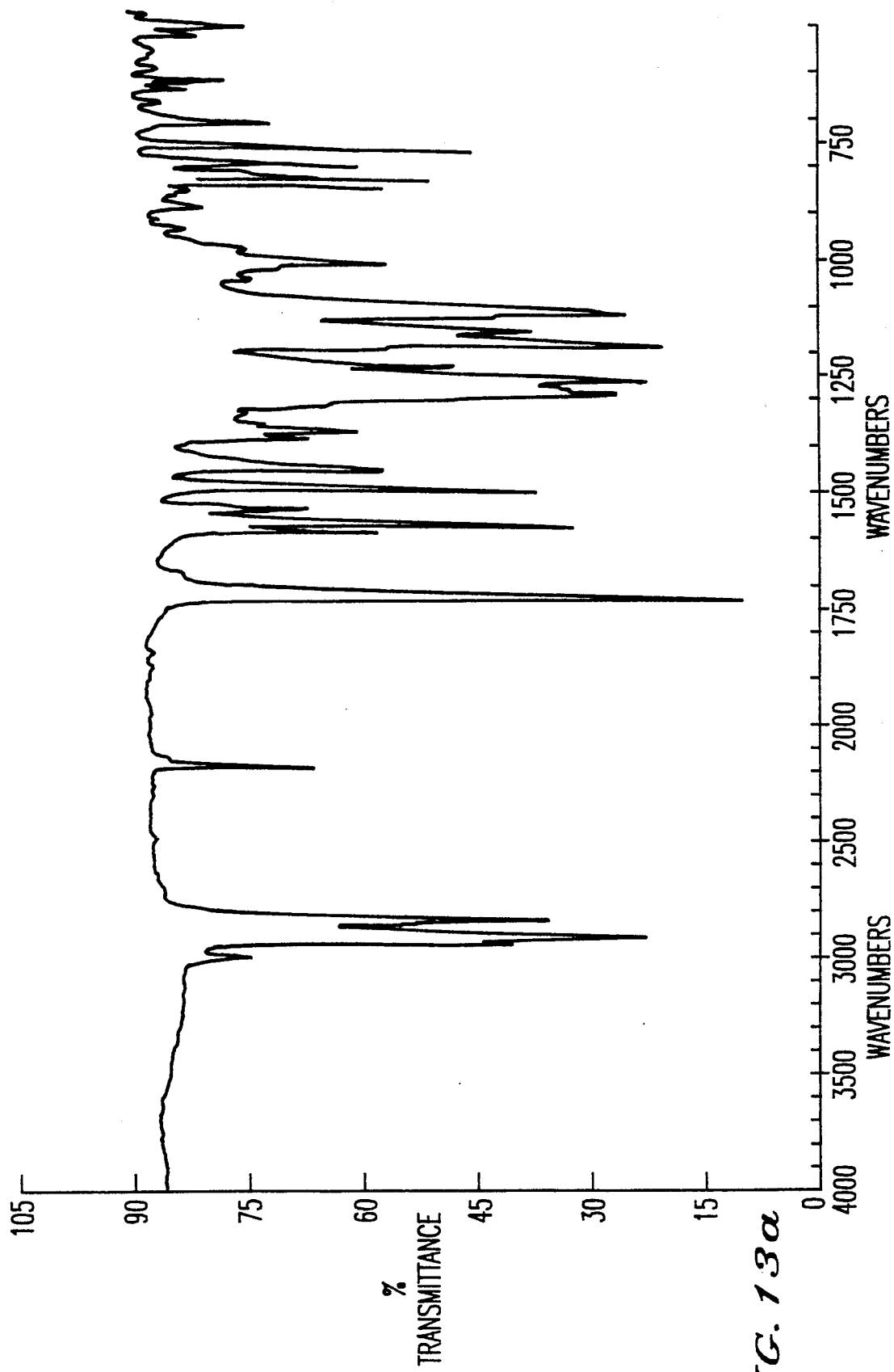
Figure 13B:
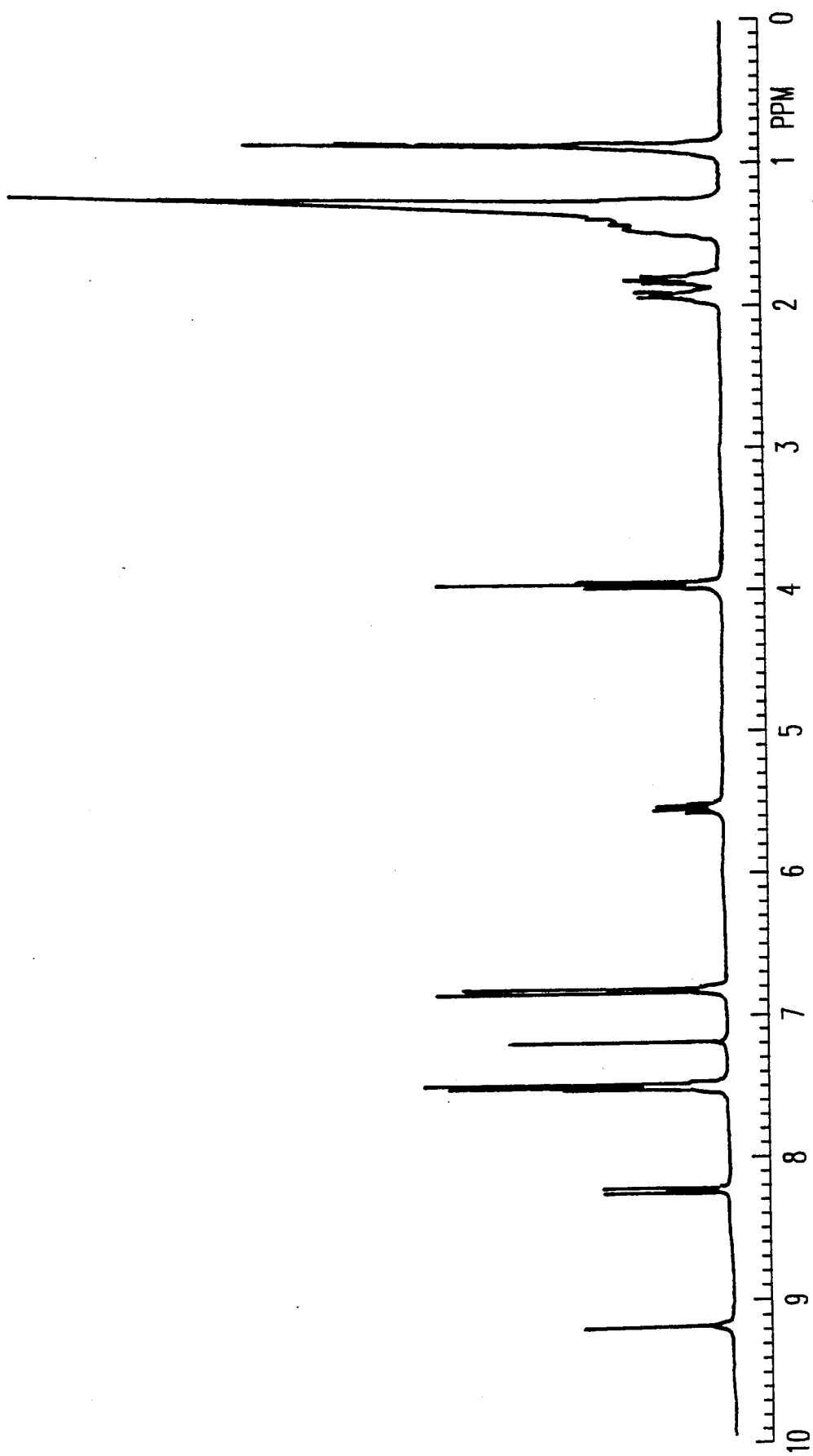
Figure 13C:
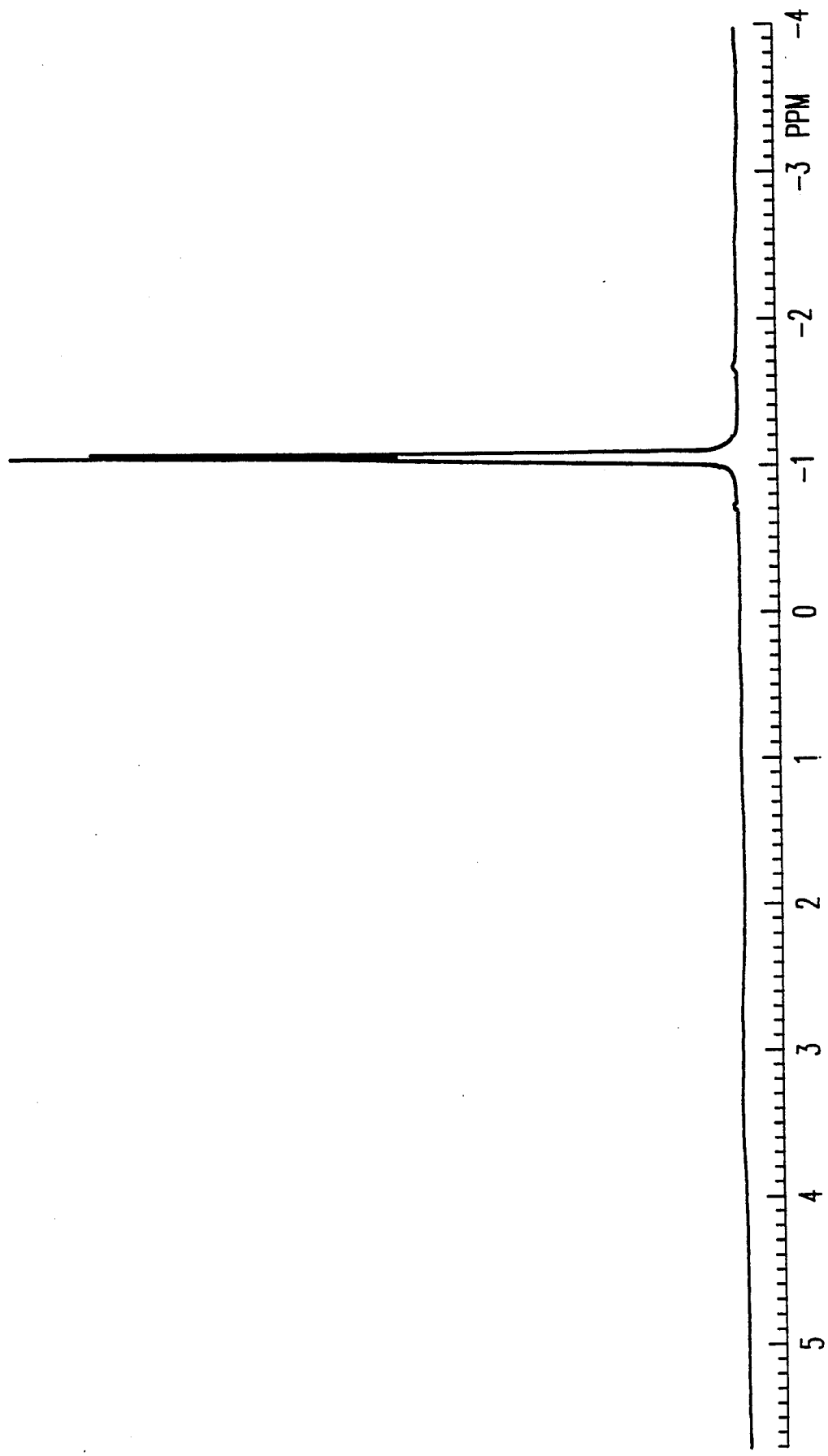

IR spectrum, $^1$H-NMR spectrum and F-NMR spectrum of the compound were as shown in FIG. 13(a), FIG. 13(b) and FIG. 13(c), respectively. Elemental analysis (%) [theoretical] was as follows: C:70.32 [70.45], H:7.53 [7.71], N:2.71 [2.57], F:10.55 [10.46]

EXAMPLE 14

Liquid crystal compositions

Liquid crystal compositions containing known smectic liquid crystals and a compound of this invention were prepared according to the following formulation:

| | |
|---|---|
| $C_9H_{19}$—Pym > —Ph—O—$C_8H_{17}$ | 45% |
| $C_8H_{17}$—Pym > —Ph—O—$C_8H_{17}$ | 45% |
| Each Compound of Examples | 10.0% |

Each composition was injected into cells of 2 micron m thickness, provided with transparent electrodes which had been coated with polyvinyl alcohol and surface-aligned by rubbing. Each element was placed between two crossed polarizers, and response time was measured from change of intensity of transmitted light when voltage of ±10 V was applied. The results (Response Time, micro sec.) were as shown in Table 10.

TABLE 10

| Compound (Ex. No.) | 1 | 2 | 3 | 4 | 5 | 6 | 7 |
|---|---|---|---|---|---|---|---|
| Response Time | a.120 | a.70 | a.130 | a.100 | a.90 | a.80 | a.110 |
| Compound (Ex. No.) | 8 | 9 | 10 | 11 | 12 | 13 | |
| Response Time | a.60 | a.60 | a.100 | a.90 | a.160 | a.150 | |

(a.: about)

EXAMPLE 15

Liquid crystal compositions

Example 14 was repeated except that the following formulation was used.

| | |
|---|---|
| $C_7H_{15}$—Pym > —Ph—O—$C_9H_{19}$ | 36.3% |
| $C_8H_{17}$—Pym > —Ph—O—$C_9H_{19}$ | 61.7% |
| Each Compound written in Table 11 | 2.0% |

The results were as shown in Table 11.

TABLE 11

| No. | Compound | Response Time |
|---|---|---|
| 15-1 | Compound of Example 11 | 270 |
| 15-2 | Compound of Example 5 | 475 |
| 15-3 | $C_{10}H_{21}O$—Nt—COO—$C^*HCH_3$ with CH$_3$ branch | 935 |

(No. 15-3 is a comparative example.)

Optically active compounds according to the present invention have unexpected effects as follows:

(1) By addition of optically active compounds of this invention, which have large intramolecular dipole moment, there can be attained ferroelectic phase with high value of spontaneous polarization and quick optical response; whereas liquid crystals or liquid crystal compositions, showing non chiral smectic C phase or H phase, don't provide ferroelectricity and results in spontaneous polarization value of zero.

(2) While optically active compounds to be added to ferroelectic liquid crystals or liquid crystal compositions are restricted to ones of either R form or S-form in accordance with sign of spontaneous polarization of the liquid crystals or liquid crystal compositions; according to the invention, there can be obtained any of R-form and S-form optically active compounds, and spontaneous polarization value of the liquid crystals or liquid crystal compositions c an be remarkably increased by addition of such compounds, whereby rapid optical response can be attained.

(3) Optically active compounds of the present invention have a linear molecular structure, and, when they are added to liquid crystals or liquid crystal compositions, deleterious influences upon phase systems or phase transition temperatures of these can be greatly reduced.

(4) Different from known compounds which are merely being optically active there can be obtained according to the present invention optically active compounds, having asymmetric carbon atom-containing alkyl chains independently on both sides through substituted or unsubstituted skeleton (such as tolan skeleton), which compounds make it possible to control or design freely properties or performances, such as helical pitch, spontaneous polarization value, dieletric anisotropy and optical anisotropy, when added to liquid crystals or liquid crystal compositions.

(5) In addition to use as formulation ingredients for ferroelectic liquid crystal compositions or non-chiral smectic liquid crystal compositions, the optically active compounds of the present invention may also be added to nematic liquid crystal compositions, whereby occurrence of reverse domain in liquid crystal cells of TN type can be controlled.

(6) Control of hydrophobicity which is nature necessary for producing LB membranes is easily attained, and there can be obtained monomolecular laminated films.

(7) They are highly stable toward light, heat and water.

Thus, the optically active compounds of the present invention are advantageously used in the production of ferroelectric smectic liquid crystal compositions.

Having described the present invention, it will now be apparent to one skilled in the art that many changes and modifications can be made to the embodiments disclosed while remaining within the spirit and scope of the present invention.

Throughout the present specification the notation C#C is also used to represent C≡C.

What is claimed as new and desired to be secured by Letters Patent is:

1. An optically active compound having the formula (1):

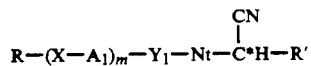

wherein R and R' are the same or different alkyl groups containing 1 to 20 carbon atoms, which are each unsubstituted or are each substituted with at least one substituent selected from the group consisting of F, Cl and alkoxy groups; X is a direct bond, O, S, COO, OCO, OCOO or C≡C; $Y_1$ is COO, O, $CH_2O$ or C≡C; $A_1$ is 1,4-phenylene (ph), fluoro-substituted 1,4-phenylene, or 2,5-pyridylene (pyr) and m is 1 Nt represents 2,6-naphthylene.

2. The compound of claim 1, wherein at least one of R and R' is an optically active alkyl group which is unsubstituted or is substituted with F, Cl or an alkoxy group.

3. The compound of claim 1, wherein X is a direct bond or O.

4. The compound of claim 1, wherein $Y_1$ is —COO—.

5. The compound of claim 1, wherein X is a direct bond.

6. The compound of claim 1, wherein $A_1$ is Ph.

7. The compound of claim 5, wherein $Y_1$ is —COO—.

8. The compound of claim 6, wherein $Y_1$ is —COO—.

9. The compound of claim 5, wherein $A_1$ is Ph.

10. The compound of claim 1, wherein $A_1$ is Ph.

11. The compound of claim 9, wherein $Y_1$ is —COO—.

12. The compound of claim 8, wherein X is a direct bond or oxygen.

13. The compound of claim 7, wherein $A_1$ is Ph or fluoro substituted Ph or 2,5-pyridylene.

14. The compound of claim 9, wherein $Y_1$ is —COO—, —O—, —$CH_2O$— or —C≡C—.

* * * * *